US012679825B2

(12) United States Patent
Pollard et al.

(10) Patent No.: US 12,679,825 B2
(45) Date of Patent: Jul. 14, 2026

(54) CRYSTALLINE AND AMORPHOUS FORMS OF A δ-OPIOID MODULATOR

(71) Applicant: Trevena, Inc., Chesterbrook, PA (US)

(72) Inventors: Victoria A. Pollard, Bathgate (GB); Laura E.N. Allan, Dalkeith (GB); Hayley A. Reece, Dalkeith (GB); Patrick J. Koestler, Doylestown, PA (US)

(73) Assignee: Trevena, Inc., Chesterbrook, PA (US)

( * ) Notice: Subject to any disclaimer, the term of this patent is extended or adjusted under 35 U.S.C. 154(b) by 400 days.

(21) Appl. No.: 18/250,915

(22) PCT Filed: Oct. 27, 2021

(86) PCT No.: PCT/US2021/056764

§ 371 (c)(1),
(2) Date: Apr. 27, 2023

(87) PCT Pub. No.: WO2022/093904

PCT Pub. Date: May 5, 2022

(65) Prior Publication Data

US 2023/0391749 A1 Dec. 7, 2023

Related U.S. Application Data

(60) Provisional application No. 63/106,202, filed on Oct. 27, 2020.

(51) Int. Cl.

| | |
|---|---|
| ***C07D 401/14*** | (2006.01) |
| ***A61K 31/454*** | (2006.01) |
| ***A61K 45/06*** | (2006.01) |
| ***A61P 25/04*** | (2006.01) |
| ***A61P 25/06*** | (2006.01) |

(52) U.S. Cl.

CPC .......... *C07D 401/14* (2013.01); *A61K 31/454* (2013.01); *A61K 45/06* (2013.01); *A61P 25/04* (2018.01); *A61P 25/06* (2018.01); *C07B 2200/13* (2013.01)

(58) Field of Classification Search

None

See application file for complete search history.

(56) References Cited

U.S. PATENT DOCUMENTS

| | | | |
|---|---|---|---|
| 3,863,633 | A | 2/1975 | Ryde et al. |
| 3,867,519 | A | 2/1975 | Michaels |
| 3,868,445 | A | 2/1975 | Ryde et al. |
| 3,960,150 | A | 6/1976 | Hussain et al. |
| 3,963,025 | A | 6/1976 | Whitaker et al. |
| 4,115,538 | A | 9/1978 | Satoh et al. |
| 4,186,184 | A | 1/1980 | Zaffaroni |
| 4,209,514 | A | 6/1980 | Gruenfeld |
| 4,303,637 | A | 12/1981 | Shell et al. |
| 5,086,063 | A | 2/1992 | Ciganek et al. |
| 5,436,128 | A | 7/1995 | Harpold et al. |
| 5,443,505 | A | 8/1995 | Wong et al. |
| 5,869,079 | A | 2/1999 | Wong et al. |
| 5,883,290 | A | 3/1999 | Okada et al. |
| 6,465,453 | B1 | 10/2002 | Hauser et al. |
| 7,098,203 | B2 | 8/2006 | Wu et al. |
| 7,488,745 | B2 | 2/2009 | Yu et al. |
| 7,504,424 | B2 | 3/2009 | Yu et al. |
| 8,173,678 | B2 | 5/2012 | Carroll et al. |
| 8,664,214 | B2 | 3/2014 | Braje et al. |
| 8,685,990 | B2 | 4/2014 | Coats et al. |
| 9,168,254 | B2 | 10/2015 | Corson et al. |
| 10,246,436 | B2 | 4/2019 | Speerschneider et al. |
| 11,225,487 | B2 | 1/2022 | Speerschneider et al. |
| 11,465,980 | B2 | 10/2022 | Speerschneider et al. |
| 11,702,408 | B2 | 7/2023 | Speerschneider et al. |
| 2002/0028821 | A1 | 3/2002 | Howard |
| 2002/0077323 | A1 | 6/2002 | McLean et al. |
| 2003/0018048 | A1 | 1/2003 | Bayod Jasanada et al. |
| 2005/0234234 | A1 | 10/2005 | Gu et al. |
| 2006/0020011 | A1 | 1/2006 | Wu et al. |
| 2007/0043015 | A1 | 2/2007 | DeVita et al. |
| 2007/0129419 | A1 | 6/2007 | Grundschober et al. |
| 2009/0042896 | A1 | 2/2009 | Jablonski et al. |
| 2011/0245232 | A1 | 10/2011 | Braje et al. |
| 2011/0313163 | A1 | 12/2011 | Hudlicky et al. |
| 2012/0010212 | A1 | 1/2012 | Nettekoven et al. |
| 2012/0245181 | A1 | 9/2012 | Yamashita et al. |
| 2014/0335190 | A1 | 11/2014 | Pettersson |
| 2015/0225424 | A1 | 8/2015 | Guillemont et al. |
| 2016/0052882 | A1 | 2/2016 | Vardanyan et al. |
| 2017/0210725 | A1 | 7/2017 | Speerschneider et al. |

(Continued)

FOREIGN PATENT DOCUMENTS

| | | | |
|---|---|---|---|
| CA | 2516623 | A1 | 9/2004 |
| CN | 1639121 | A | 7/2005 |
| CN | 101778837 | A | 7/2010 |
| CN | 108025002 | A | 5/2018 |
| CN | 111138425 | A | 5/2020 |
| EP | 0339579 | A2 | 11/1989 |
| JP | H1313461 | A | 12/1989 |
| JP | 1990049766 | A | 2/1990 |
| JP | 2000516234 | A | 12/2000 |
| JP | 2002541249 | A | 12/2002 |
| JP | 2004512263 | A | 4/2004 |
| JP | 2006511474 | A | 4/2006 |
| JP | 2007507504 | A | 3/2007 |
| JP | 2008503511 | A | 2/2008 |
| JP | 2009517435 | A | 4/2009 |

(Continued)

OTHER PUBLICATIONS

Mcgreevey. European Journal of Pain Supplements, 2011, 5(2), 365-376 (Year: 2011).*

(Continued)

*Primary Examiner* — Noble E Jarrell
(74) *Attorney, Agent, or Firm* — Goodwin Procter LLP

(57) ABSTRACT

The present disclosure provides novel crystalline forms of a compound that acts as a δ-opioid effector, processes for preparing and precipitating amorphous and crystalline forms of the compound, and uses thereof.

19 Claims, 47 Drawing Sheets

(56) References Cited

U.S. PATENT DOCUMENTS

2019/0202803 A1 7/2019 Speerschneider et al.
2020/0231564 A9 7/2020 Speerschneider et al.
2021/0061790 A1 3/2021 Speerschneider et al.
2021/0061812 A1 3/2021 Speerschneider et al.
2022/0348588 A1 11/2022 Speerschneider et al.
2023/0203002 A1 6/2023 Speerschneider et al.

FOREIGN PATENT DOCUMENTS

JP 2009520018 A 5/2009
JP 2010527974 A 8/2010
JP 2010535733 A 11/2010
JP 2010536818 A 12/2010
JP 2013503126 A 1/2013
JP 2013512272 A 4/2013
JP 2014506583 A 3/2014
JP 2014532640 A 12/2014
JP 2016514118 A 5/2016
WO 1998000401 A1 1/1998
WO 2000061569 A1 10/2000
WO 2001032178 A1 5/2001
WO 2001098267 A1 12/2001
WO 2002000651 A2 1/2002
WO 2002046187 A1 6/2002
WO 2003084948 A1 10/2003
WO 2004072075 A1 8/2004
WO 2005012716 A1 2/2005
WO 2005051916 A1 6/2005
WO 2005068427 A1 7/2005
WO 2006019768 A1 2/2006
WO 2007039264 A1 4/2007
WO 2007050980 A2 5/2007
WO 2007072150 A2 6/2007
WO 2007106469 A2 9/2007
WO 2008012623 A1 1/2008
WO 2008139484 A2 11/2008
WO 2009019163 A1 2/2009
WO 2009024502 A1 2/2009
WO 2009056520 A1 5/2009
WO 2009062319 A1 5/2009
WO 2009072643 A1 6/2009
WO 2012075232 A1 6/2012
WO 2012129562 A2 9/2012
WO 2012173214 A1 12/2012
WO 2013064983 A1 5/2013
WO 2013115163 A1 8/2013
WO 2013182612 A1 12/2013
WO 2014140310 A1 9/2014
WO 2016210403 A1 12/2016
WO 2017040545 A1 3/2017
WO 2018152286 A1 8/2018
WO 2018152293 A1 8/2018
WO 2019079540 A1 4/2019
WO 2022093904 A1 5/2022
WO 2023077049 A1 5/2023

OTHER PUBLICATIONS

Ascherio. The Lancet, 2016, 15, 1257-1272 (Year: 2016).*
Alstadhaug. Pain Reports, 2017, 2 e612, 1-5 (Year: 2017).*
Diener. The Lancet, 2015, 14, 1010-1022 (Year: 2015).*
Notice of Allowance issued Nov. 15, 2018 in U.S. Appl. No. 15/252,112 (138851.01801).
Notice of Allowance for U.S. Continuation U.S. Appl. No. 16/286,700 dated May 2, 2022.
Notice of Allowance for U.S. Appl. No. 16/486,541 dated Feb. 8, 2023.
Notice of Allowance for U.S. Appl. No. 16/486,541 dated Oct. 31, 2022.
Notice of Allowance, dated Aug. 23, 2021, issued in U.S. Appl. No. 16/486,539 (138851.001901).
Notice of Allowance-Corrected for U.S. Appl. No. 16/486,541 dated Nov. 21, 2022.
Offermanns et al., "Ga15 and Ga16 Couple a Wide Variety of Receptors to Phospholipase C", Journal Bilogical Chemistry (1995) vol. 270, No. 25, Issue of Jun. 23, pp. 15175-15180.
Peppin et al., "Delta opioid agonists: a concise update on poteential therapeutic applications", Journal of Clinical Pharmacy and Therapeutics, Inc., 40: 155-166 (2015).
Pradhan et al., "The delta opioid receptor: an evolving target for the treatment of brain disorders", Trends Pharmacol Sci. (2011) 32(10): 581-590.
Pubchem Compound Summary for CID 123379529 National Center for Biotechnology Information (2017).
Pubchem Compound Summary for CID 23146852 , National Center for Biotechnology Information (2007).
Pubchem Compound Summary for CID 67131456, U.S. National Library of Medicine 2012 pp. 1-13.
PubChem Compound Summary for CID 76849249 U.S. National Library of of Medicine (2014).
Pubchem—CID 10359344 Create Date Oct. 25, 2006, p. 3.
Rajewski, et al. "Pharmaceutical Applications of Cyclodextrins. 2. In Vivo Drug Delivery", Journal of Pharmaceutical Sciences (1996) vol. 85, No. 11, pp. 1142-1169.
Sakya et al., "Syntheses of 4-azepanes and heteroaromatic-fused azepines", Tetrahedron Letters (2012) 43, pp. 723-725.
Sanberg et al., "The Catalepsy Test: Its Ups and Downs", Behavioral Neuroscience (1988) vol. 102, No. 5, 748-759.
Saudek et al., "A Preliminary trial of the programmable implantable medication system for insulin delivery", New Englande Journal of Medicine, (1989) vol. 321, No. 9, pp. 574-579.
Smolen et al., "Drug Product Design and Performance", 1984, Wiley, article "Controlled Drug Bioavailability"; (vol. 1) by Smolen, VF and Ball, L (eds); https://doi.org/10.1002/jps.2600740735; p. 297.
Tuthill et al., "Azepinone as a conformational constraint in the design of k-opioid receptor agonists", Boorganic & Medicinal Chemistry Letters 14: pp. 5693-5697 (2004).
Vilpoux et al., "Differential effects of chronic antidepressant treatments on m- and d-opioid receptors in rat brain," European Journal of Pharmacology (2002) 443:85-93.
Zaveri et al., "Designing bifunctional NOP receptor-mu opioid receptor ligands from NOP receptor-selective scaffolds. Part I." Bioorganic & Medicinal Chemistry Letters, vol. 23, Issue 11, Jun. 1, 2013, pp. 3308-3313; https://doi.org/10.1016/j.bmcl.2013.03.101.
Calderon et al., "Probes for Narcotic Receptor Mediated Phenomena," J. Med. Chem. 1994, 37, pp. 2125-2128.
Dixon, Annual Review Pharmacol Toxicol, vol. 20, 1980, pp. 441; Ann. Rev. Pharmacol. Toxicol, 1980, 20:441-62, "Efficient Analysis of Experimental Observations".
Dunam et al., "Possible Involvement of Opioidergic and Serotonergic Mechanisms in Antinocipeptive Effect of Paroxetine in Acute Pain", J Pharmacol Sci 94, 161-165 (2004).
During et al., "Controlled Release of Dopamine from a Polymeric Brain Implant: In Vivo Characterization", Ann. Neurol. (1989) 25:351-356.
Elitzin VI, "Development of a new synthesis for the large-scale preparation of triple reuptake inhibitor (-)-GSK1360707" Organic Process Research and Development, 2010, 14(4), 912-917.
Engelstoft et al., "Synthesis and 5HT Modulating Activity of Stereoisomers of 3-Phenoxymethyl-4-phenylpiperidines," Acta Chemica Scandinavica, 1996, vol. 50, No. 2, pp. 164-169.
European Search Report (Partial) for European Patent Application No. 22161847.3 dated Sep. 27, 2022.
European Search Report for European Patent Application No. 16842832.4 dated Jun. 7, 2019.
European Search Report for European Patent Application No. 18753604.0 dated Aug. 3, 2020.
European Search Report for European Patent Application No. 18754875.5 dated Jul. 1, 2020.
Ex Parte Quayle Office Action for U.S. Appl. No. 16/486,541 dated Aug. 5, 2022.
Felley-Bosco, et al., "Constitutive Expression of Inducible Nitric Oxide Synthase in Human Bronchial Epithelial Cells Induces c-fos

(56) References Cited

OTHER PUBLICATIONS and Stimulates the cGMP Pathway", American Journal of Respiratory Cell and Molecular Biology (1994) vol. 11 pp. 160-164.
Final Office Action for U.S. Continuation U.S. Appl. No. 16/286,700 dated Sep. 15, 2021.
Final Office Action for U.S. Appl. No. 16/486,541 dated Oct. 12, 2021.
Final Office Action, dated Apr. 29, 2021, issued in U.S. Appl. No. 16/486,539 (138851.001901).
Fujimori et al., "Design, synthesis and biological evaluation of a novel series of peripheral-selective noradrenaline reuptake inhibitor," Bioorg. Med. Chem. (2015) 23: 5000-5014.
Goodson, Medical Applications of Controlled Release, vol. 2, 1984, pp. 115-138.
Groarke et al., Visualization of Agonist-induced Association and Trafficking of Green Fluorescent Protein-tagged Forms of Both b-Arrestin-1 and the Thyrotropin-releasing Hormone Receptor-1, J. of Biological Chemistry (1999)vol. 274, No. 33, pp. 23263-23269.
Homan et al., "Structural and Functional Analysis of G Protein-Coupled Receptor Kinase Inhibition by Paroxetine and a Rationally Designed Analog," Molecular Pharmacology (2014); 85(2): 237-248.
Howard et al., "Intracerebral drug delivery in rats with lesion-induced memory deficits", J Neurosurg (1989) 71:105-112.
Hudzik et al., "Preclinical Pharmacology of AZD2327: A Highly Selective Agonist of the—Opioid Receptor", JPET 338:195-204, (2011).
Humphries et al., "ADDP and ps-PPh3, an efficient Mitsunobu Protocol for the Preparation of Pyridine Ether PPAR Agonists," Beilstein Journal of Organic Chemistry, 2006, 2(21), pp. 1-5.
International Preliminary Report on Patentability for PCT/2016/049526 dated Mar. 6, 2018.
International Preliminary Report on Patentability for PCT/2018/018303 dated Aug. 20, 2019.
International Preliminary Report on Patentability for PCT/2018/018312 dated Aug. 20, 2019.
International Preliminary Report on Patentability for PCT/US2021/056764 dated May 2, 2023.
International Search Report and Written Opinion for International PCT Application No. PCT/CN2021/127727 dated Jul. 27, 2022.
International Search Report and Written Opinion for International PCT Application No. PCT/US2016/049526 dated Jan. 13, 2017.
International Search Report and Written Opinion for International PCT Application No. PCT/US2018/018303 dated May 24, 2018.
International Search Report and Written Opinion for International PCT Application No. PCT/US2018/018312 dated Apr. 24, 2018.
International Search Report and Written Opinion for International PCT Application No. PCT/US2021/056764 dated Jan. 26, 2022.
International Search Report and Written Opinion for International PCT Application No. PCT/US2022/078850 dated Mar. 13, 2023.
Journigan et al. Designing bifuncional NOP receptor-mu opioid receptor ligands from NOP-receptor selective scaffolds. Part 11, Bioorg Med Chem, 2014, 2508-2516, 22(8).
Kristoffersen et al., "Simultaneous Determination of Citalopram, Fluoxetine, Paroxetine and Their Metabolites in Plasma and Whole Blood by High-Performance Liquid Chromatography with Ultraviolet and Fluorescence Detection," Journal of Chromatography, 1999, vol. 734, No. 2, pp. 229-246.
Kroeger et al., "Constitutive and Agonist-dependent Homo-oligomerization of the Thyrotropin-releasing Hormone Receptor", Journal of Biological Chemistry (2001) vol. 276, No. 16, Issue of Apr. 20, pp. 12736-12743.
LaBuda CJ, "Pharmacological evaluation of the selective spinal nerve ligation model of neuropalhic pain in the rat", Journal of Neuroscience Methods, 2005, 144, 175-18.
Langer "New Methods of Drug Delivery", Science, (1990)vol. 249; pp. 1527-1533.
Langer et al., "Chemical and Physical Structure of Polymers as Carriers for Controlled Release of Bioactive Agents: A Review", JMS—Rev. Macromol. Chem. Phys., C23(1), 61-126 (1983).
Lee et al., "Asymmetric Syntheses of 4,5,6- and 3,4,5,6-Substituted Azepanes by a Highly Diastereoselective and Enantioselective Lithiation—Conjugate Addition Sequence", (J. Am. Chem. Soc. 2006) 128, pp. 2178-2179.
Levy et al., "Inhibition of Calcification of Bioprosthetic Heart Valves by Local Controlled—Release Diphosphonate", Science, New Series, vol. 228, No. 4696 pp. 190-192 (1985).
Mabrouk et al., "Stimulation of delta opioid receptors located in substantia nigra reticulata but not globus pallidus or striatum restores motor activity in 6-hydroxydopamine lesioned rats: new insights into the role of delta receptors in parkinsonism", J. Neurochem. (2008) 107, 1647-1659.
Marti et al., "Blockade of nociceptin/orphanin FQ transmission in rat substantia nigra reverses haloperidol-induced akinesia and normalizes nigral glutamate release", J. Neurochem. (2004) 91, 1501-1504.
Mayo Clinic, "Parkinson's disease", https://www.mayoclinic.org/disease conditions/parkinsons disease/symptoms causes/syc 20376055 (2021).
Misteli et al., "Applications of the green fluorescent protein incell biology and biotechnology". Nature Biotechnology (1997) Vo. 15 pp. 961-964.
Non-Final Office Action for U.S. Appl. No. 16/486,541 dated Apr. 29, 2021.
Nonfinal Office Action issued Feb. 2, 2021 in U.S. Appl. No. 16/286,700 (138851.01821).
Nonfinal Office Action issued Apr. 18, 2018 in U.S. Appl. No. 15/252,112 (138851.01801).
Nonfinal Office Action issued Mar. 4, 2021 in U.S. Appl. No. 16/486,539 (138851.01901).
Notice of Allowability (Corrected) for U.S. Continuation U.S. Appl. No. 16/286,700 dated Sep. 14, 2022.
Notice of Allowability for U.S. Continuation U.S. Appl. No. 16/286,700 dated Jun. 1, 2022.

* cited by examiner

FIG. 6
The compound of Formula I in free base form
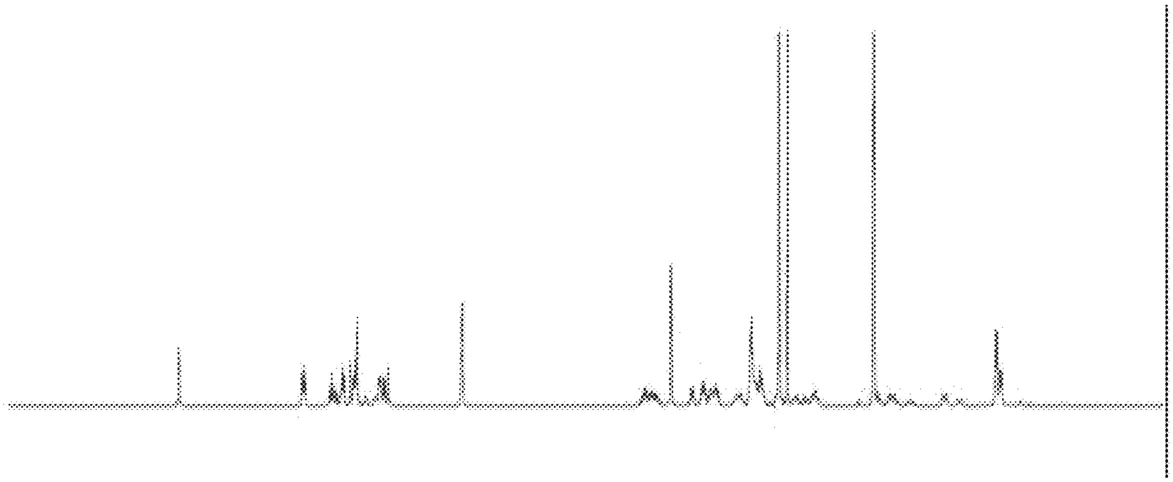
The compound of Formula I in HCl salt form
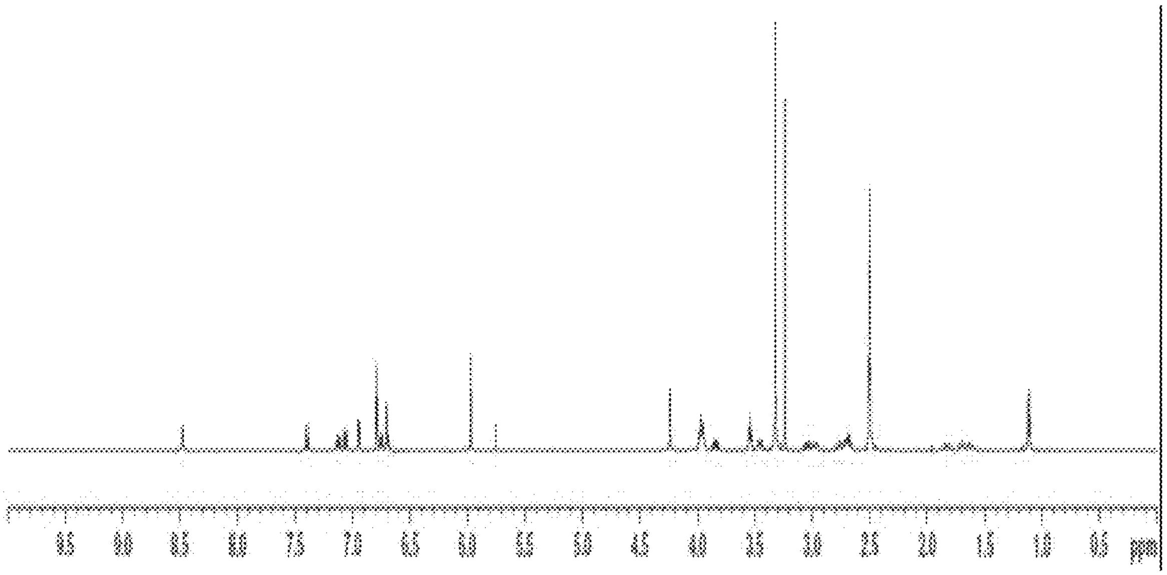

Integration Results

| No. | Peak Name | [illegible] | Retention Time min | Rel. Ret. Time | [illegible] | [illegible] | [illegible] | [illegible] |
|---|---|---|---|---|---|---|---|---|
| 1 | Unknown | TRUE | 6.908 | 0.67 | 0.725 | 14.149 | 0.41 | n.a. |
| 2 | Unknown | TRUE | 7.296 | 0.71 | 0.147 | 2.903 | 0.08 | n.a. |
| 3 | Unknown | TRUE | 7.675 | 0.74 | 0.090 | 0.875 | 0.05 | n.a. |
| 4 | Unknown | TRUE | 9.150 | 0.89 | 0.145 | 2.357 | 0.08 | n.a. |
| 5 | Unknown | TRUE | 9.387 | 0.91 | 0.127 | 2.273 | 0.07 | n.a. |
| 6 | Unknown | TRUE | 9.862 | 0.96 | 0.110 | 1.991 | 0.06 | n.a. |
| 7 | TRV250 | TRUE | 10.305 | 1.00 | 174.330 | 1987.189 | 98.73 | n.a. |
| 8 | Unknown | TRUE | 10.825 | 1.05 | 0.096 | 1.083 | 0.06 | n.a. |
| 9 | Unknown | TRUE | 11.318 | 1.10 | 0.234 | 3.635 | 0.13 | n.a. |
| 10 | Unknown | TRUE | 11.627 | 1.13 | 0.217 | 3.084 | 0.12 | n.a. |
| 11 | Unknown | TRUE | 11.927 | 1.16 | 0.113 | 1.409 | 0.06 | n.a. |
| 12 | Unknown | TRUE | 13.380 | 1.30 | 0.087 | 1.563 | 0.05 | n.a. |
| 13 | Unknown | TRUE | 14.030 | 1.36 | 0.153 | 3.590 | 0.09 | n.a. |
| Total | | | | | 176.679 | 2026.010 | 100.00 | 0.00 |

FIG.11
Material isolated from tBME:heptane 50:50 v/v%:
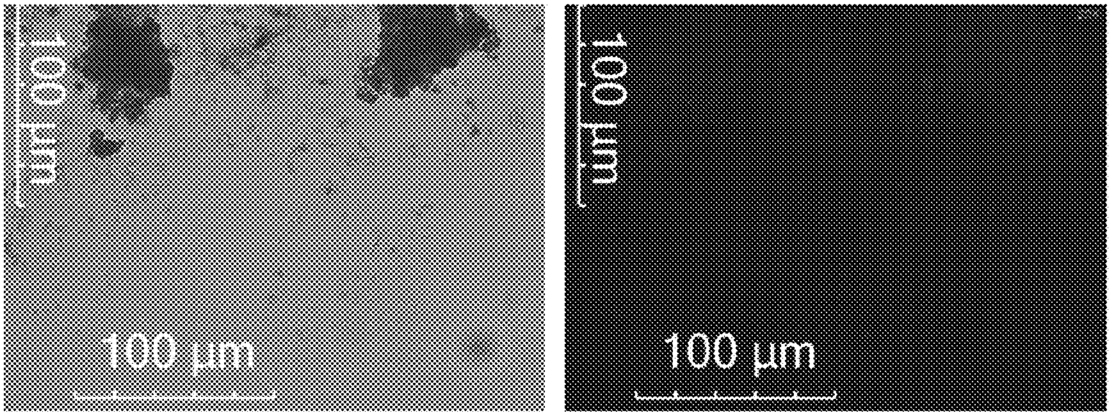
Material isolated from MEK:heptane 20:80 v/v%:
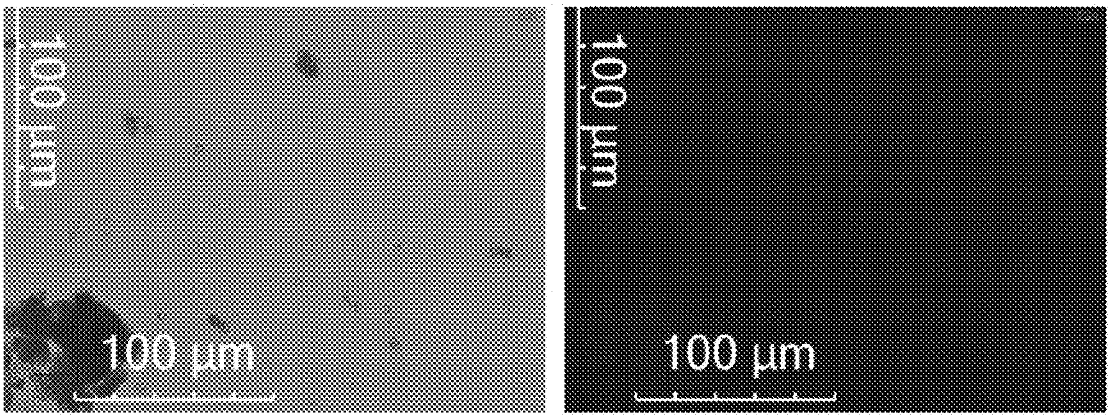

Material isolated from tBME:heptane 50:50 v/v%:

FIG. 14

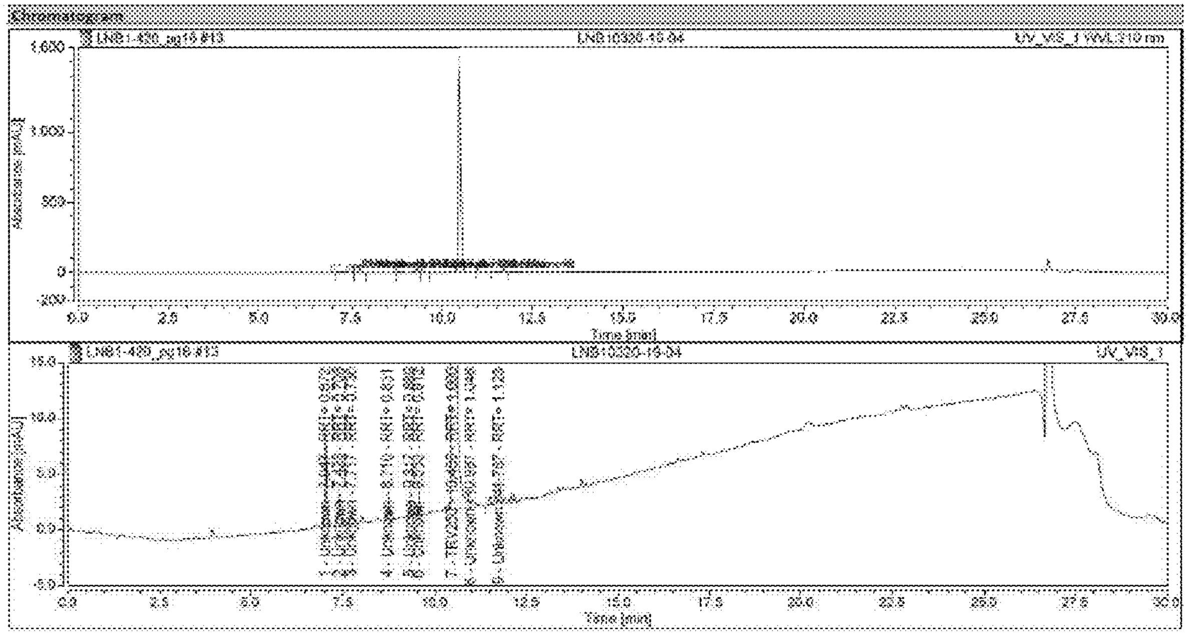

Integration Results

| No. | Peak Name | Manipulated? | Retention Time min | Rel. Ret. Time | Area mAU*min | Height mAU | Rel.Area % | Amount |
|---|---|---|---|---|---|---|---|---|
| 1 | Unknown | FALSE | 7.047 | 0.67 | 0.417 | 8.083 | 0.36 | n.a. |
| 2 | Unknown | FALSE | 7.423 | 0.71 | 0.152 | 2.834 | 0.13 | n.a. |
| 3 | Unknown | FALSE | 7.717 | 0.74 | 0.087 | 0.894 | 0.08 | n.a. |
| 4 | Unknown | FALSE | 8.710 | 0.83 | 0.062 | 1.155 | 0.05 | n.a. |
| 5 | Unknown | FALSE | 9.317 | 0.89 | 0.086 | 1.647 | 0.07 | n.a. |
| 6 | Unknown | FALSE | 9.553 | 0.91 | 0.090 | 1.589 | 0.08 | n.a. |
| 7 | TRV250 | FALSE | 10.480 | 1.00 | 114.193 | 1491.175 | 99.02 | n.a. |
| 8 | Unknown | FALSE | 10.987 | 1.05 | 0.121 | 0.735 | 0.11 | n.a. |
| 9 | Unknown | FALSE | 11.767 | 1.12 | 0.118 | 1.894 | 0.10 | n.a. |
| Total: | | | | | 115.318 | 1509.585 | 100.00 | 0.00 |

Impurity Table

Sample : LNB10320-19-04

| Peak Name | Retention time min | | RRT | | Mean RRT | Rel Area % | | Mean Rel Area % |
|---|---|---|---|---|---|---|---|---|
| Unknown | 7.05 | 7.04 | 0.67 | 0.67 | 0.672 | 0.36 | 0.36 | 0.36 |
| Unknown | 7.42 | 7.43 | 0.71 | 0.71 | 0.708 | 0.13 | 0.13 | 0.13 |
| Unknown | 7.72 | 7.72 | 0.74 | 0.74 | 0.736 | 0.08 | 0.08 | 0.07 |
| Unknown | 8.71 | 8.71 | 0.83 | 0.83 | 0.831 | 0.05 | 0.05 | 0.05 |
| Unknown | 9.32 | 9.32 | 0.89 | 0.89 | 0.889 | 0.07 | 0.08 | 0.08 |
| Unknown | 9.55 | 9.55 | 0.91 | 0.91 | 0.912 | 0.08 | 0.08 | 0.08 |
| Unknown | 10.98 | 10.98 | 1.05 | 1.05 | 1.048 | 0.11 | 0.06 | 0.06 |
| Unknown | n.a. | 11.07 | n.a. | 1.06 | n.a. | n.a. | 0.07 | 0.07 |
| Unknown | 11.77 | 11.78 | 1.12 | 1.12 | 1.123 | 0.10 | 0.11 | 0.10 |

| | |
|---|---|
| Total impurities | 1.03 |
| Reported Purity | 98.97 |

FIG. 15

Chromatogram

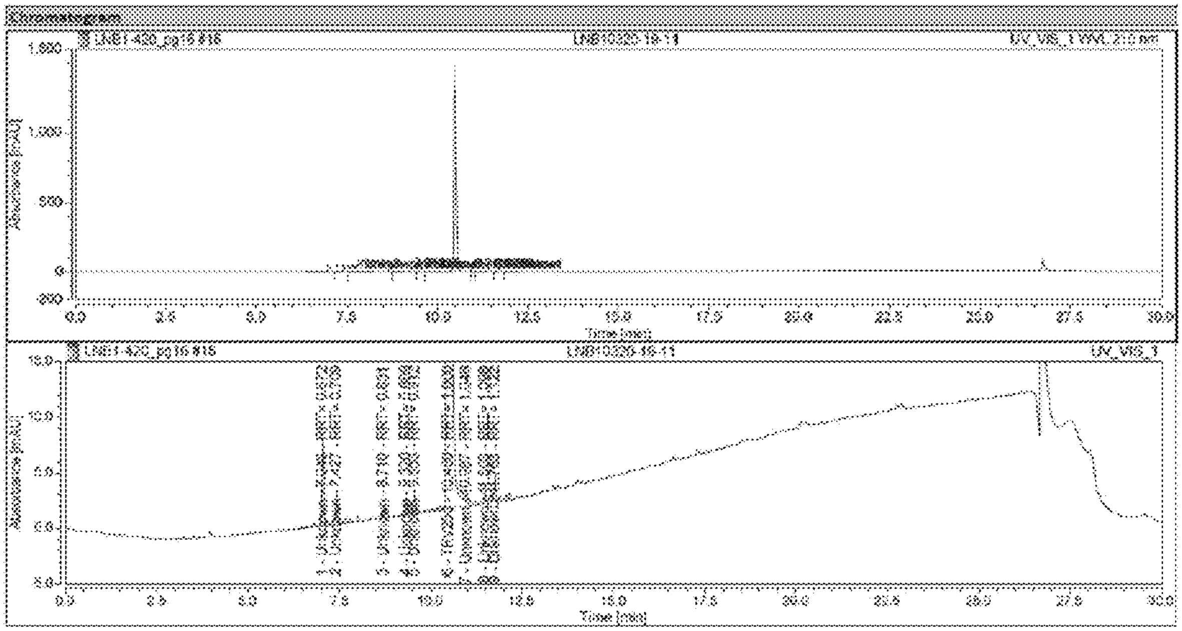

Integration Results

| No. | Peak Name | Manual Int.? | Retention Time min | Rel. Ret. Time | Area mAU*min | Height mAU | Rel. Area % | Amount |
|---|---|---|---|---|---|---|---|---|
| 1 | Unknown | FALSE | 7.043 | 0.67 | 0.357 | 7.003 | 0.34 | n.a |
| 2 | Unknown | FALSE | 7.427 | 0.71 | 0.116 | 2.136 | 0.11 | n.a |
| 3 | Unknown | FALSE | 8.710 | 0.83 | 0.055 | 1.093 | 0.05 | n.a |
| 4 | Unknown | FALSE | 9.320 | 0.89 | 0.088 | 1.520 | 0.08 | n.a |
| 5 | Unknown | FALSE | 9.553 | 0.91 | 0.095 | 1.600 | 0.09 | n.a |
| 6 | TRV250 | FALSE | 10.480 | 1.00 | 105.902 | 1400.520 | 99.07 | n.a |
| 7 | Unknown | FALSE | 10.987 | 1.05 | 0.091 | 1.569 | 0.08 | n.a |
| 8 | Unknown | FALSE | 11.503 | 1.10 | 0.073 | 1.129 | 0.07 | n.a |
| 9 | Unknown | FALSE | 11.793 | 1.12 | 0.100 | 1.194 | 0.09 | n.a |
| Total: | | | | | 106.892 | 1428.518 | 100.00 | 0.00 |

Impurity Table

Sample : LNB10320-19-11

| Peak Name | Retention time min | | RRT | | Mean RRT | Rel.Area % | | Mean Rel.Area % |
|---|---|---|---|---|---|---|---|---|
| Unknown | 7.04 | 7.04 | 0.67 | 0.67 | 0.673 | 0.34 | 0.34 | 0.34 |
| Unknown | 7.43 | 7.43 | 0.71 | 0.71 | 0.709 | 0.11 | 0.11 | 0.11 |
| Unknown | 8.71 | n.a | 0.83 | n.a | 0.831 | 0.05 | n.r | 0.05 |
| Unknown | 9.32 | 9.32 | 0.89 | 0.89 | 0.889 | 0.08 | 0.09 | 0.08 |
| Unknown | 9.55 | 9.55 | 0.91 | 0.91 | 0.912 | 0.09 | 0.09 | 0.09 |
| Unknown | 10.98 | 10.99 | 1.05 | 1.05 | 1.048 | 0.09 | 0.08 | 0.08 |
| Unknown | 11.50 | 11.50 | 1.10 | 1.10 | 1.098 | 0.07 | 0.06 | 0.06 |
| Unknown | 11.78 | 11.78 | 1.12 | 1.12 | 1.122 | 0.09 | 0.08 | 0.09 |

| | |
|---|---|
| Total impurities | 0.91 |
| Reported Purity | 99.09 |

FIG. 32

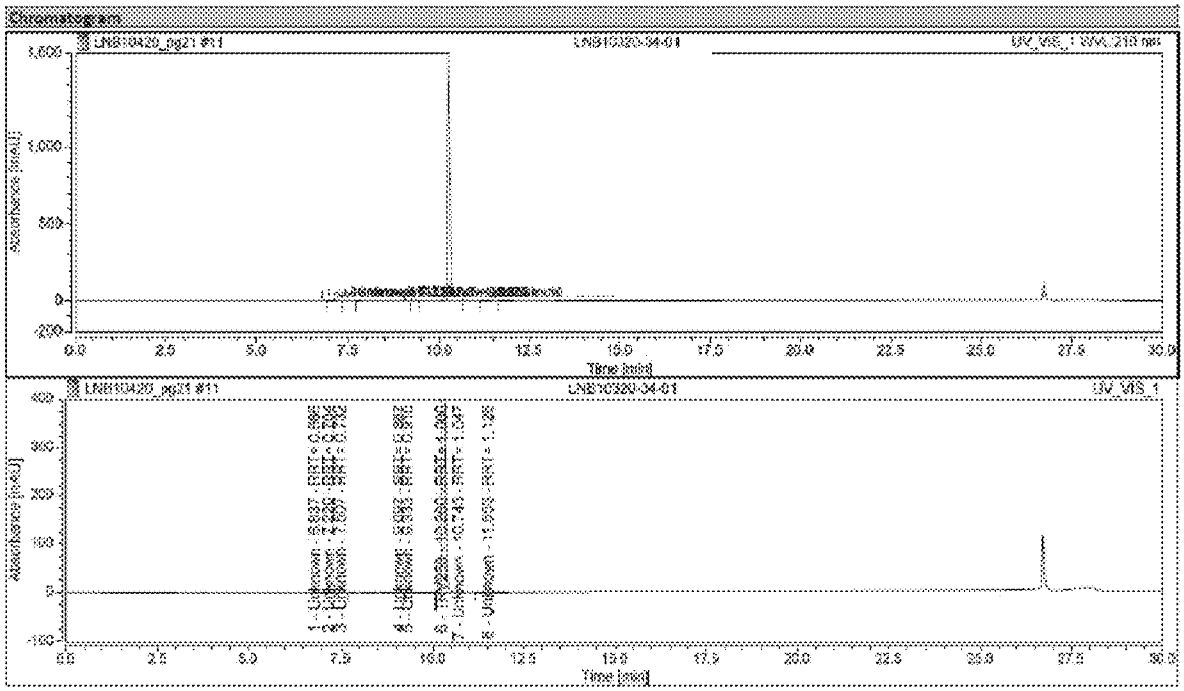

Integration Results

| No. | Peak Name | Manipulated? | Retention Time min | Rel. Ret. Time | Area mAU*min | Height mAU | Rel. Area % | Amount |
|---|---|---|---|---|---|---|---|---|
| 1 | Unknown | FALSE | 6.837 | 0.67 | 0.353 | 6.164 | 0.27 | n.a. |
| 2 | Unknown | FALSE | 7.220 | 0.70 | 0.213 | 3.680 | 0.17 | n.a. |
| 3 | Unknown | FALSE | 7.507 | 0.73 | 0.093 | 0.962 | 0.07 | n.a. |
| 4 | Unknown | FALSE | 9.097 | 0.89 | 0.082 | 1.346 | 0.06 | n.a. |
| 5 | Unknown | FALSE | 9.333 | 0.91 | 0.080 | 1.364 | 0.06 | n.a. |
| 6 | TRV250 | FALSE | 10.260 | 1.00 | 126.971 | 1817.848 | 99.22 | n.a. |
| 7 | Unknown | FALSE | 10.743 | 1.05 | 0.096 | 0.528 | 0.07 | n.a. |
| 8 | Unknown | FALSE | 11.553 | 1.13 | 0.094 | 1.385 | 0.07 | n.a. |
| Total | | | | | 127.970 | 1832.918 | 100.00 | 0.00 |

Impurity Table

Sample : LNB10320-34-01

| Peak Name | Retention time min | | RRT | | Mean RRT | Rel. Area % | | Mean Rel. Area % |
|---|---|---|---|---|---|---|---|---|
| Unknown | 6.84 | 6.84 | 0.67 | 0.67 | 0.666 | 0.27 | 0.27 | 0.27 |
| Unknown | 7.22 | 7.22 | 0.70 | 0.70 | 0.704 | 0.17 | 0.17 | 0.17 |
| Unknown | 7.51 | 7.51 | 0.73 | 0.73 | 0.732 | 0.07 | 0.08 | 0.07 |
| Unknown | 9.10 | 9.09 | 0.89 | 0.89 | 0.887 | 0.06 | 0.06 | 0.06 |
| Unknown | 9.33 | 9.33 | 0.91 | 0.91 | 0.910 | 0.06 | 0.07 | 0.06 |
| Unknown | 10.74 | 10.74 | 1.05 | 1.05 | 1.047 | 0.07 | 0.07 | 0.07 |
| Unknown | 11.55 | 11.56 | 1.13 | 1.13 | 1.126 | 0.07 | 0.07 | 0.07 |

| | |
|---|---|
| Total impurities | 0.78 |
| Reported Purity | 99.22 |

FIG. 33

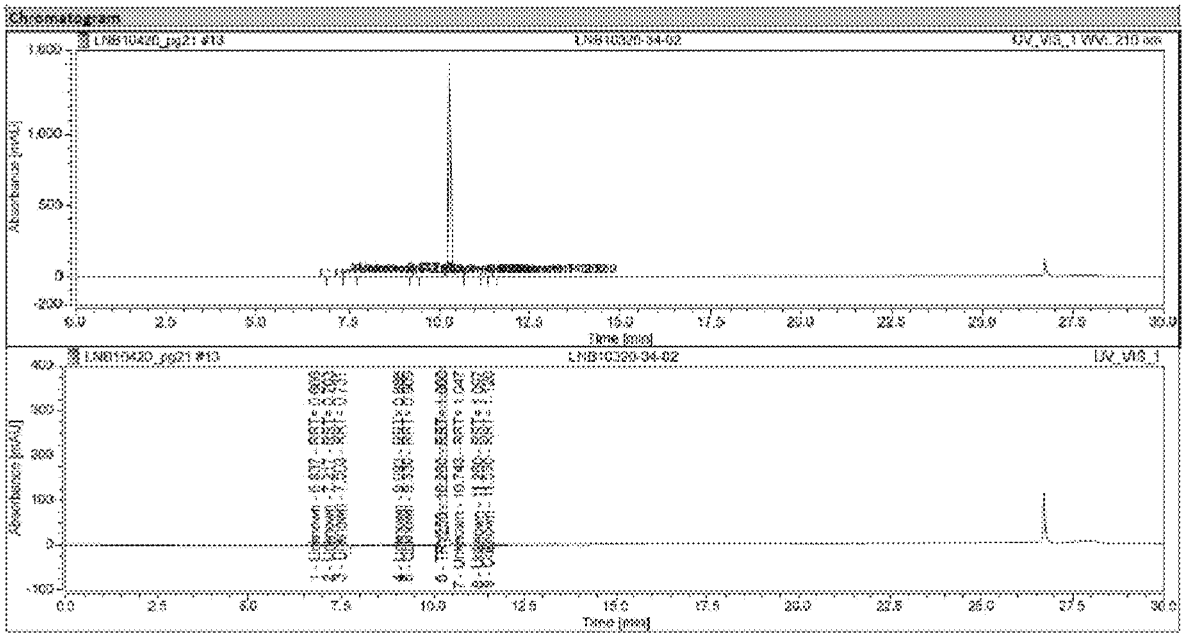

Integration Results

| No. | Peak Name | [illegible] | Retention Time min | [illegible] | Area mAU*min | Height mAU | Rel.Area % | [illegible] |
|---|---|---|---|---|---|---|---|---|
| 1 | Unknown | FALSE | 6.837 | 0.67 | 0.477 | 3.384 | 0.39 | n.a. |
| 2 | Unknown | FALSE | 7.217 | 0.70 | 0.175 | 2.938 | 0.14 | n.a. |
| 3 | Unknown | FALSE | 7.503 | 0.73 | 0.070 | 0.568 | 0.06 | n.a. |
| 4 | Unknown | FALSE | 9.083 | 0.88 | 0.093 | 1.539 | 0.08 | n.a. |
| 5 | Unknown | FALSE | 9.330 | 0.91 | 0.090 | 1.631 | 0.07 | n.a. |
| 6 | TRV250 | FALSE | 10.380 | 1.00 | 121.143 | 1488.835 | 99.02 | n.a. |
| 7 | Unknown | FALSE | 10.743 | 1.05 | 0.111 | 2.873 | 0.09 | n.a. |
| 8 | Unknown | FALSE | 11.293 | 1.10 | 0.077 | 1.160 | 0.06 | n.a. |
| 9 | Unknown | FALSE | 11.563 | 1.13 | 0.105 | 1.545 | 0.09 | n.a. |
| Total: | | | | | 123.342 | 1497.398 | 100.00 | 0.00 |

Impurity Table

Sample : LNB10320-34-02

| Peak Name | Retention Time min | | RRT | | Mean RRT | Rel.Area % | | Mean Rel.Area % |
|---|---|---|---|---|---|---|---|---|
| Unknown | 6.84 | 6.84 | 0.67 | 0.67 | 0.666 | 0.39 | 0.39 | 0.39 |
| Unknown | 7.22 | 7.22 | 0.70 | 0.70 | 0.703 | 0.14 | 0.14 | 0.14 |
| Unknown | 7.52 | 7.50 | 0.73 | 0.73 | 0.731 | 0.06 | 0.05 | 0.05 |
| Unknown | 9.08 | 9.09 | 0.89 | 0.89 | 0.886 | 0.08 | 0.08 | 0.08 |
| Unknown | 9.33 | 9.33 | 0.91 | 0.91 | 0.909 | 0.07 | 0.07 | 0.07 |
| Unknown | 10.74 | 10.73 | 1.05 | 1.05 | 1.047 | 0.09 | 0.08 | 0.09 |
| Unknown | 11.26 | 11.27 | 1.10 | 1.10 | 1.097 | 0.06 | 0.06 | 0.06 |
| Unknown | 11.55 | 11.58 | 1.13 | 1.13 | 1.128 | 0.09 | 0.09 | 0.09 |

| | |
|---|---|
| Total impurities | 0.97 |
| Reported Purity | 99.03 |

FIG. 34

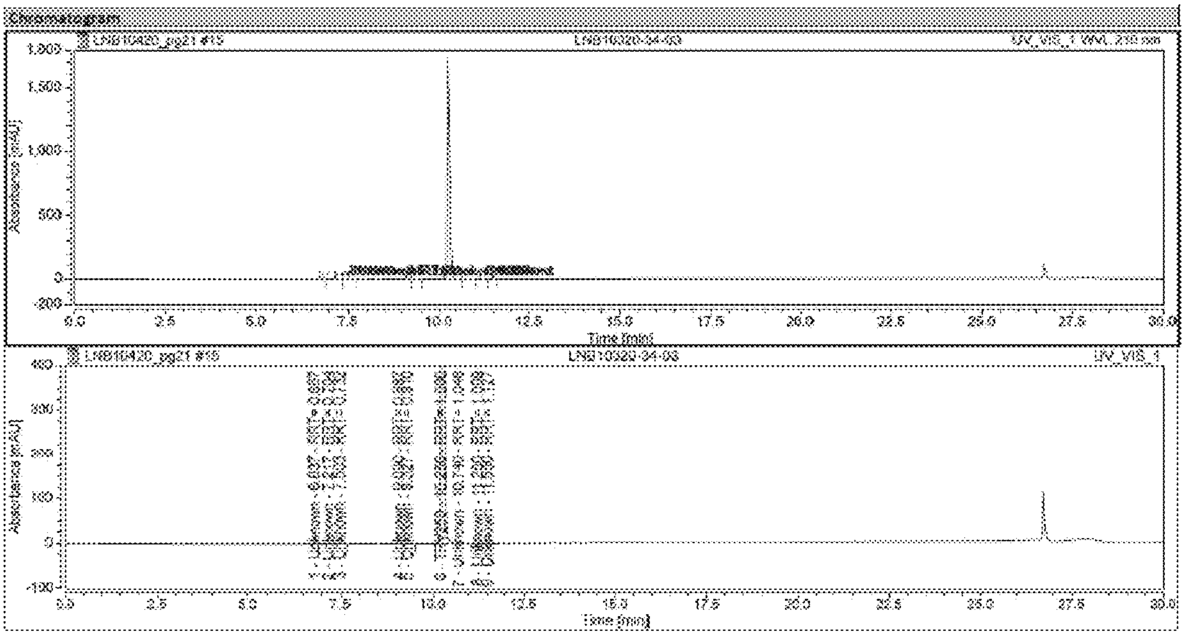

Integration Results

| No. | Peak Name | [illegible] | Retention Time min | Rel. Ret. Time | Area mAU*min | Height mAU | Rel. Area % | [illegible] |
|---|---|---|---|---|---|---|---|---|
| 1 | Unknown | FALSE | 6.837 | 0.67 | 0.607 | 10.733 | 0.42 | n.a. |
| 2 | Unknown | FALSE | 7.217 | 0.70 | 0.164 | 2.780 | 0.11 | n.a. |
| 3 | Unknown | FALSE | 7.500 | 0.73 | 0.081 | 0.637 | 0.06 | n.a. |
| 4 | Unknown | FALSE | 9.090 | 0.89 | 0.123 | 1.812 | 0.08 | n.a. |
| 5 | Unknown | FALSE | 9.327 | 0.91 | 0.127 | 1.624 | 0.09 | n.a. |
| 6 | TKV250 | FALSE | 10.250 | 1.00 | 144.390 | 1678.467 | 98.90 | n.a. |
| 7 | Unknown | FALSE | 10.740 | 1.05 | 0.242 | 3.048 | 0.17 | n.a. |
| 8 | Unknown | FALSE | 11.260 | 1.10 | 0.142 | 2.318 | 0.10 | n.a. |
| 9 | Unknown | FALSE | 11.550 | 1.13 | 0.112 | 1.785 | 0.08 | n.a. |
| Total: | | | | | 145.985 | 1703.251 | 100.00 | 0.00 |

Impurity Table

Sample : LNB10320-34-03

| Peak Name | Retention time min | | RRT | | Mean RRT | Rel Area % | | Mean Re Area % |
|---|---|---|---|---|---|---|---|---|
| Unknown | 6.84 | 6.84 | 0.67 | 0.67 | 0.667 | 0.42 | 0.42 | 0.42 |
| Unknown | 7.22 | 7.22 | 0.70 | 0.70 | 0.704 | 0.11 | 0.11 | 0.11 |
| Unknown | 7.50 | 7.50 | 0.73 | 0.73 | 0.732 | 0.08 | 0.08 | 0.08 |
| Unknown | 9.09 | 9.09 | 0.89 | 0.89 | 0.887 | 0.08 | 0.08 | 0.08 |
| Unknown | 9.33 | 9.33 | 0.91 | 0.91 | 0.910 | 0.09 | 0.08 | 0.09 |
| Unknown | 10.74 | 10.74 | 1.05 | 1.05 | 1.048 | 0.17 | 0.18 | 0.17 |
| Unknown | 11.26 | 11.26 | 1.10 | 1.10 | 1.099 | 0.10 | 0.10 | 0.10 |
| Unknown | 11.55 | 11.55 | 1.13 | 1.13 | 1.127 | 0.08 | 0.08 | 0.08 |

| | |
|---|---|
| Total impurities | 1.11 |
| Reported Purity | 98.89 |

FIG.35
XRPD Analysis (Wet Solids):
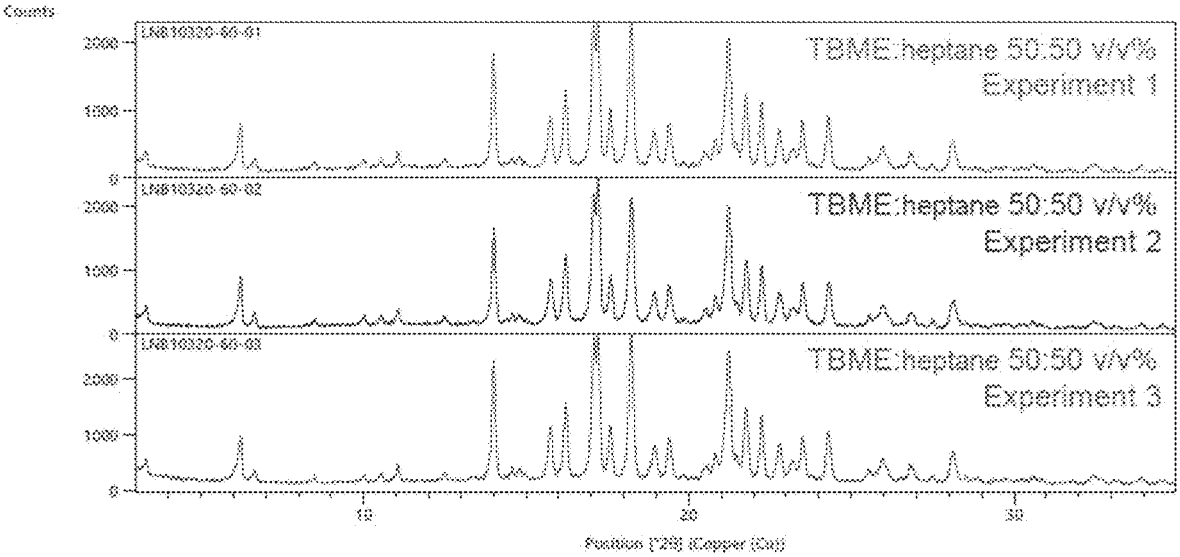
XRPD Analysis (Dry Solids):
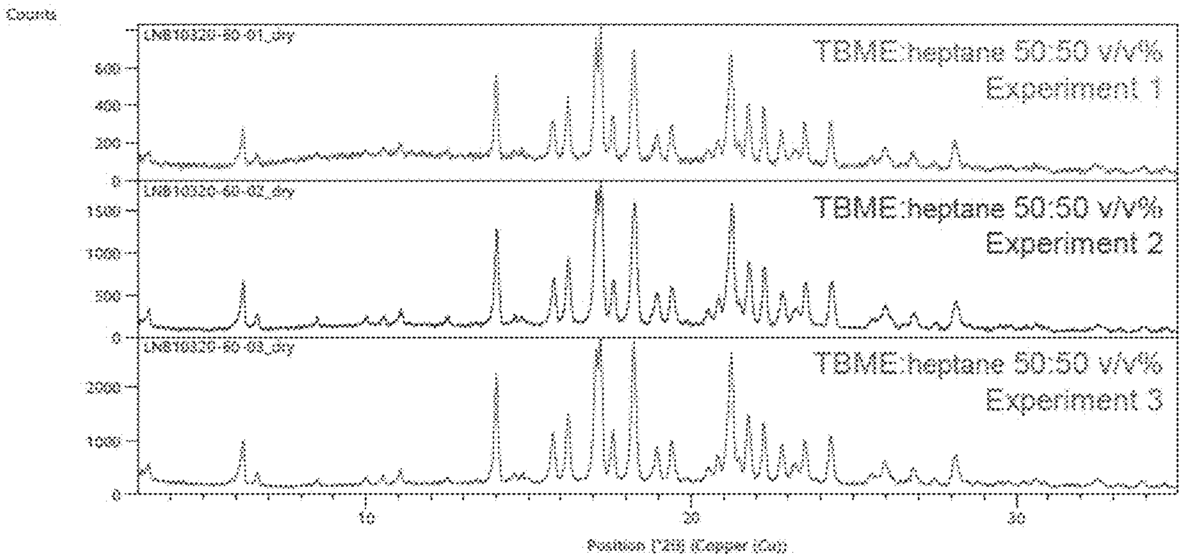

FIG.37

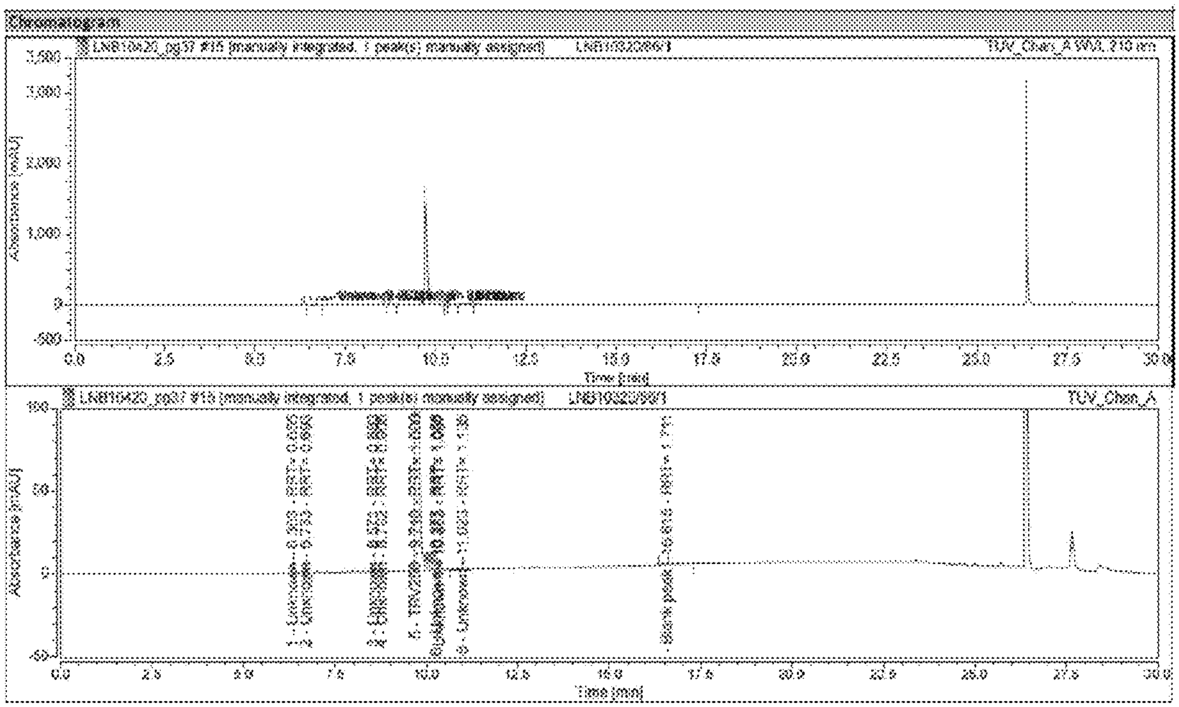

Integration Results

| No. | Peak Name | Manual peak? | Retention Time min | Rel. Ret. Time | Area mAU*min | Height mAU | Rel. Area % | Amount ng/mL |
|---|---|---|---|---|---|---|---|---|
| 1 | Unknown | TRUE | 6.323 | 0.65 | 0.288 | 6.210 | 0.28 | n.a. |
| 2 | Unknown | TRUE | 6.723 | 0.69 | 0.140 | 2.737 | 0.12 | n.a. |
| 3 | Unknown | TRUE | 8.571 | 0.88 | 0.066 | 1.276 | 0.06 | n.a. |
| 4 | Unknown | TRUE | 8.760 | 0.91 | 0.073 | 1.467 | 0.07 | n.a. |
| 5 | TRV250 | TRUE | 9.718 | 1.00 | 111.670 | 1508.629 | 99.37 | n.a. |
| 6 | Unknown | TRUE | 10.277 | 1.06 | 0.076 | 0.836 | 0.07 | n.a. |
| 8 | Unknown | TRUE | 11.023 | 1.14 | 0.064 | 1.041 | 0.06 | n.a. |
| Total: | | | | | 112.378 | 1522.135 | 100.00 | 0.00 |

Impurity Table

Sample : LNB10320/86/1

| Peak Name | Retention time min | | RRT | | Mean RRT | Rel Area % | | Mean Rel Area % |
|---|---|---|---|---|---|---|---|---|
| Unknown | 6.36 | 6.33 | 0.66 | 0.65 | 0.655 | 0.28 | 0.28 | 0.28 |
| Unknown | 6.73 | 6.70 | 0.69 | 0.69 | 0.693 | 0.12 | 0.12 | 0.12 |
| Unknown | 8.57 | 8.54 | 0.88 | 0.88 | 0.883 | 0.06 | 0.06 | 0.06 |
| Unknown | 8.79 | 8.76 | 0.91 | 0.91 | 0.905 | 0.07 | 0.05 | 0.06 |
| Unknown | 10.35 | 10.25 | 1.06 | 1.06 | 1.058 | 0.07 | 0.08 | 0.07 |
| Unknown | 11.02 | 10.99 | 1.14 | 1.14 | 1.135 | 0.08 | 0.08 | 0.08 |

| | |
|---|---|
| Total Impurities | 0.62 |
| Reported Purity | 99.38 |

FIG.38
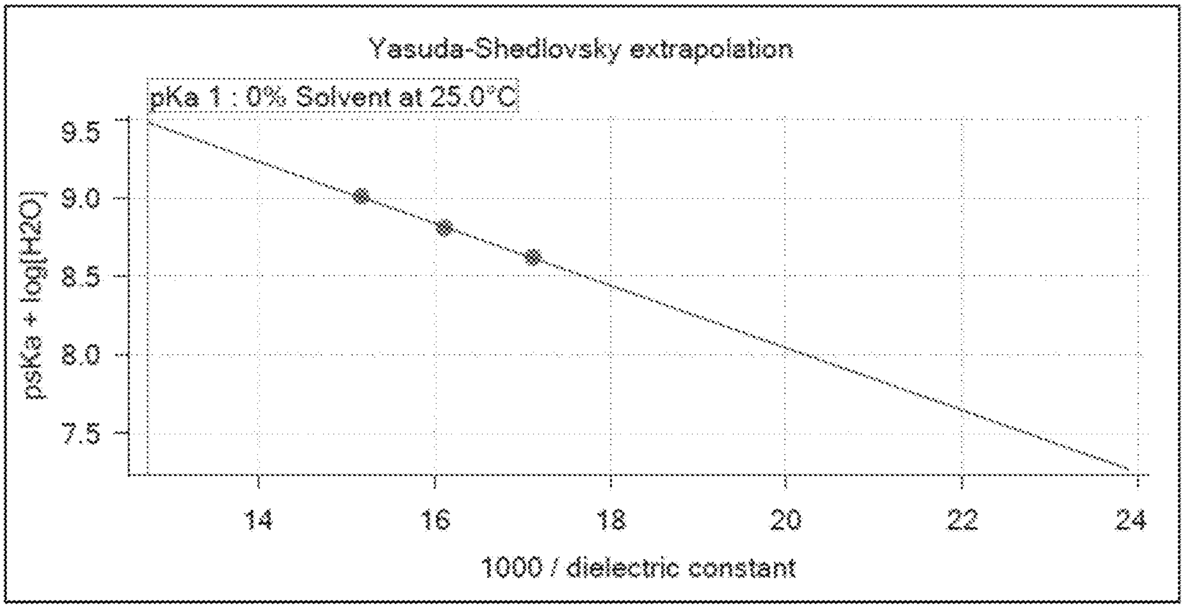
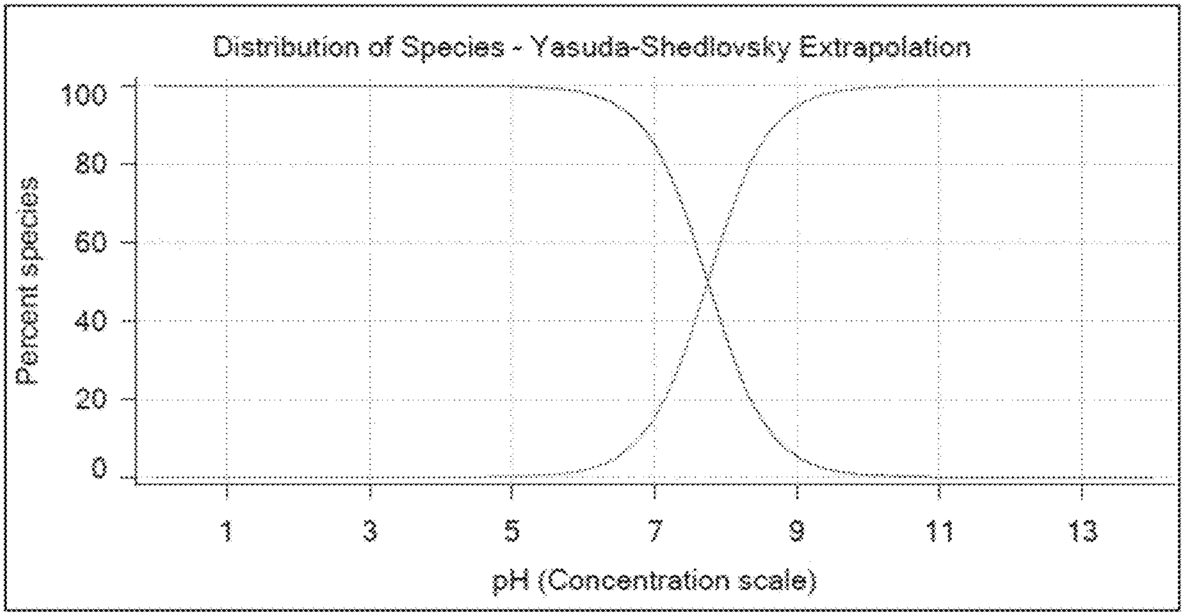

FIG.40
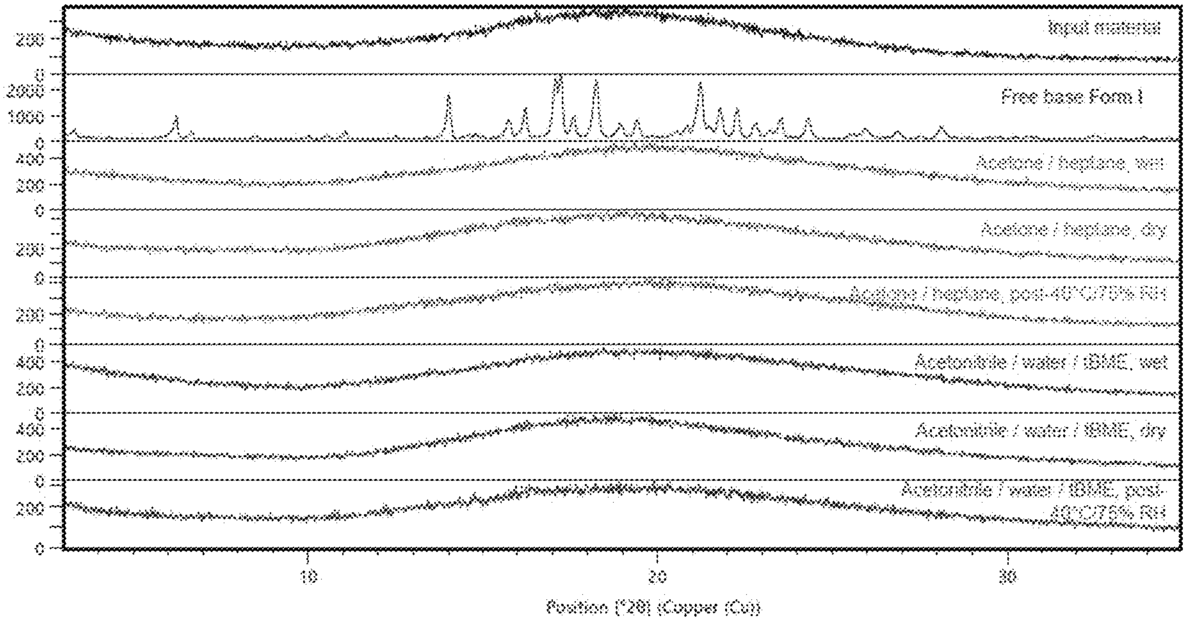
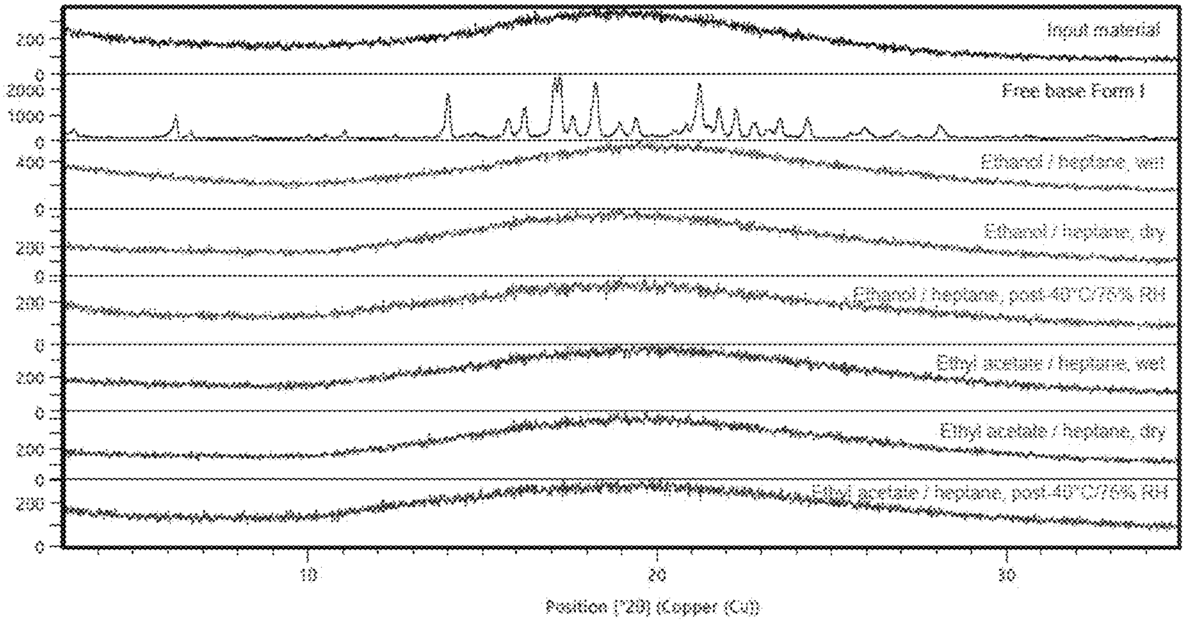

FIG.43

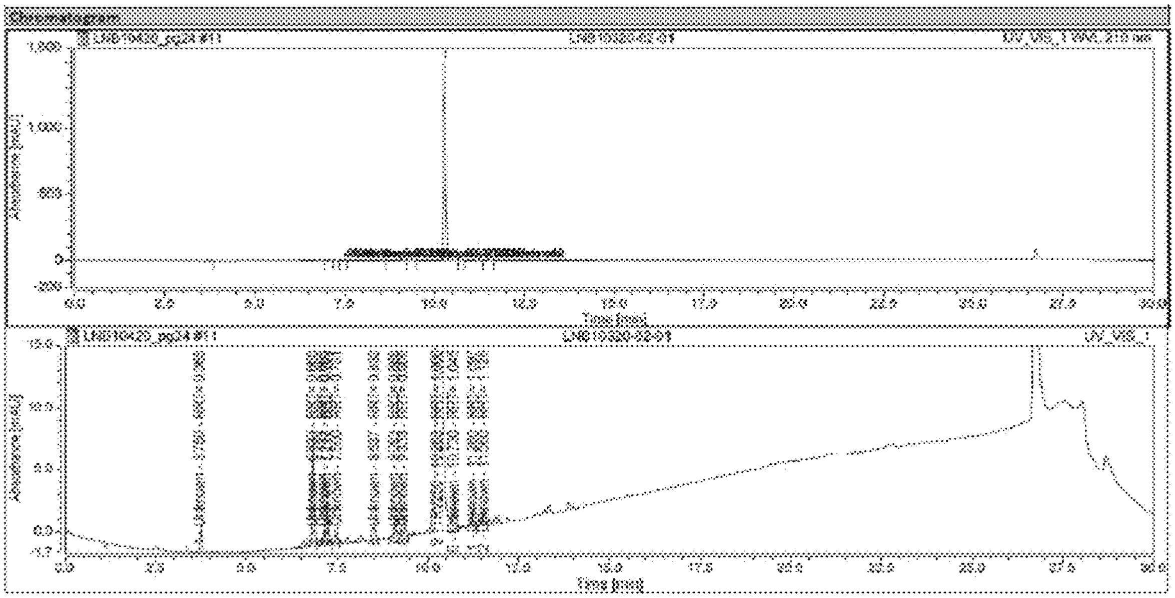

Integration Results

| No. | Peak Name | [illegible] | Retention Time min | Rel. Ret. Time | Area | Height | Rel. Area % | [illegible] |
|---|---|---|---|---|---|---|---|---|
| 1 | Unknown | FALSE | 3.752 | 0.37 | 0.131 | 1.679 | 0.08 | n.a. |
| 2 | Unknown | FALSE | 6.833 | 0.67 | 0.537 | 6.423 | 0.43 | n.a. |
| 3 | Unknown | FALSE | 7.131 | 0.70 | 0.071 | 1.368 | 0.06 | n.a. |
| 4 | Unknown | FALSE | 7.217 | 0.70 | 0.206 | 3.502 | 0.16 | n.a. |
| 5 | Unknown | FALSE | 7.502 | 0.73 | 0.069 | 0.987 | 0.05 | n.a. |
| 6 | Unknown | FALSE | 8.537 | 0.83 | 0.066 | 0.987 | 0.05 | n.a. |
| 7 | Unknown | FALSE | 9.083 | 0.89 | 0.107 | 1.585 | 0.08 | n.a. |
| 8 | Unknown | FALSE | 9.333 | 0.91 | 0.118 | 1.765 | 0.09 | n.a. |
| 9 | TRV250 | FALSE | 10.263 | 1.00 | 124.190 | 1502.022 | 98.63 | n.a. |
| 10 | Unknown | FALSE | 10.730 | 1.05 | 0.216 | 2.849 | 0.17 | n.a. |
| 11 | Unknown | FALSE | 11.260 | 1.10 | 0.132 | 2.031 | 0.11 | n.a. |
| 12 | Unknown | FALSE | 11.580 | 1.13 | 0.097 | 1.364 | 0.08 | n.a. |
| Total | | | | | 125.898 | 1530.380 | 100.00 | 0.00 |

Impurity Table

Sample : LN810320-62-01

| Peak Name | Retention time min | | RRT | | Mean RRT | Rel Area % | | Mean Rel Area % |
|---|---|---|---|---|---|---|---|---|
| Unknown | 3.75 | 3.76 | 0.37 | 0.37 | 0.365 | 0.08 | 0.08 | 0.08 |
| Unknown | 6.83 | 6.84 | 0.67 | 0.67 | 0.666 | 0.43 | 0.42 | 0.43 |
| Unknown | 7.13 | 7.14 | 0.70 | 0.70 | 0.695 | 0.06 | 0.06 | 0.06 |
| Unknown | 7.22 | 7.22 | 0.70 | 0.70 | 0.703 | 0.16 | 0.16 | 0.16 |
| Unknown | 7.50 | n.a | 0.73 | n.a | 0.731 | 0.05 | n.r | 0.05 |
| Unknown | 8.54 | 8.54 | 0.83 | 0.83 | 0.832 | 0.05 | 0.05 | 0.05 |
| Unknown | 9.09 | 9.10 | 0.89 | 0.89 | 0.886 | 0.08 | 0.09 | 0.09 |
| Unknown | 9.33 | 9.34 | 0.91 | 0.91 | 0.909 | 0.09 | 0.10 | 0.10 |
| Unknown | 10.73 | 10.73 | 1.05 | 1.05 | 1.045 | 0.17 | 0.17 | 0.17 |
| Unknown | 11.28 | 11.28 | 1.10 | 1.10 | 1.097 | 0.11 | 0.11 | 0.11 |
| Unknown | 11.56 | 11.58 | 1.13 | 1.13 | 1.125 | 0.08 | 0.08 | 0.08 |
| | | | | | | Total impurities | | 1.38 |
| | | | | | | Reported Purity | | 98.62 |

FIG.44

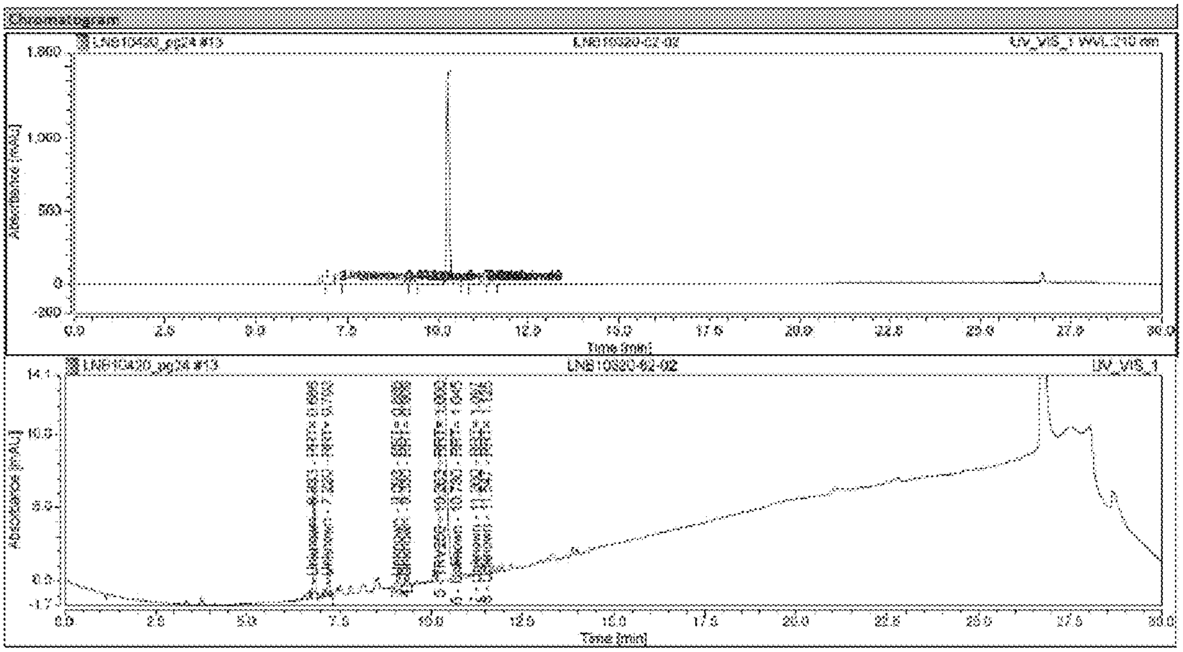

Integration Results

| No. | Peak Name | Manipulated? | Retention Time min | Rel. Ret. Time | Area mAU*min | Height mAU | Rel.Area % | Amount |
|---|---|---|---|---|---|---|---|---|
| 1 | Unknown | FALSE | 6.823 | 0.67 | 0.434 | 7.605 | 0.38 | n.a. |
| 2 | Unknown | FALSE | 7.220 | 0.70 | 0.142 | 2.421 | 0.12 | n.a. |
| 3 | Unknown | FALSE | 9.090 | 0.89 | 0.096 | 1.382 | 0.08 | n.a. |
| 4 | Unknown | FALSE | 9.330 | 0.91 | 0.101 | 1.519 | 0.09 | n.a. |
| 5 | TRV250 | FALSE | 10.283 | 1.00 | 114.406 | 1405.895 | 99.01 | n.a. |
| 6 | Unknown | FALSE | 10.730 | 1.05 | 0.163 | 2.054 | 0.14 | n.a. |
| 7 | Unknown | FALSE | 11.280 | 1.10 | 0.107 | 1.617 | 0.09 | n.a. |
| 8 | Unknown | FALSE | 11.547 | 1.13 | 0.101 | 1.139 | 0.09 | n.a. |
| Total: | | | | | 115.548 | 1423.635 | 100.00 | 0.00 |

Impurity Table

Sample : LNB10320-62-02

| Peak Name | Retention time min | | RRT | | Mean RRT | Rel.Area % | | Mean Rel.Area % |
|---|---|---|---|---|---|---|---|---|
| Unknown | 6.83 | 6.84 | 0.67 | 0.67 | 0.665 | 0.38 | 0.38 | 0.38 |
| Unknown | 7.22 | 7.22 | 0.70 | 0.70 | 0.703 | 0.12 | 0.12 | 0.12 |
| Unknown | 9.09 | 9.10 | 0.89 | 0.89 | 0.885 | 0.08 | 0.08 | 0.08 |
| Unknown | 9.33 | 9.33 | 0.91 | 0.91 | 0.909 | 0.09 | 0.09 | 0.09 |
| Unknown | 10.73 | 10.73 | 1.05 | 1.05 | 1.045 | 0.14 | 0.13 | 0.14 |
| Unknown | 11.35 | 11.28 | 1.10 | 1.10 | 1.097 | 0.09 | 0.09 | 0.09 |
| Unknown | 11.55 | 11.58 | 1.13 | 1.13 | 1.125 | 0.09 | 0.09 | 0.09 |

| | |
|---|---|
| Total impurities | 0.99 |
| Reported Purity | 99.01 |

FIG.46

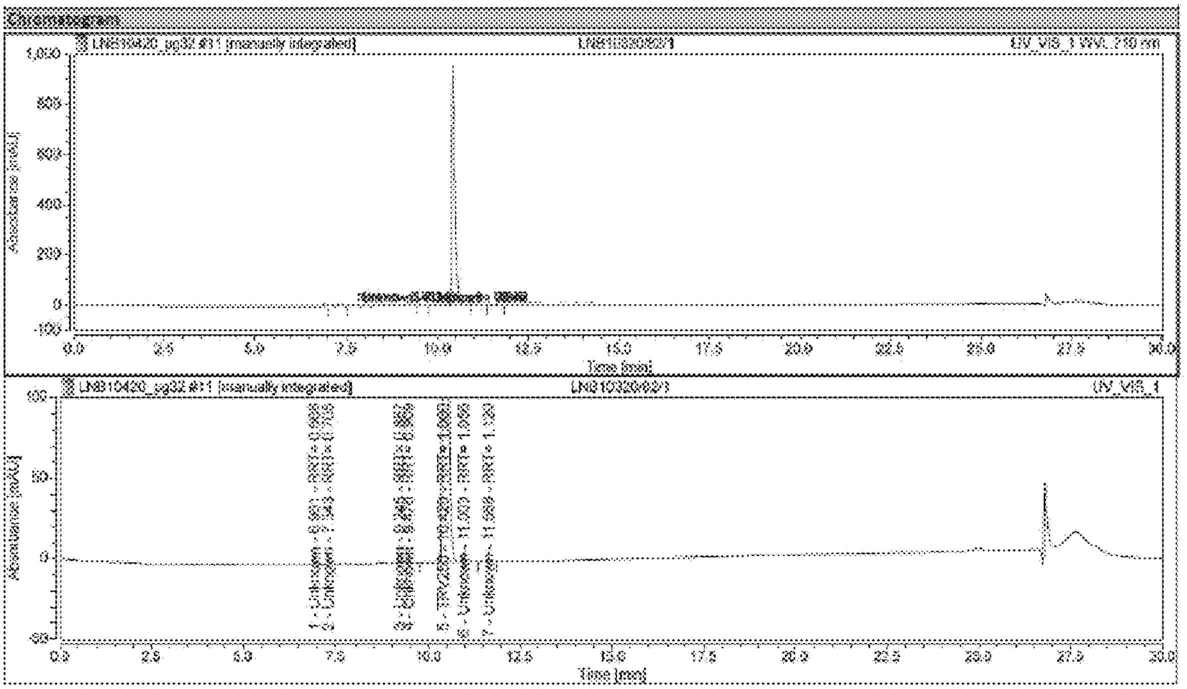

Integration Results

| No. | Peak Name | Manipulated? | Retention Time min | Rel. Ret. Time | Area mAU*min | Height mAU | Rel. Area % | Amount n.a. |
|---|---|---|---|---|---|---|---|---|
| 1 | Unknown | TRUE | 6.961 | 0.67 | 0.180 | 2.631 | 0.18 | n.a. |
| 2 | Unknown | TRUE | 7.343 | 0.70 | 0.102 | 1.362 | 0.10 | n.a. |
| 3 | Unknown | TRUE | 9.245 | 0.89 | 0.064 | 0.785 | 0.06 | n.a. |
| 4 | Unknown | TRUE | 9.476 | 0.91 | 0.076 | 0.860 | 0.07 | n.a. |
| 5 | TRV250 | TRUE | 10.420 | 1.00 | 101.864 | 917.423 | 99.44 | n.a. |
| 6 | Unknown | TRUE | 11.063 | 1.06 | 0.067 | 0.430 | 0.07 | n.a. |
| 7 | Unknown | TRUE | 11.658 | 1.12 | 0.079 | 0.626 | 0.08 | n.a. |
| Total: | | | | | 102.441 | 924.216 | 100.00 | 0.00 |

Impurity Table

Sample : LNB10320/62/1

| Peak Name | Retention time (min) | | RRT | | Mean RRT | Rel. Area % | | Mean Rel. Area % |
|---|---|---|---|---|---|---|---|---|
| Unknown | 6.96 | 6.96 | 0.67 | 0.67 | 0.668 | 0.18 | 0.19 | 0.19 |
| Unknown | 7.34 | 7.34 | 0.70 | 0.70 | 0.705 | 0.10 | 0.10 | 0.10 |
| Unknown | 9.24 | 9.25 | 0.89 | 0.89 | 0.887 | 0.06 | 0.06 | 0.06 |
| Unknown | 9.48 | 9.48 | 0.91 | 0.91 | 0.909 | 0.07 | 0.07 | 0.07 |
| Unknown | 11.03 | 11.03 | 1.06 | 1.06 | 1.056 | 0.07 | 0.07 | 0.07 |
| Unknown | 11.67 | 11.67 | 1.12 | 1.12 | 1.120 | 0.08 | 0.07 | 0.07 |

| | |
|---|---|
| Total impurities | 0.57 |
| Reported Purity | 99.43 |

CRYSTALLINE AND AMORPHOUS FORMS OF A δ-OPIOID MODULATOR

CROSS-REFERENCE TO RELATED APPLICATIONS

The present application is a National Phase Entry of International Patent Application No. PCT/US2021/056764 filed Oct. 27, 2021, which claims priority to U.S. Provisional Application No. 63/106,202, filed Oct. 27, 2020, each of which is hereby incorporated by reference in its entirety.

FIELD

The present disclosure describes novel crystalline forms of a compound that acts as a δ-opioid effector, processes for preparing and precipitating amorphous and crystalline forms of the compound, and uses thereof.

BACKGROUND

U.S. Pat. No. 10,246,436 discloses compounds that act as GPCR modulator of GPCR receptors (e.g., delta opioid receptor (DOR)). For example, GPCR agonist causes activation of a heterotrimeric "G protein". Such activation leads to second messenger/down-stream signaling (e.g., via diacylglycerol, inositol-triphosphate, calcium, etc.) causing changes in physiological function (e.g., pain, migraines, headaches, depression, anxiety, and/or overactive bladder). One particular compound, disclosed in U.S. Pat. No. 10,246,436 is referred to therein as "(−)-6-{[(trans,trans)-4-[3-(2-methoxyethoxy)phenyl]-2-methyl-1-[2-(1H-pyrrol-1-yl) ethyl]piperi din-3-yl]methoxy}-2,3-dihydro-1H-isoindol-1-one", which has a formula of Formula I

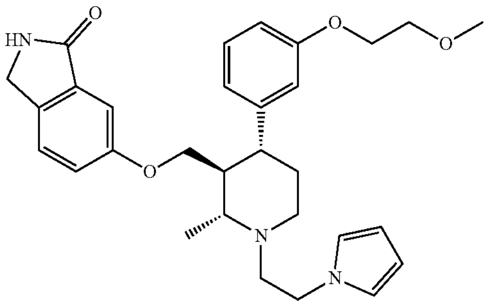

The compound of Formula I referred in U.S. Pat. No. 10,246,436 is a modulator of DOR. The compound of Formula I, the ability of the compound to effect G protein-mediated signaling or GPCR activity, or the absence of such signaling/activity, methods for preparation of the compound of Formula I, and other related compounds are disclosed in U.S. Pat. No. 10,246,436, the contents of which are incorporated herein by reference in their entirety.

There remains a need in the art for improved forms of the compound of Formula I with improved properties. There also remains a need in the art for improved processes for preparing the compound of the compound of Formula I.

SUMMARY

The present disclosure provides novel crystalline modifications of the compound of Formula I, processes for preparing the compound of Formula I, and optionally isolating such forms.

Surprisingly, the compound of the compound of Formula I can be crystallized in free base form and is superior in properties. Surprisingly, amorphous form of the compound of Formula I can be prepared, by precipitating the compound of Formula I in free base form. Crystalline forms of the compound of Formula I in free base form are distinguished from prior art by improved stability, processability and can also be used in pharmaceutical formulations.

In some embodiments, crystalline forms of the compound of Formula I in free base form are provided. In some embodiments, the crystalline form is Form I of the compound of Formula I in free base form (hereinafter the "crystalline Form I").

In some embodiments, the crystalline Form I is characterized by an X-ray powder diffraction pattern comprising a peak at about 18.3±0.5 degrees 2θ.

In some embodiments, the crystalline Form I is characterized by an X-ray powder diffraction pattern comprising a peak at about 17.1±0.5 degrees 2θ.

In some embodiments, the crystalline Form I is characterized by an X-ray powder diffraction pattern comprising a peak at about 17.3±0.5 degrees 2θ.

In some embodiments, the crystalline Form I is characterized by an X-ray powder diffraction pattern comprising a peak at about 21.2±0.5 degrees 2θ.

In some embodiments, the crystalline Form I is characterized by an X-ray powder diffraction pattern comprising a peak at about 14.0±0.5 degrees 2θ.

In some embodiments, the crystalline Form I is characterized by an X-ray powder diffraction pattern comprising peaks at about 18.3, and at about 17.1±0.5 degrees 2θ.

In some embodiments, the crystalline Form I is characterized by an X-ray powder diffraction pattern comprising peaks at about 17.1, and at about 17.3±0.5 degrees 2θ.

In some embodiments, the crystalline Form I is characterized by an X-ray powder diffraction pattern comprising peaks at about 17.3, and at about 21.2±0.5 degrees 2θ.

In some embodiments, the crystalline Form I is characterized by an X-ray powder diffraction pattern comprising peaks at about 21.2, and at about 17.1±0.5 degrees 2θ.

In some embodiments, the crystalline Form I is characterized by an X-ray powder diffraction pattern comprising peaks at about 21.2, and at about 14.0±0.5 degrees 2θ.

In some embodiments, the crystalline Form I is characterized by an X-ray powder diffraction pattern comprising peaks at about 21.2, at about 17.1, and at about 14.0±0.5 degrees 2θ.

In some embodiments, the crystalline Form I is characterized by an X-ray powder diffraction pattern comprising peaks at about 17.3, at about 18.3, and at about 21.2±0.5 degrees 2θ.

In some embodiments, the crystalline Form I is characterized by an X-ray powder diffraction pattern comprising peaks at about 18.3, at about 17.1, at about 17.3, at about 21.2, and at about 14.0±0.5 degrees 2θ.

In some embodiments, the crystalline Form I is characterized by an X-ray powder diffraction pattern comprising one or more peaks as shown in FIG. 16.

In some embodiments, the crystalline Form I is characterized by an X-ray powder diffraction pattern comprising one or more d-spacing values at about 6.3, at about 5.1, at about 5.2, at about 4.9, and at about 4.2±0.5 degrees angstroms.

In some embodiments, a pharmaceutical composition comprising a crystalline form of the compound of Formula I is provided.

In some embodiments, a pharmaceutical composition comprising the crystalline Form I of the compound of Formula I is provided.

In some embodiments, the pharmaceutical composition comprises Form I, further comprising an additional drug for the treatment of pain, migraine, headache, depression, Parkinson's disease, anxiety, overactive bladder, medication overuse headache, hyperalgesia, decreasing nociceptive sensitization, pain in an opioid exposed subject, PTSD and related disorders and conditions in or any combination thereof.

In some embodiments, a process for preparing a crystalline form of the compound of Formula I, comprising crystallizing the compound of Formula I to form the crystalline Form I and optionally isolating the crystalline Form I of the compound of Formula I is provided.

In some embodiments, a process for preparing the compound of Formula I, comprising precipitating the compound of Formula I and optionally isolating the compound of Formula I is provided.

In some embodiments, a pharmaceutical composition comprising the compound of Formula I prepared by precipitating the compound of Formula I is provided.

In some embodiments, a method of treating or preventing pain, migraine, headache, depression, Parkinson's disease, anxiety, overactive bladder, medication overuse headache, hyperalgesia, decreasing nociceptive sensitization, pain in an opioid exposed subject, PTSD and related disorders and conditions in or any combination thereof comprising administering to a patient in need thereof, a crystalline or an amorphous form of the compound of Formula I is provided.

The details of one or more embodiments are set forth in the description below. Other features, objects, and advantages of the present teachings will be apparent from the description of examples and also from the appending claims.

BRIEF DESCRIPTION OF THE DRAWINGS

FIG. 6 shows Proton Nuclear Magnetic Resonance Spectroscopy ($^1$H NMR) analysis of the amorphous form of the compound of Formula I in free base form and in HCl salt form.

FIG. 11 shows microscopy images of the material isolated from tBME:Heptane 50:50 v/v % and from MEK:Heptane 20:80 v/v %.

FIG. 14 shows HPLC chromatograms of the material isolated from tBME:Heptane 50:50 v/v %.

FIG. 15 shows HPLC chromatograms of the material isolated from MEK:Heptane 20:80 v/v %.

FIG. 32 shows HPLC chromatograms of the crystalline Form I prepared from tBME:Heptane 50:50 v/v %.

FIG. 33 shows HPLC chromatograms of the crystalline Form I prepared from MEK:Heptane 20:80 v/v %.

FIG. 34 shows HPLC chromatograms of the crystalline Form I prepared from THF:Heptane 22:78 v/v %.

FIG. 35 shows X-ray powder diffraction patterns of the solids directly isolated after anti-solvent addition (wet solids) and after drying under vacuum (dry solids) for different batches.

FIG. 37 shows HPLC chromatograms of the crystalline Form I from the scale-up in Example 3C.

FIG. 38 shows the Spectrometric (UV-metric) pKa result of the crystalline Form I from the scale-up in Example 3C: Yasuda-Shedlovsky extrapolation.

FIG. 40 and FIG. 41 show X-ray powder diffraction patterns of the HCl salt of the compound of Formula I directly isolated from various conditions in comparison with the free base Form I and the input material of the compound of Formula I.

FIG. 43 shows the HPLC chromatogram of the crystalline Form I after 14-days under ambient conditions.

FIG. 44 shows the HPLC chromatogram of the crystalline Form I after 14 days at 40° C./75% relative humidity.

FIG. 46 shows the HPLC chromatogram of the isolated material from the aqueous solubility studies.

DETAILED DESCRIPTION

Figure 1:
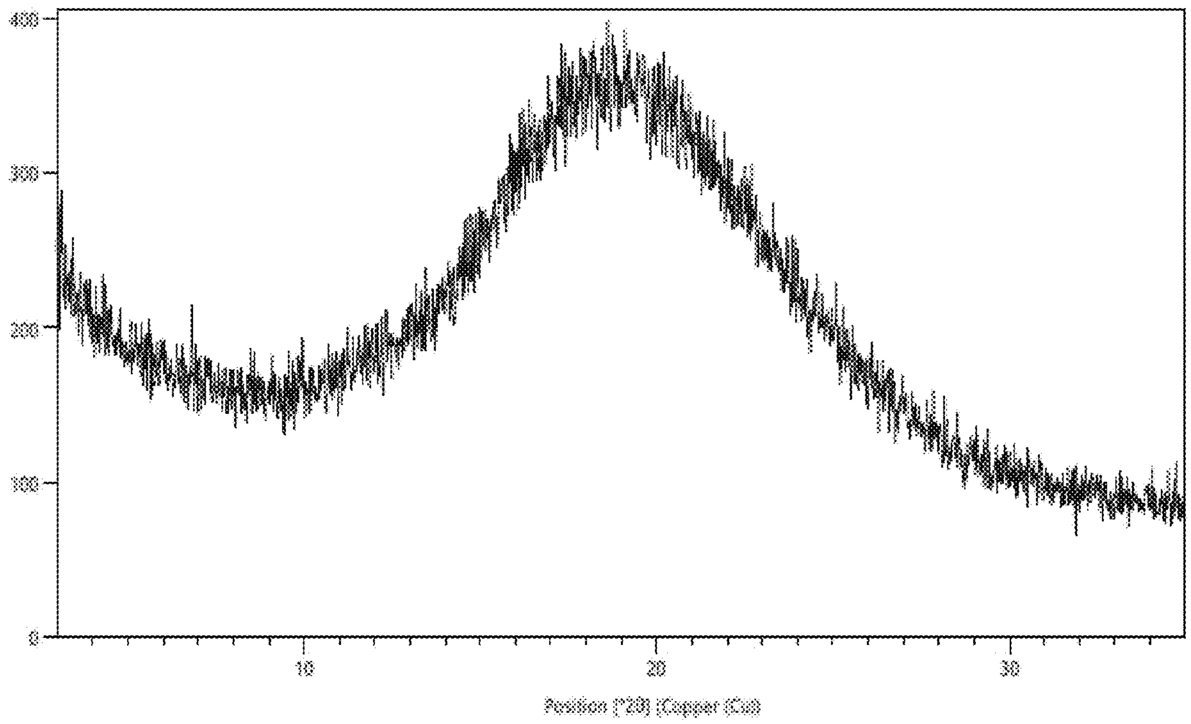
FIG. 1 shows X-ray powder diffraction pattern of the amorphous form of the compound of Formula I in free base form.
Figure 2:
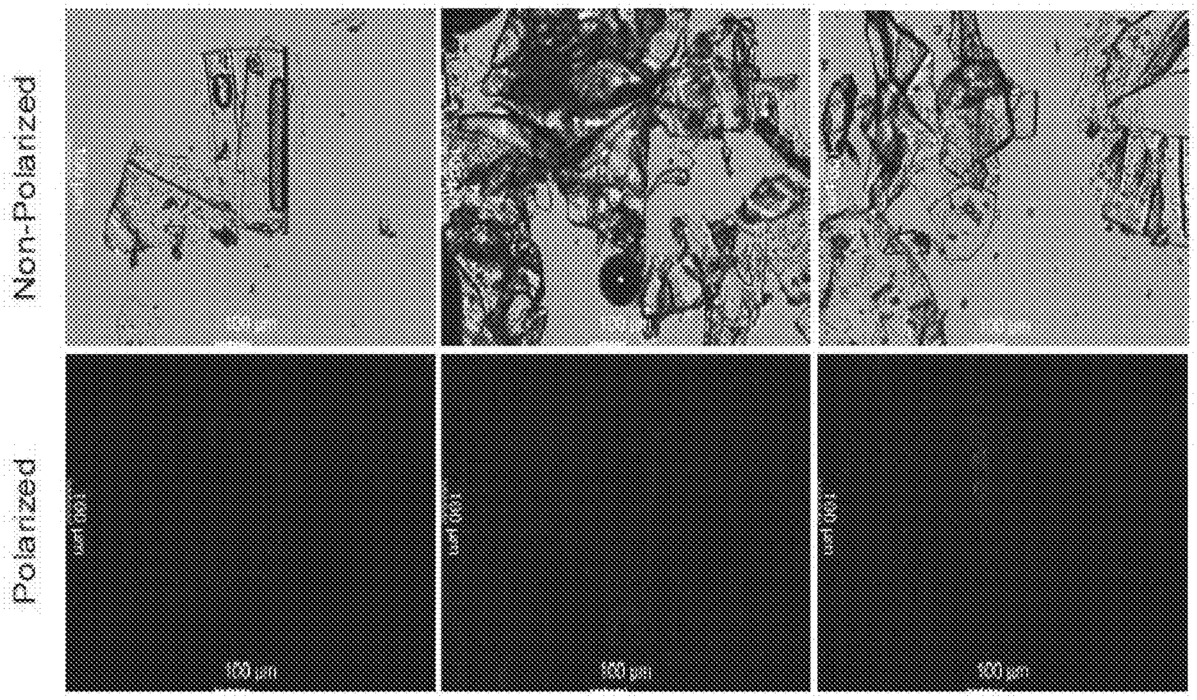
FIG. 2 shows microscopy images of the amorphous form of the compound of Formula I in free base form under both polarized and non-polarized light.

The term "salt" or "salts" may refer to any acid addition salts, including addition salts of free acids or addition salts of free bases. All of these salts (or other similar salts) may be prepared by conventional means. All such salts are acceptable provided that they are non-toxic and do not substantially interfere with the desired pharmacological activity.

The term "therapeutically effective amount" means the amount of a compound that, when administered to a mammal for treating a state, disorder or condition is sufficient to effect a treatment (as defined below). The "therapeutically effective amount" will vary depending on the compound, the disease and its severity, the age, weight, physical condition and responsiveness of the mammal to be treated.

The term "pharmaceutically acceptable" means biologically or pharmacologically compatible for in vivo use in animals or humans, and preferably means approved by a regulatory agency of the Federal or a State government or listed in the U.S. Pharmacopeia or other generally recognized pharmacopeia for use in animals, and more particularly in humans.

As used herein, the terms "treat," "treated," or "treating" mean both therapeutic treatment and prophylactic measures wherein the object is to slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response without excessive levels of side effects. Treatment also includes prolonging survival as compared to expected survival if not receiving treatment. Thus, "treatment of pain" or "treating pain" means an activity that alleviates or ameliorates any of the primary phenomena or secondary symptoms associated with the pain or other condition described herein.

The term "anti-solvent" or "antisolvent" is a solvent in which a compound is less soluble than the solvent that the anti-solvent is being added to. Without being bound to any particular theory, the addition of the anti-solvent to a solvent comprising the compound to be crystallized will decrease the solubility of the compound in the solvent, thus causing the compound to crystallize or precipitate out of solution. As used herein, the anti-solvent when used in reference to a compound of Formula I, including, but not limited to, its free base form, or its pharmaceutically acceptable salt form(s), is a solvent in which the compound of Formula I free base, or a pharmaceutically acceptable salt thereof, is less soluble. For example, the solvent that the compound is more soluble in can be tetrahydrofuran, tert-butylmethyl ether, methyl ethyl ketone, heptane, 2-methyl tetrahydrofuran, toluene, anisole, DMSO, water, ethanol, butanol, methanol, dicholoromethane, ethyl acetate, acetone, ethyl acetate, dimethylformamide, acetonitrile, dimethyl sulfoxide, propylene carbonate, formic acid, isopropanol, propanol, acetic acid, nitromethane, or a combination thereof. In some embodiments, the solvent that the compound is more soluble in is tert-butylmethyl ether, methyl ethyl ketone, or tetrahydrofuran, or a combination thereof. Therefore, in some embodiments, an anti-solvent is a solvent where the compound is less soluble as compared to tetrahydrofuran, tert-butylmethyl ether, methyl ethyl ketone, heptane, 2-methyl tetrahydrofuran, toluene, anisole, DMSO, water, ethanol, butanol, methanol, dicholoromethane, ethyl acetate, acetone, ethyl acetate, dimethylformamide, acetonitrile, dimethyl sulfoxide, propylene carbonate, formic acid, isopropanol, propanol, acetic acid, nitromethane, or a combination thereof. In some embodiments, an anti-solvent is a solvent where the compound is less soluble as compared to tert-butylmethyl ether, methyl ethyl ketone, or tetrahydrofuran, or a combination thereof. In some embodiments, the anti-solvent is heptane. In some embodiments, the anti-solvent is pentane. In some embodiments, the anti-solvent is t-butylmethyl ether. In some embodiments, the anti-solvent is a combination of heptane and t-butylmethyl ether. In some embodiments, the anti-solvent is a combination of pentane and t-butylmethyl ether. In some embodiments, the anti-solvent is water. During the anti-solvent precipitation or crystallization as described herein, one or more an anti-solvents as described herein were added to the solution of the compound of Formula I free base, or a pharmaceutically acceptable salt thereof, to form a supersaturating solution to precipitate or crystallize the compound of Formula I free base, or a pharmaceutically acceptable salt thereof. The solution of the compound of Formula I free base, or a pharmaceutically acceptable salt thereof, is form with an organic solvent, as described herein, such as, but not limited to tetrahydrofuran, tert-butylmethyl ether, methyl ethyl ketone, heptane, 2-methyl tetrahydrofuran, toluene, anisole, DMSO, water, ethanol, butanol, methanol, dichloromethane, ethyl acetate, acetone, ethyl acetate, dimethylformamide, acetonitrile, dimethyl sulfoxide, propylene carbonate, formic acid, isopropanol, propanol, acetic acid, nitromethane, and a combination thereof.

The term "synergy" is defined as the interaction of two or more agents so that their combined effect is greater than the sum of their individual effects. For example, if the effect of drug A alone in treating a disease is 25%, and the effect of drug B alone in treating a disease is 25%, but when the two drugs are combined the effect in treating the disease is 75%, the effect of A and B is synergistic.

The term "additive" is defined as the interaction of two or more agents so that their combined effect is the same as the sum of their individual effects. For example, if the effect of drug A alone in treating a disease is 25%, and the effect of drug B alone in treating a disease is 25%, but when the two drugs are combined the effect in treating the disease is 50%, the effect of A and B is additive.

The term "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences, Mack Publishing Co. (A. R. Gennaro edit. 1985)) for use in animals, and more particularly in humans.

The term "about", "ca.", or "approximately" means plus or minus 5%. In some embodiments, the term "about", "ca.", or "approximately" means plus or minus 10%.

tBME:Heptane 50:50 v/v % means a solution comprising about 50% v/v tert-butylmethyl ether and about 50% v/v heptane. In some embodiments, tBME:Heptane 50:50 v/v % means a solution comprising 50% v/v tert-butylmethyl ether and 50% v/v heptane.

MEK:Heptane 20:80 v/v % means a solution comprising about 20% v/v methyl ethyl ketone and about 80% v/v heptane. In some embodiments, MEK:Heptane 20:80 v/v % means a solution comprising about 20% v/v methyl ethyl ketone and about 80% v/v heptane.

THF:Heptane 22:78 v/v % means a solution comprising about 22% v/v tetrahydrofuran and about 78% v/v heptane. In some embodiments, THF:Heptane 22:78 v/v % means a solution comprising 22% v/v tetrahydrofuran and 78% v/v heptane.

The present embodiments provides methods to crystallize a compound of Formula I in free base form. A compound of Formula I can also be referred to as "(−)-6-{[(trans,trans)-4-[3-(2-methoxyethoxy)phenyl]-2-methyl-1-[2-(1H-pyrrol-1-yl)ethyl]piperi din-3-yl]methoxy}-2,3-dihydro-1H-isoindol-1-one", which has a formula of Formula I

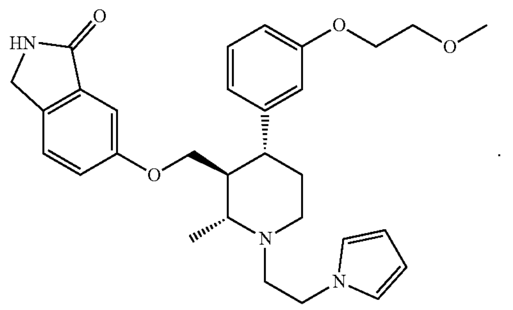

An amorphous form of the compound of Formula I or the pharmaceutical acceptable salt thereof, can be prepared according to the synthesis described in U.S. Pat. No. 10,246,436, which is hereby incorporated by reference in its entirety. The amorphous form of the compound of Formula I or the pharmaceutical acceptable salt thereof can then be isolated using lyophilization. Lyophilization may not be feasible for a large-scale manufacturing of the compound for commercial production. Alternatively, the amorphous form of the compound of Formula I in free base form can be prepared from the corresponding salts as described herein. Additionally, the amorphous form or the HCl salt form of a compound of Formula I is oily in substance and is difficult to work with and is not advantageous to use in a pharmaceutical preparation. Therefore, a crystalline form is needed that can be better used in the manufacturing and use of pharmaceutical compositions. Although in some instances preparing crystal forms of compounds can be straight forward, this was not the case for a compound of Formula I. The present embodiments provide for the surprising and unexpected result of a crystalline form of Formula I. In some embodiments, the form is Form I as provided for herein.

In some embodiments, methods of precipitating the compound of Formula I and preparing crystalline forms of the compound of Formula I are provided.

Figure 3:
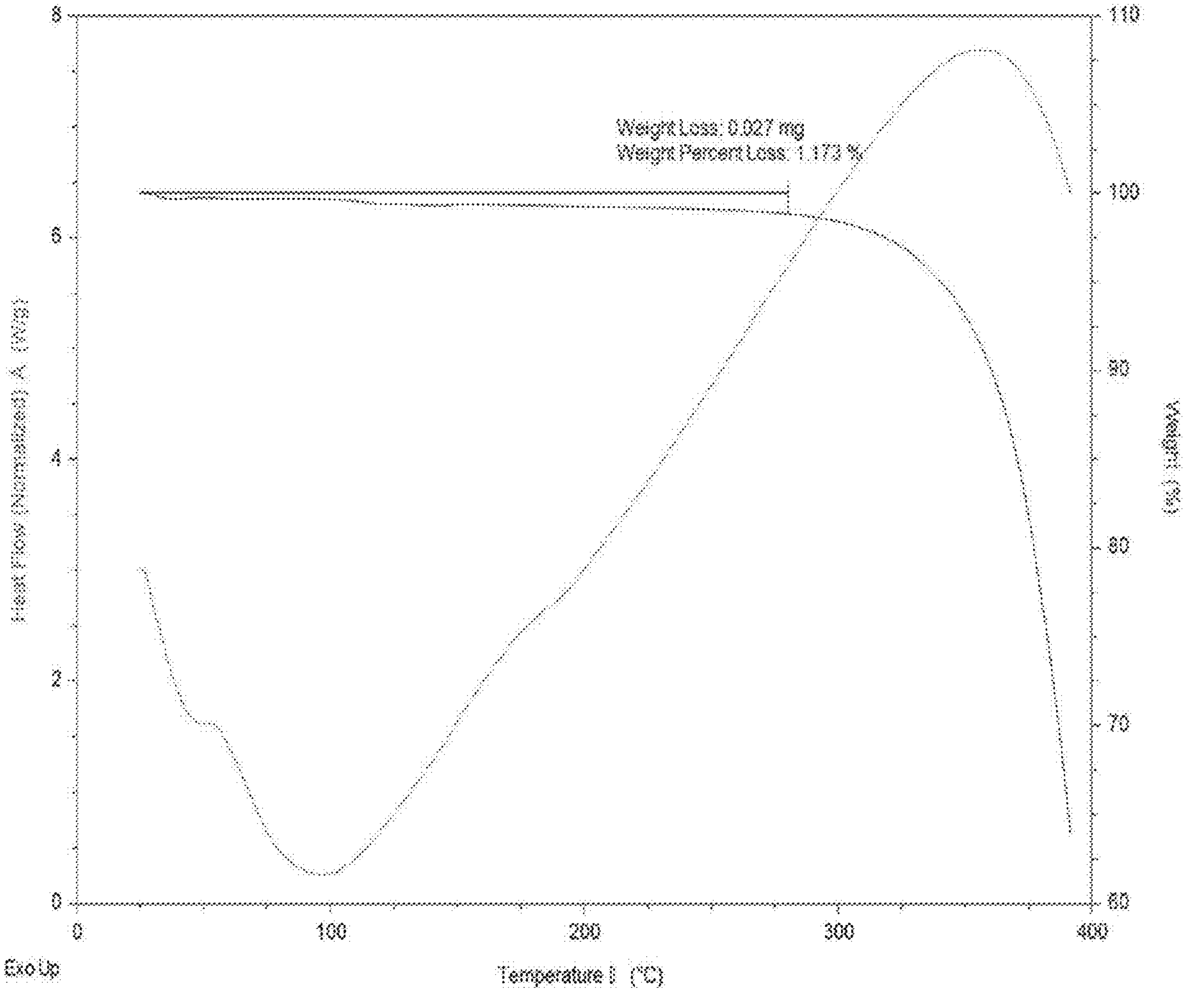
FIG. 3 shows Thermogravimetric/Differential Scanning Calorimetry (TG/DSC) thermogram of the amorphous form of the compound of Formula I in free base form.
Figure 4:
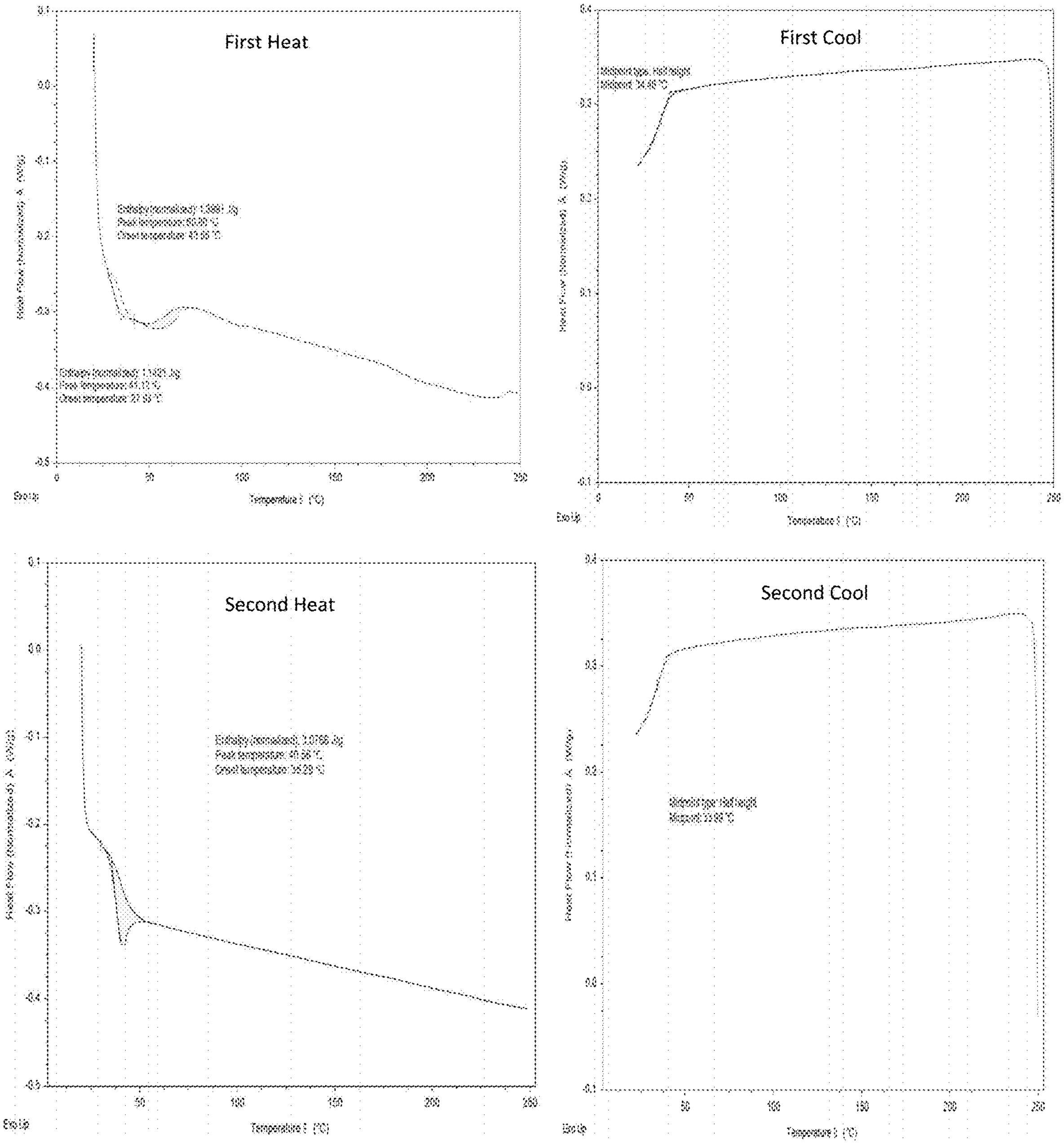
FIG. 4 shows Differential Scanning Calorimetry (DSC) thermogram of the amorphous form of the compound of Formula I in free base form.
Figure 5:
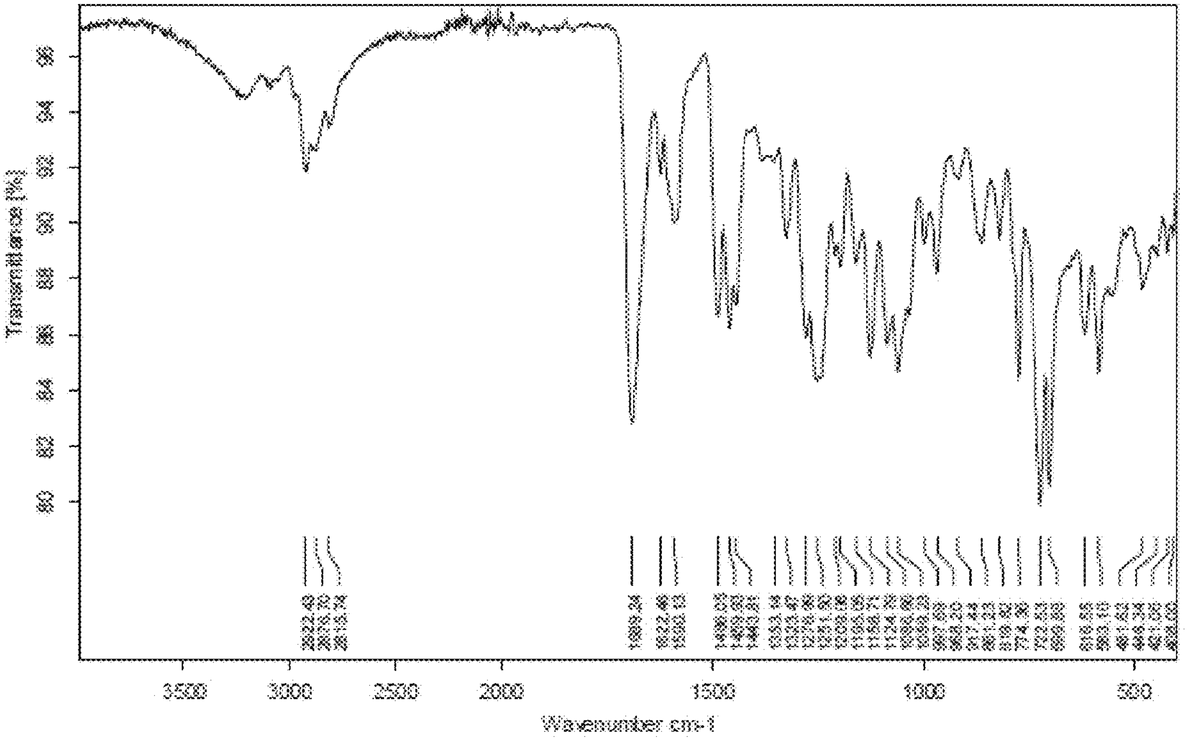
FIG. 5 shows Infrared Spectroscopy (FT-IR) analysis of the amorphous form of the compound of Formula I in free base form.
Figure 7:
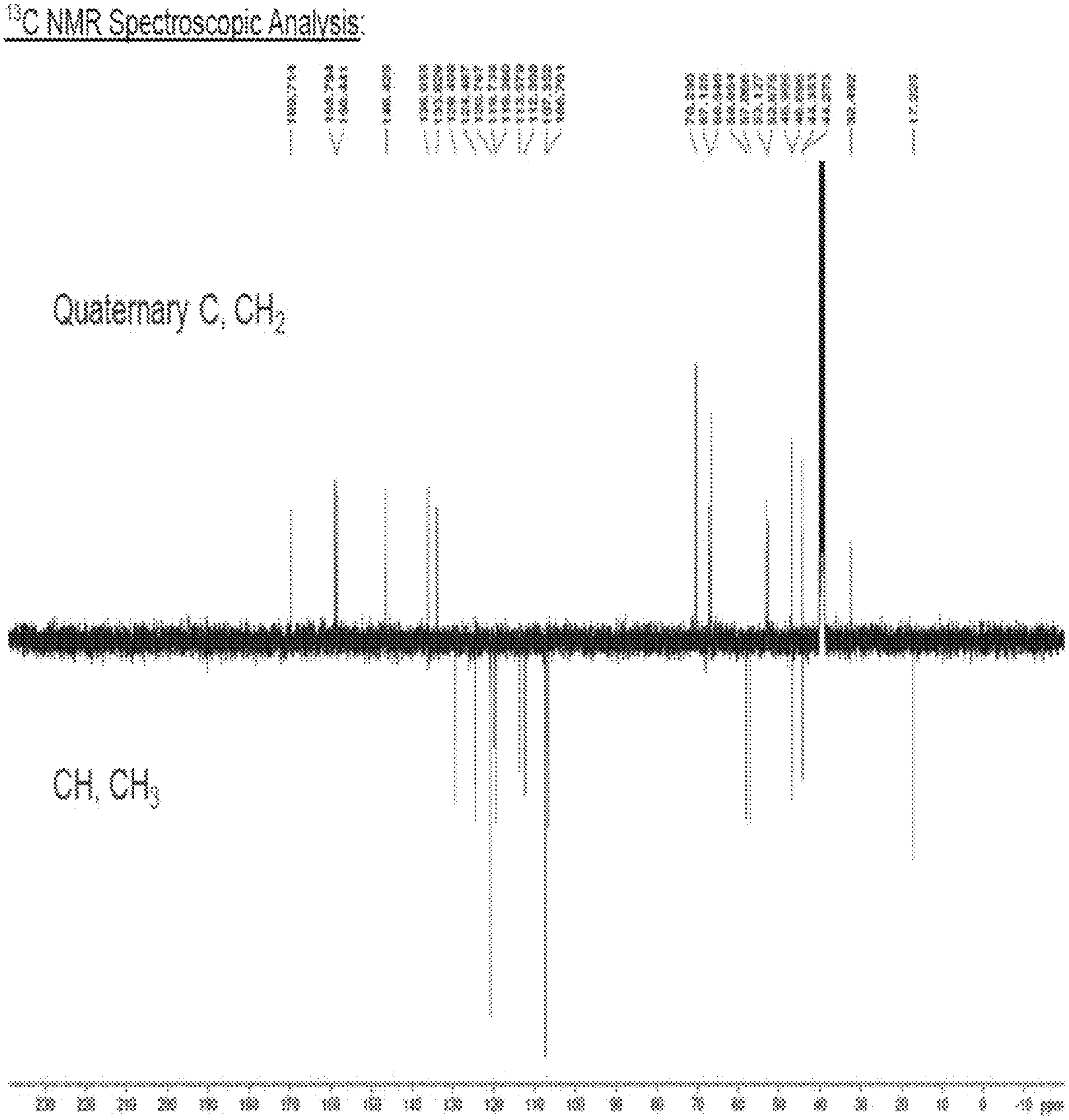
FIG. 7 shows Carbon Nuclear Magnetic Resonance Spectroscopy ($^{13}$C NMR) analysis of the amorphous form of the compound of Formula I in free base form.

An example of an amorphous form of the compound of Formula I is illustrated in FIG. 1, which shows an X-ray powder diffraction pattern of the amorphous form of the compound of Formula I. FIG. 3 shows Thermogravimetric/Differential Scanning Calorimetry (TG/DSC) thermogram of the amorphous form of the compound of Formula I in free base form. FIG. 4 shows Differential Scanning Calorimetry (DSC) thermogram of the amorphous form of the compound of Formula I in free base form.

In some embodiments, crystalline forms of the compound of Formula I are provided. In some embodiments, the crystalline Form I of the compound of Formula I (hereinafter the "crystalline Form I") is provided.

Figure 16:
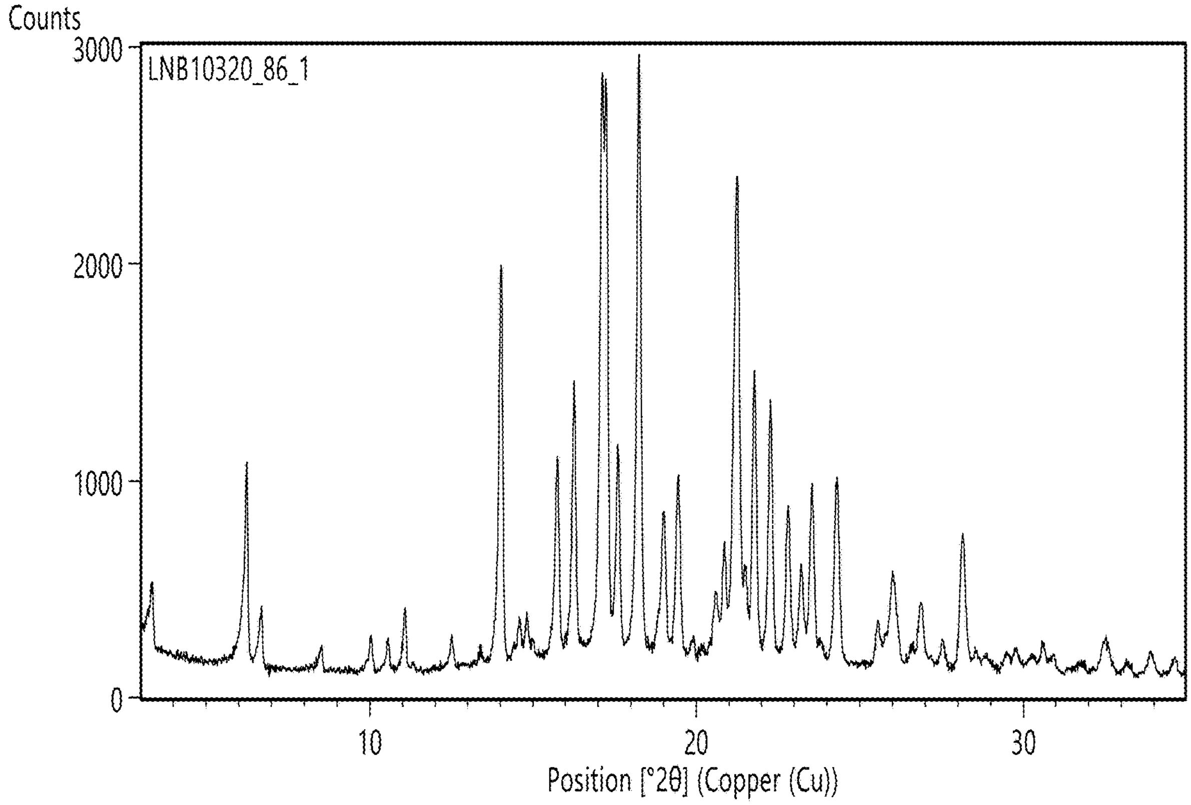
FIG. 16 shows X-ray powder diffraction pattern of the crystalline Form I.
Figure 17:
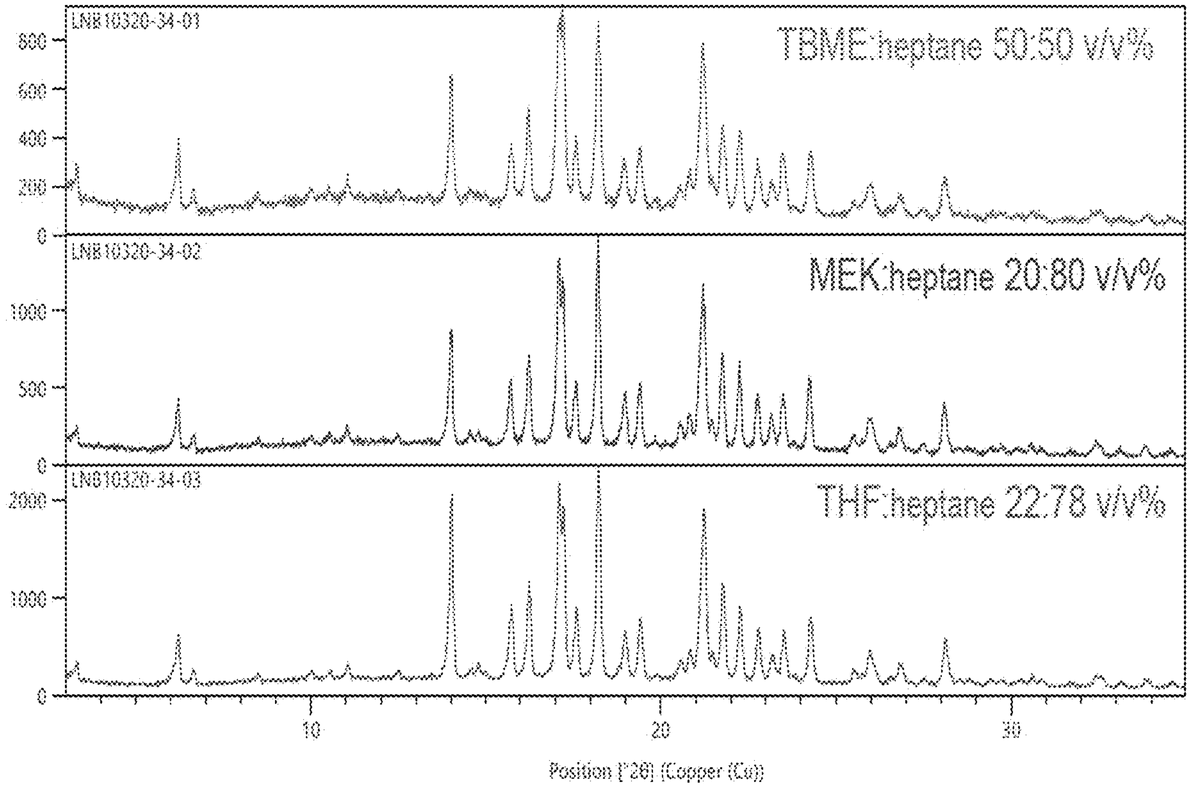
FIG. 17 shows X-ray powder diffraction patterns of the crystalline Form I directly isolated after anti-solvent additions to the solvent conditions of tBME:Heptane 50:50 v/v %, MEK:Heptane 20:80 v/v %, and THF:Heptane 22:78 v/v % (wet solids).
Figure 18:
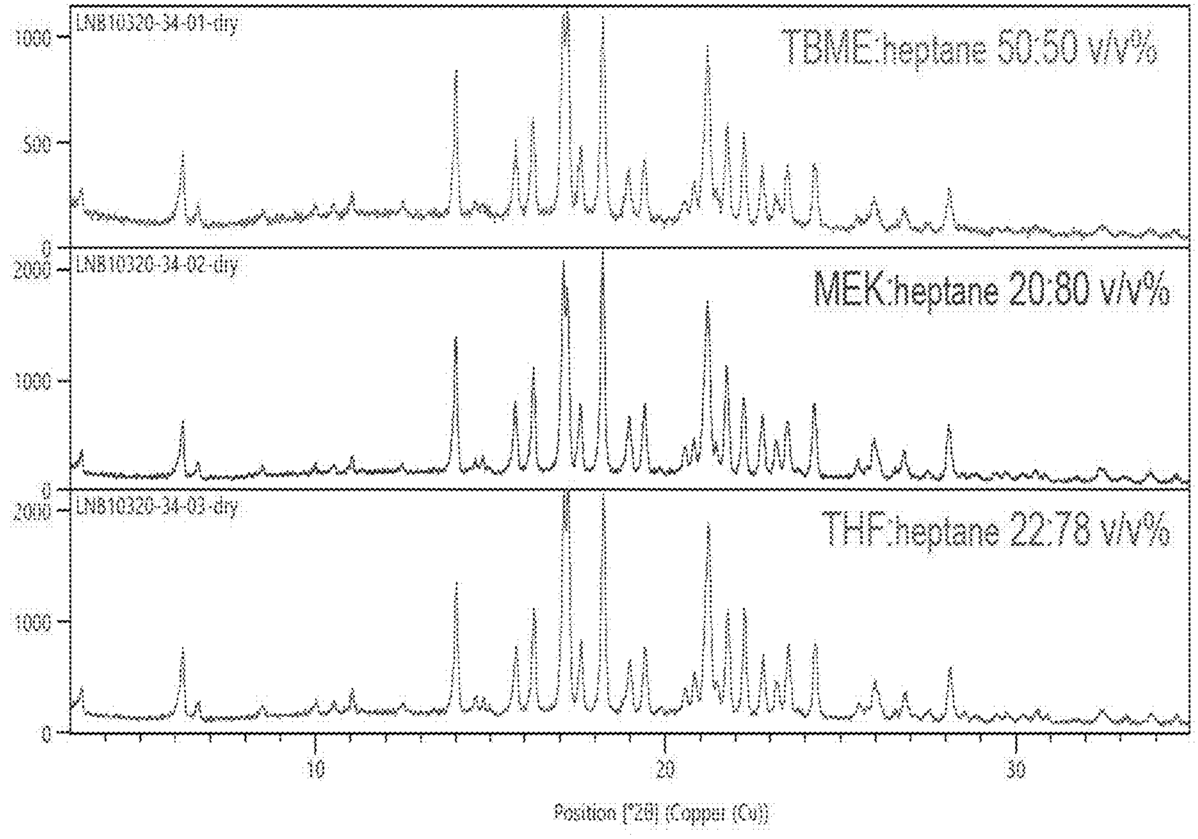
FIG. 18 shows X-ray powder diffraction patterns of the crystalline Form I isolated after anti-solvent additions to the solvent conditions of tBME:Heptane 50:50 v/v %, MEK:Heptane 20:80 v/v %, and THF:Heptane 22:78 v/v % and after drying under vacuum (dry solids).

In some embodiments, the crystalline Form I is characterized by an X-ray powder diffraction pattern substantially as shown in FIG. 16. In some embodiments, the crystalline Form I is characterized by an X-ray powder diffraction pattern comprising one or more peaks as provided in Table 9. In some embodiments, the crystalline Form I is characterized by an X-ray powder diffraction pattern comprising substantially all of, or all of, the peaks as provided in Table 9.

In some embodiments, the crystalline Form I is characterized by an X-ray powder diffraction pattern comprising a peak at about 6.3±0.5 degrees 2θ. 100971 In some embodiments, the crystalline Form I is characterized by an X-ray powder diffraction pattern comprising a peak at about 14.0±0.5 degrees 2θ.

In some embodiments, the crystalline Form I is characterized by an X-ray powder diffraction pattern comprising a peak at about 15.8±0.5 degrees 2θ.

In some embodiments, the crystalline Form I is characterized by an X-ray powder diffraction pattern comprising a peak at about 16.3±0.5 degrees 2θ.

In some embodiments, the crystalline Form I is characterized by an X-ray powder diffraction pattern comprising a peak at about 17.1±0.5 degrees 2θ.

In some embodiments, the crystalline Form I is characterized by an X-ray powder diffraction pattern comprising a peak at about 17.3±0.5 degrees 2θ.

In some embodiments, the crystalline Form I is characterized by an X-ray powder diffraction pattern comprising a peak at about 17.6±0.5 degrees 2θ.

In some embodiments, the crystalline Form I is characterized by an X-ray powder diffraction pattern comprising a peak at about 18.3±0.5 degrees 2θ.

In some embodiments, the crystalline Form I is characterized by an X-ray powder diffraction pattern comprising a peak at about 19.0±0.5 degrees 2θ.

In some embodiments, the crystalline Form I is characterized by an X-ray powder diffraction pattern comprising a peak at about 19.4±0.5 degrees 2θ.

In some embodiments, the crystalline Form I is characterized by an X-ray powder diffraction pattern comprising a peak at about 20.9±0.5 degrees 2θ.

In some embodiments, the crystalline Form I is characterized by an X-ray powder diffraction pattern comprising a peak at about 21.2±0.5 degrees 2θ.

In some embodiments, the crystalline Form I is characterized by an X-ray powder diffraction pattern comprising a peak at about 21.8±0.5 degrees 2θ.

In some embodiments, the crystalline Form I is characterized by an X-ray powder diffraction pattern comprising a peak at about 22.3±0.5 degrees 2θ.

In some embodiments, the crystalline Form I is characterized by an X-ray powder diffraction pattern comprising a peak at about 22.8±0.5 degrees 2θ.

In some embodiments, the crystalline Form I is characterized by an X-ray powder diffraction pattern comprising a peak at about 23.5±0.5 degrees 2θ.

In some embodiments, the crystalline Form I is characterized by an X-ray powder diffraction pattern comprising a peak at about 24.3±0.5 degrees 2θ.

In some embodiments, the crystalline Form I is characterized by an X-ray powder diffraction pattern comprising a peak at about 28.1±0.5 degrees 2θ.

In some embodiments, the crystalline Form I is characterized by an X-ray powder diffraction pattern comprising peaks at about 17.3±0.5 degrees 2θ, about 17.1±0.5 degrees 2θ, about 18.3±0.5 degrees 2θ, about 21.2±0.5 degrees 2θ, about 14.0±0.5 degrees 2θ.

In some embodiments, the crystalline Form I is characterized by an X-ray powder diffraction pattern comprising peaks at about 28.1, at about 24.3, at about 23.5, at about 22.8, at about 22.7, at about 22.3, at about 20.9, at about 19.4, at about 19.0, at about 17.6, about 16.3, at about 15.7, and at about 6.3±0.5 degrees 2θ.

In some embodiments, the crystalline Form I is characterized by an X-ray powder diffraction pattern comprising peaks at about 6.3±0.5 degrees 2θ, about 14.0±0.5 degrees 2θ, about 15.8±0.5 degrees 2θ, about 16.3±0.5 degrees 2θ, about 17.1±0.5 degrees 2θ, about 17.3±0.5 degrees 2θ, about 17.6±0.5 degrees 2θ, about 18.3±0.5 degrees 2θ, about 19.0±0.5 degrees 2θ, about 19.4±0.5 degrees 2θ, about 20.9±0.5 degrees 2θ, about 21.2±0.5 degrees 2θ, about 21.8±0.5 degrees 2θ, about 22.3±0.5 degrees 2θ, about 22.8±0.5 degrees 2θ, about 22.8±0.5 degrees 2θ, about 23.5±0.5 degrees 2θ, about 24.3±0.5 degrees 2θ, and about 28.1±0.5 degrees 2θ.

In some embodiments, the crystalline Form I is characterized by an X-ray powder diffraction pattern comprising peaks at about 3.4±0.5 degrees 2θ, about 6.3±0.5 degrees 2θ, about 6.7±0.5 degrees 2θ, about 8.5±0.5 degrees 2θ, about 10.0±0.5 degrees 2θ, about 10.6±0.5 degrees 2θ, about 11.1±0.5 degrees 2θ, about 12.5±0.5 degrees 2θ, about 14.0±0.5 degrees 2θ, about 14.6±0.5 degrees 2θ, about 14.8±0.5 degrees 2θ, about 15.8±0.5 degrees 2θ, about 16.3±0.5 degrees 2θ, about 17.1±0.5 degrees 2θ, about 17.3±0.5 degrees 2θ, about 17.6 f 0.5 degrees 2θ, about 18.3±0.5 degrees 2θ, about 19.0±0.5 degrees 2θ, about 19.4±0.5 degrees 2θ, about 19.9±0.5 degrees 2θ, about 20.6±0.5 degrees 2θ, about 20.9±0.5 degrees 2θ, about 21.2±0.5 degrees 2θ, about 21.5±0.5 degrees 2θ, about 21.8±0.5 degrees 2θ, about 22.3±0.5 degrees 2θ, about 22.8±0.5 degrees 2θ, about 23.2±0.5 degrees 2θ, about 23.5±0.5 degrees 2θ, about 24.3±0.5 degrees 2θ, about 25.6±0.5 degrees 2θ, about 26.0±0.5 degrees 2θ, about 26.9±0.5 degrees 2θ, about 27.5±0.5 degrees 2θ, and about 28.1±0.5 degrees 2θ.

In some embodiments, the crystalline Form I is characterized by an X-ray powder diffraction pattern comprising peaks at about 17.3±0.5 degrees 2θ, and at about 17.1±0.5 degrees 2θ. In some embodiments, the crystalline Form I is characterized by an X-ray powder diffraction pattern comprising peaks at about 17.1±0.5 degrees 2θ and at about 18.3±0.5 degrees 2θ. In some embodiments, the crystalline Form I is characterized by an X-ray powder diffraction pattern comprising peaks at about 18.3±0.5 degrees 2θ and at about 21.2±0.5 degrees 2θ. In some embodiments, the crystalline Form I is characterized by an X-ray powder diffraction pattern comprising peaks at about 21.2±0.5 degrees 2θ and at about 14.0±0.5 degrees 2θ.

In some embodiments, the crystalline Form I is characterized by an X-ray powder diffraction pattern comprising peaks at about 17.3±0.5 degrees 2θ, at about 17.1±0.5 degrees 2θ and at about 18.3±0.5 degrees 2θ.

In some embodiments, the crystalline Form I is characterized by an X-ray powder diffraction pattern comprising peaks at about 18.3±0.5 degrees 2θ, at about 21.2±0.5 degrees 2θ and at about 14.0±0.5 degrees 2θ.

In some embodiments, the crystalline Form I is characterized by an X-ray powder diffraction pattern comprising peaks at about 17.3±0.5 degrees 2θ, at about 17.1±0.5 degrees 2θ, at about 18.3±0.5 degrees 2θ and at about 21.2±0.5 degrees 2θ.

In some embodiments, the crystalline Form I is characterized by an X-ray powder diffraction pattern comprising peaks at about 17.3±0.5 degrees 2θ, at about 17.1±0.5 degrees 2θ, at about 18.3±0.5 degrees 2θ, and optionally one or more peaks at about at about 6.3±0.5 degrees 2θ, about 15.8±0.5 degrees 2θ, about 16.3±0.5 degrees 2θ, about 17.6±0.5 degrees 2θ, about 19.0±0.5 degrees 2θ, about 19.4±0.5 degrees 2θ, about 20.9±0.5 degrees 2θ, about 21.8 f 0.5 degrees 2θ, about 22.3±0.5 degrees 2θ, about 22.8±0.5 degrees 2θ, about 23.5±0.5 degrees 2θ, about 24.3±0.5 degrees 2θ, and about 28.1±0.5 degrees 2θ.

In some embodiments, the crystalline Form I is characterized by an X-ray powder diffraction pattern comprising peaks at about 17.3±0.5 degrees 2θ, about 17.1±0.5 degrees 2θ, about 18.3±0.5 degrees 2θ, about 21.2±0.5 degrees 2θ, about 14.0±0.5 degrees 2θ and optionally having one or more peaks at about 6.3±0.5 degrees 2θ, about 15.8±0.5 degrees 2θ, about 16.3±0.5 degrees 2θ, about 17.6±0.5 degrees 2θ, about 19.0±0.5 degrees 2θ, about 19.4 f 0.5 degrees 2θ, about 20.9±0.5 degrees 2θ, about 21.8±0.5 degrees 2θ, about 22.3±0.5 degrees 2θ, about 22.8±0.5 degrees 2θ, about 23.5±0.5 degrees 2θ, about 24.3±0.5 degrees 2θ, and about 28.1±0.5 degrees 2θ.

In some embodiments, the crystalline Form I is characterized by an X-ray powder diffraction pattern comprising peaks at about 17.3±0.5 degrees 2θ, about 17.1±0.5 degrees 2θ, about 18.3±0.5 degrees 2θ, about 21.2±0.5 degrees 2θ, about 14.0±0.5 degrees 2θ and optionally having one or more peaks at about 3.4±0.5 degrees 2θ, about 6.3±0.5 degrees 2θ, about 6.7±0.5 degrees 2θ, about 8.5±0.5 degrees 2θ, about 10.0±0.5 degrees 2θ, about 10.6±0.5 degrees 2θ, about 11.1±0.5 degrees 2θ, about 12.5±0.5 degrees 2θ, about 14.6±0.5 degrees 2θ, about 14.8±0.5 degrees 2θ, about 15.8±0.5 degrees 2θ, about 16.3±0.5 degrees 2θ, about 17.6±0.5 degrees 2θ, about 19.0±0.5 degrees 2θ, about 19.4±0.5 degrees 2θ, about 19.9±0.5 degrees 2θ, about 20.6±0.5 degrees 2θ, about 20.9±0.5 degrees 2θ, about 21.5±0.5 degrees 2θ, about 21.8±0.5 degrees 2θ, about 22.3±0.5 degrees 2θ, about 22.8±0.5 degrees 2θ, about 23.2±0.5 degrees 2θ, about 23.5±0.5 degrees 2θ, about 24.3±0.5 degrees 2θ, about 25.6±0.5 degrees 2θ, about 26.0±0.5 degrees 2θ, about 26.9±0.5 degrees 2θ, about 27.5±0.5 degrees 2θ, and about 28.1±0.5 degrees 2θ.

As used herein, unless otherwise indicated, the phrase "one or more peaks" should be understood to be inclusive of (i) crystalline forms that have XRD peaks at every peak value recited after this phrase, (ii) crystalline forms that have an XRD peak at only one of the peak values recited after this phrase, as well as (iii) crystalline forms that have XRD peaks at two or more (e.g., three or more, four or more, five or more, six or more, or even seven or more) of the peak values recited after this phrase.

Figure 25:
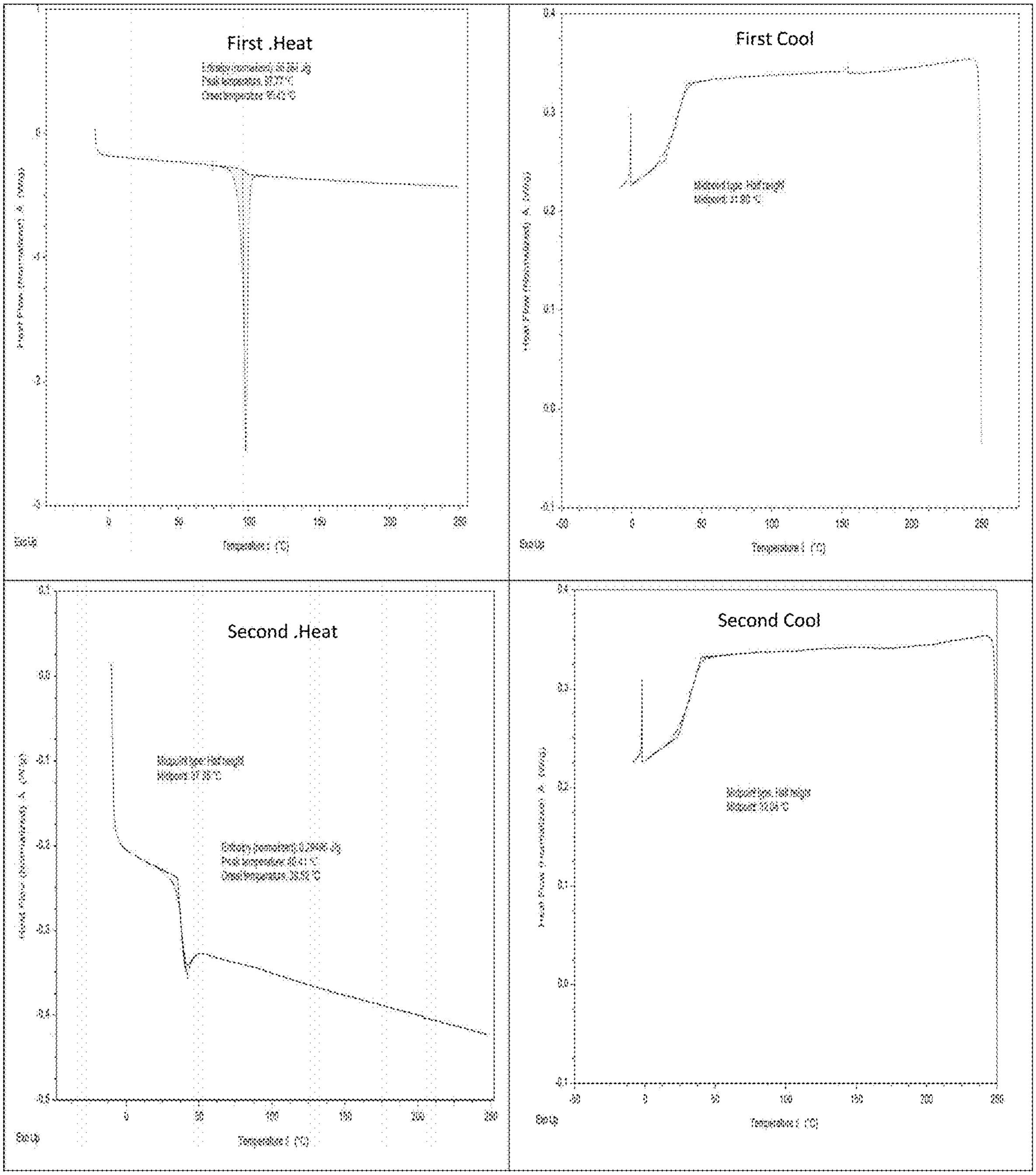
FIG. 25 shows Differential Scanning Calorimetry (DSC) thermogram of the crystalline Form I prepared from tBME:Heptane 50:50 v/v %.
Figure 26:
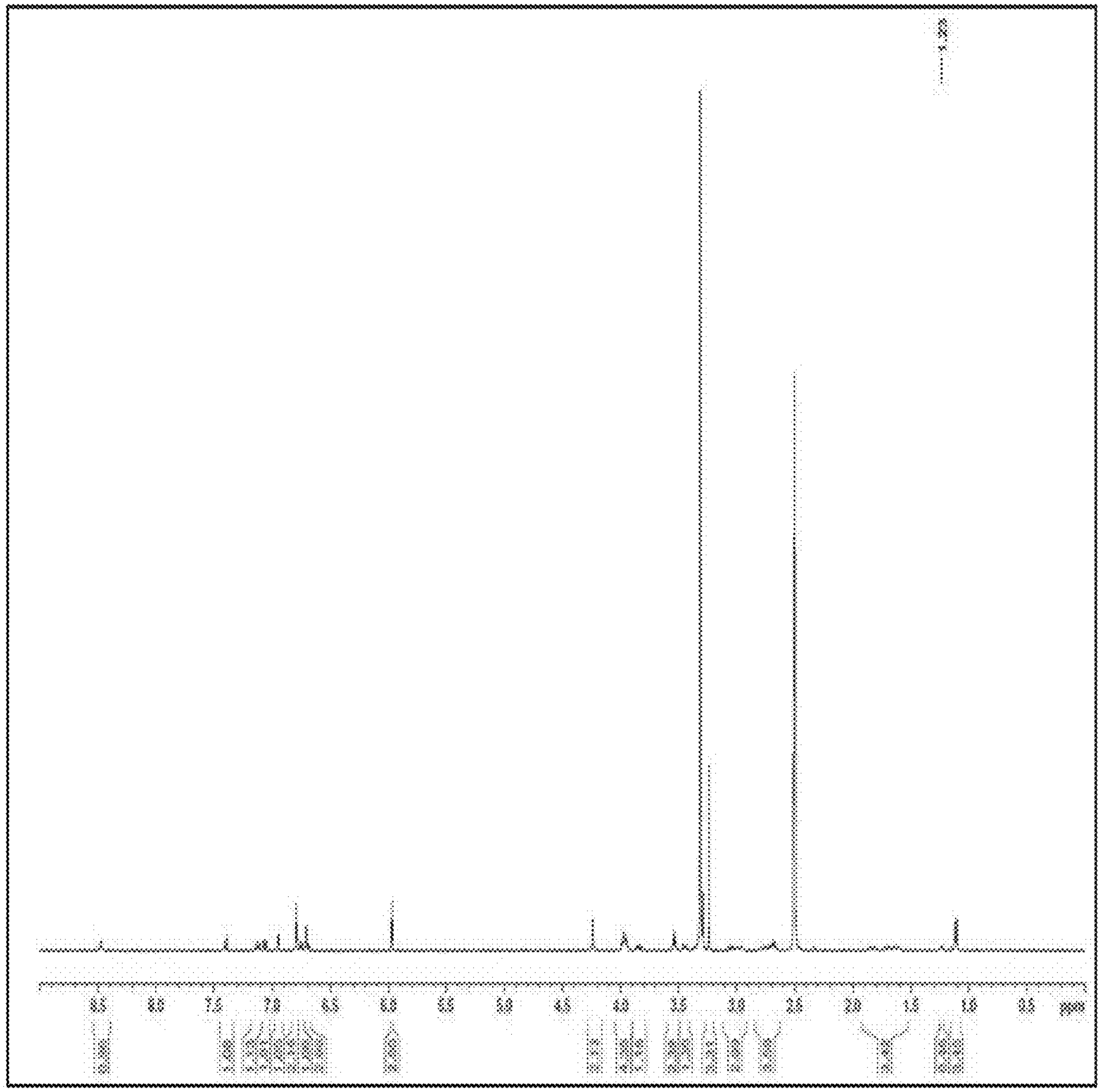
FIG. 26 shows Proton Nuclear Magnetic Resonance Spectroscopy ($^1$H NMR) analysis of the crystalline Form I prepared from tBME:Heptane 50:50 v/v %.
Figure 27:
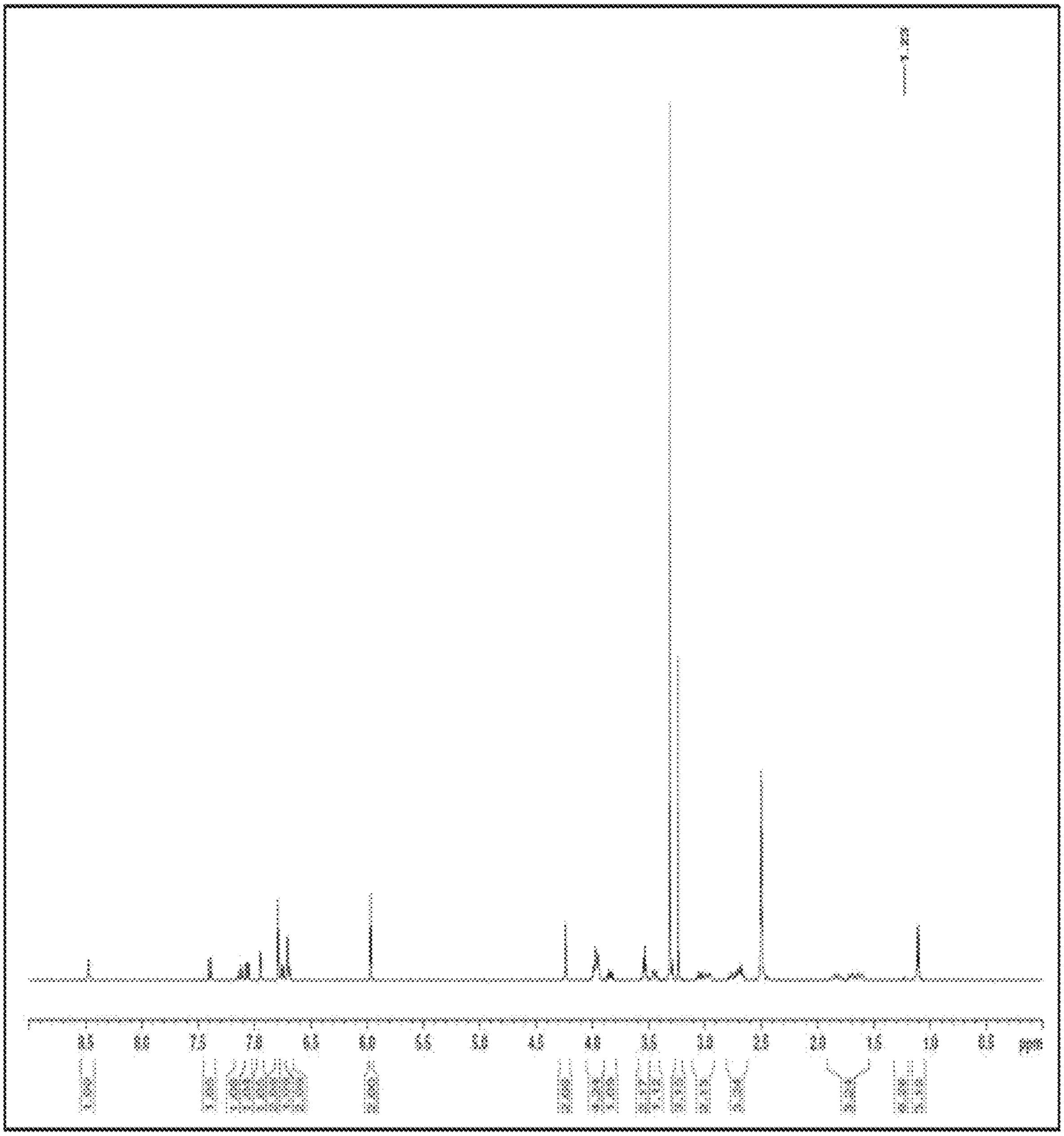
FIG. 27 shows Proton Nuclear Magnetic Resonance Spectroscopy ($^1$H NMR) analysis of the crystalline Form I prepared from MEK:Heptane 20:80 v/v %.
Figure 28:
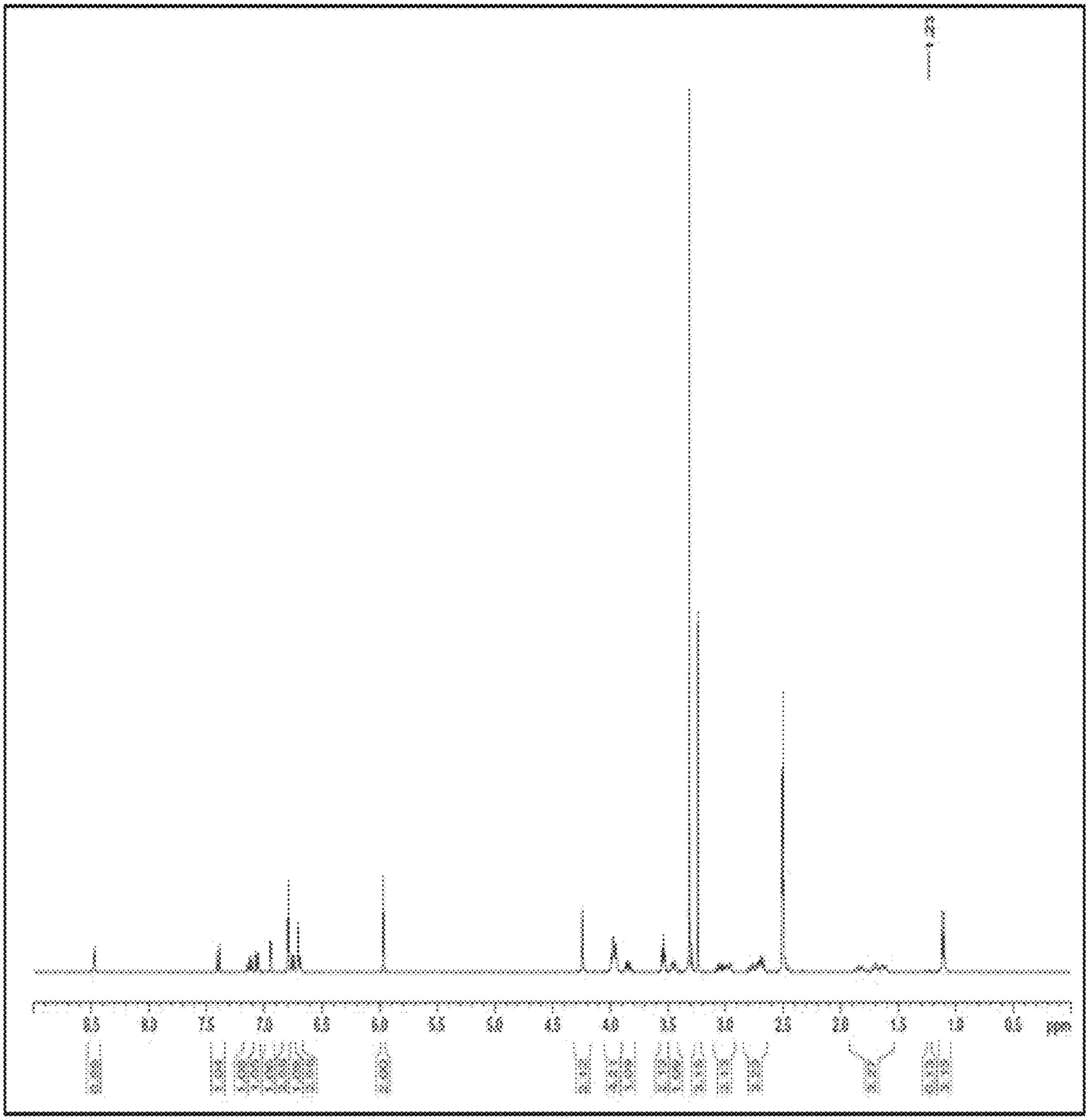
FIG. 28 shows Proton Nuclear Magnetic Resonance Spectroscopy ($^1$H NMR) analysis of the crystalline Form I prepared from THF:Heptane 22:78 v/v %.
Figure 29:
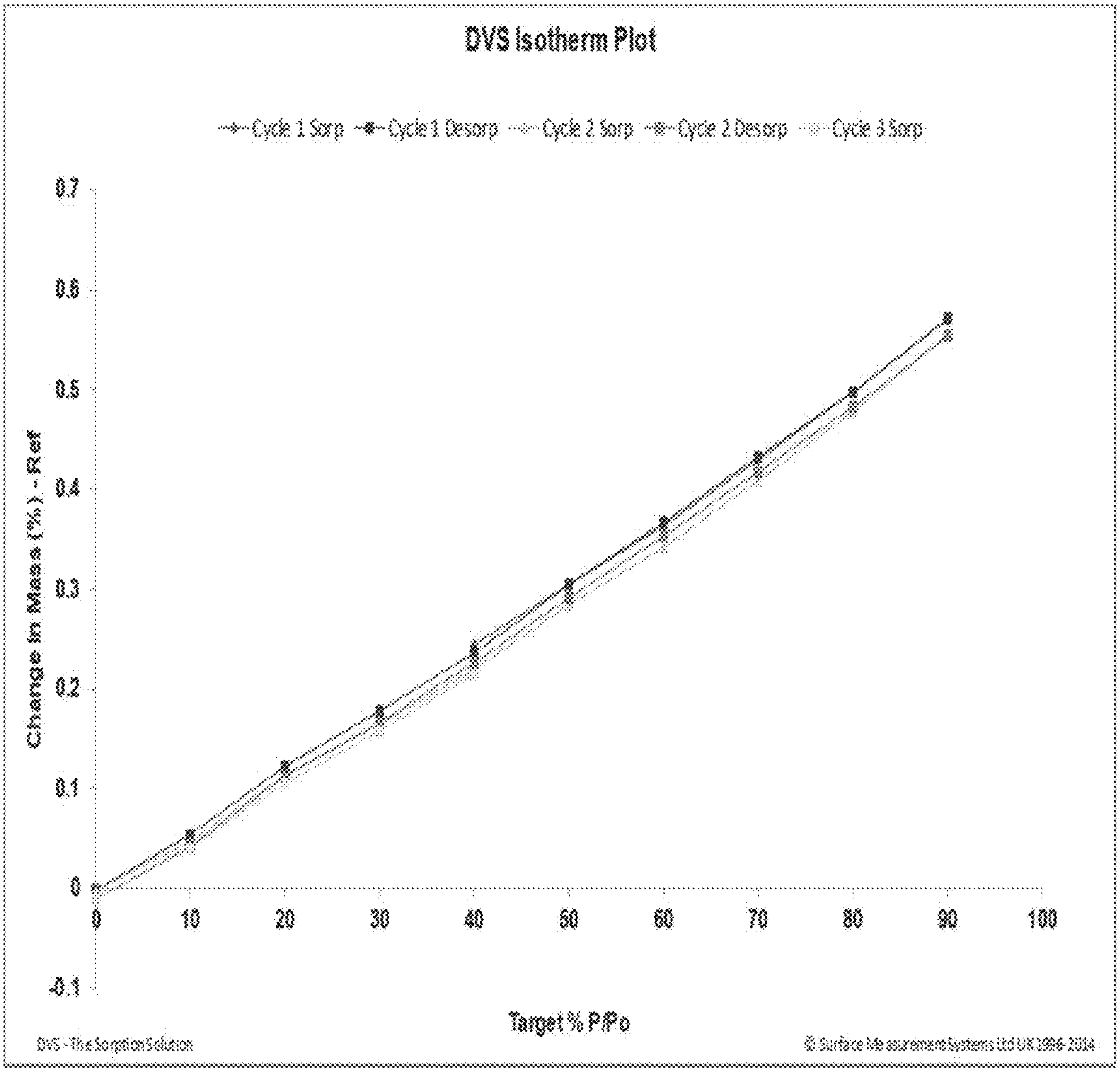
FIG. 29 shows a Dynamic Vapour Sorption (DVS) isotherm plot of the crystalline Form I prepared from tBME:Heptane 50:50 v/v %.
Figure 30:
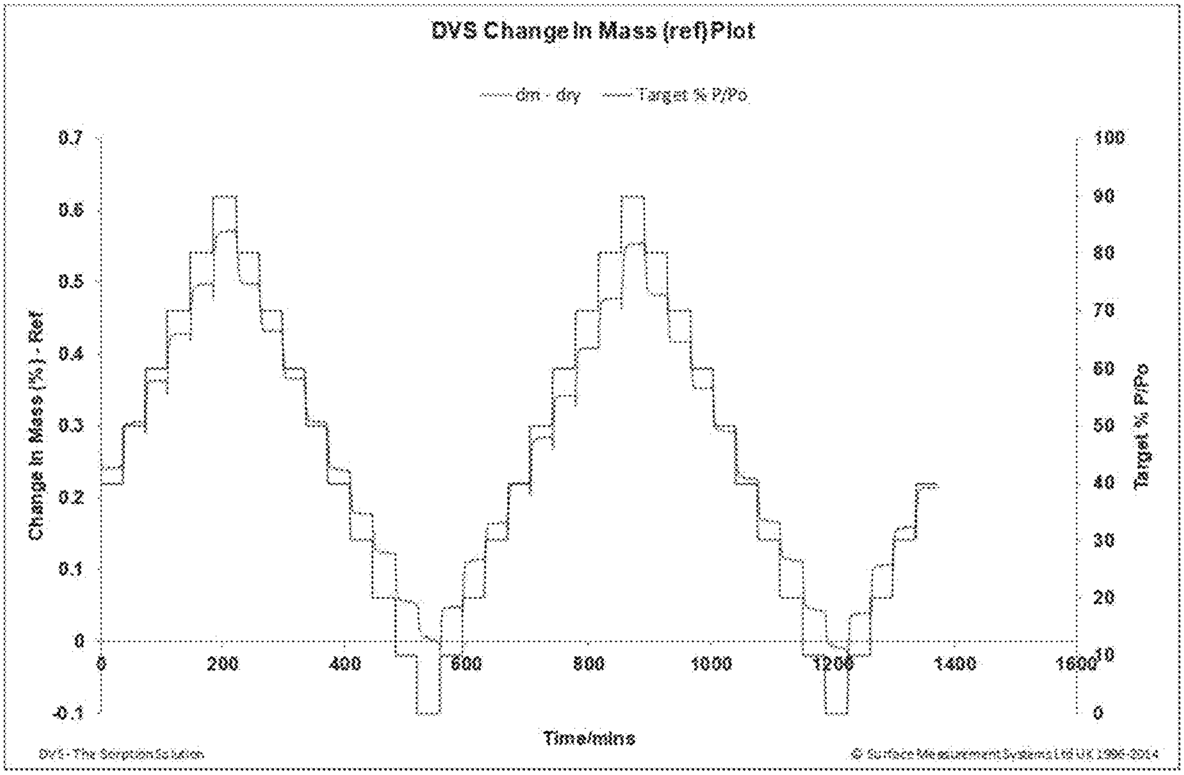
FIG. 30 shows a Dynamic Vapour Sorption (DVS) change in mass plot of the crystalline Form I prepared from tBME:Heptane 50:50 v/v %.
Figure 31:
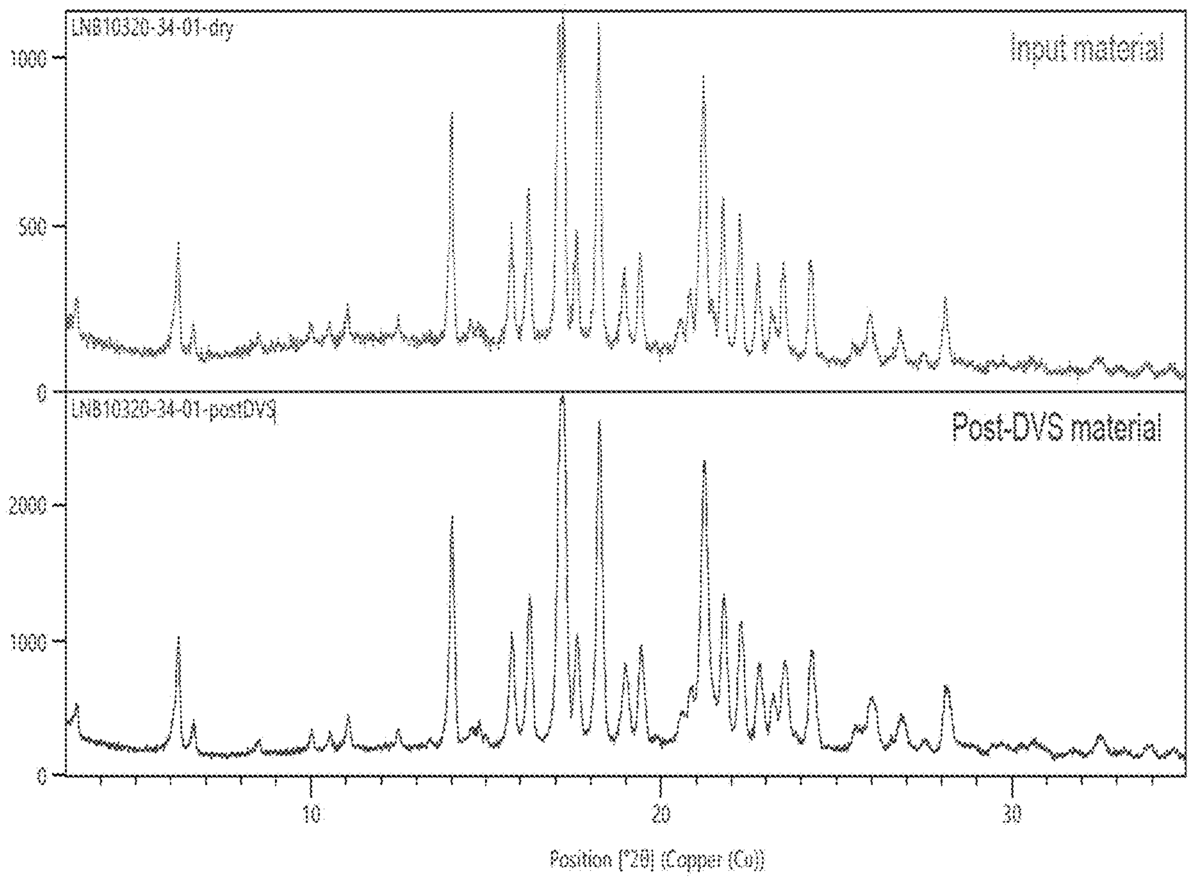
FIG. 31 shows XRPD patterns of the crystalline Form I prepared from tBME:Heptane 50:50 v/v % before and after Dynamic Vapour Sorption (DVS) analysis.

In some embodiments, the crystalline Form I is characterized by a DSC thermogram as shown in FIG. 25.

In some embodiments, the crystalline Form I is characterized by any combination of the above data.

In some embodiments, the X-ray powder diffraction peaks recited herein for particular embodiments can vary by ±0.4 degrees 2θ, by ±0.3 degrees 2θ, by ±0.2 degrees 2θ, or by ±0.1 degrees 2θ.

In some embodiments, the crystalline Form I is characterized by an X-ray powder diffraction pattern comprising peaks having d-spacing values at about 14.1, about 6.3, about 5.6, about 5.4, about 5.2, about 5.1, about 5.0, about 4.8, about 4.7, about 4.6, about 4.3, about 4.2, about 4.0, about 3.9, about 3.8, about 3.7, and 3.2±0.5 angstroms.

In some embodiments, the crystalline Form I is characterized by an X-ray powder diffraction pattern comprising peaks having d-spacing values at about 6.3, at about 5.1, at about 5.2, at about 4.9, and at about 4.2±0.5 angstroms.

In some embodiments, the crystalline Form I is characterized by an X-ray powder diffraction pattern comprising a d-spacing value at about 14.1±0.5 angstroms.

In some embodiments, the crystalline Form I is characterized by an X-ray powder diffraction pattern comprising a d-spacing value at about 6.3±0.5 angstroms.

In some embodiments, the crystalline Form I is characterized by an X-ray powder diffraction pattern comprising a d-spacing value at about 5.6±0.5 angstroms.

In some embodiments, the crystalline Form I is characterized by an X-ray powder diffraction pattern comprising a d-spacing value at about 5.4±0.5 angstroms.

In some embodiments, the crystalline Form I is characterized by an X-ray powder diffraction pattern comprising a d-spacing value at about 5.2±0.5 angstroms.

In some embodiments, the crystalline Form I is characterized by an X-ray powder diffraction pattern comprising a d-spacing value at about 5.1±0.5 angstroms.

In some embodiments, the crystalline Form I is characterized by an X-ray powder diffraction pattern comprising a d-spacing value at about 5.0±0.5 angstroms.

In some embodiments, the crystalline Form I is characterized by an X-ray powder diffraction pattern comprising a d-spacing value at about 4.9±0.5 angstroms.

In some embodiments, the crystalline Form I is characterized by an X-ray powder diffraction pattern comprising a d-spacing value at about 4.7±0.5 angstroms.

In some embodiments, the crystalline Form I is characterized by an X-ray powder diffraction pattern comprising a d-spacing value at about 4.6±0.5 angstroms.

In some embodiments, the crystalline Form I is characterized by an X-ray powder diffraction pattern comprising a d-spacing value at about 4.3±0.5 angstroms.

In some embodiments, the crystalline Form I is characterized by an X-ray powder diffraction pattern comprising a d-spacing value at about 4.2±0.5 angstroms.

In some embodiments, the crystalline Form I is characterized by an X-ray powder diffraction pattern comprising a d-spacing value at about 4.1±0.5 angstroms.

In some embodiments, the crystalline Form I is characterized by an X-ray powder diffraction pattern comprising a d-spacing value at about 4.0±0.5 angstroms.

In some embodiments, the crystalline Form I is characterized by an X-ray powder diffraction pattern comprising a d-spacing value at about 3.9±0.5 angstroms.

In some embodiments, the crystalline Form I is characterized by an X-ray powder diffraction pattern comprising a d-spacing value at about 3.8±0.5 angstroms.

In some embodiments, the crystalline Form I is characterized by an X-ray powder diffraction pattern comprising a d-spacing value at about 3.7±0.5 angstroms.

In some embodiments, the crystalline Form I is characterized by an X-ray powder diffraction pattern comprising a d-spacing value at about 3.2±0.5 angstroms.

In some embodiments, the crystalline Form I is characterized by an X-ray powder diffraction pattern comprising a d-spacing value substantially as shown in Table 9

In some embodiments, the X-ray powder diffraction peaks recited herein for particular embodiments having d-spacing values can vary by ±4% nm, by ±3% nm, by ±2% nm, or by ±1% nm or by ±4% angstroms, by ±3% angstroms, by ±2% angstroms, or by ±1% angstroms.

One skilled in the art will understand that the relative intensities and positions of the peaks obtained by X-ray powder diffraction may vary depending upon, inler alia, the sample preparation technique, the sample mounting procedure, and the particular instrument employed. For example, in some embodiments, the listed X-ray powder diffraction pattern peaks for the crystalline Form I of the compound of Formula I is about ±0.2 degrees 2θ.

In some embodiments, the crystalline Form I of the compound of Formula I is characterized using High Performance Liquid Chromatography and using microscopy. FIG. 32 shows an example of a HPLC chromatogram of Form I. Other methods for characterizing Form I could also be used.

Form I can have any desired degree of purity, relative to other substances or components in the preparation. In some embodiments, the crystalline Form I is provided such that it is substantially pure, such as, for example, having greater than 30%, greater than 40%, greater than 50%, greater than 60%, greater than 70%, greater than 80%, greater than 85%, greater than 90%, greater than 95%, greater than 96%, greater than 97%, greater than 98%, greater than 99%, greater than 99.2%, greater than 99.4%, greater than 99.5%, greater than 99.6%, greater than 99.7%, or greater than 99.9% purity, relative to other substances or components in the preparation.

In exemplary embodiments, the crystalline Form I is about 45% to 95% pure, such as, for example, about 50% to 95% pure, about 55% to 90% pure, about 60% to 95% pure, or about 70% to 99% pure, relative to other substances or components in the preparation. In some embodiments, the crystalline Form I is about 95% to 99% pure. In some embodiments, the crystalline Form I is about 90% to 95% pure. In some embodiments, the crystalline Form I is about 85% to 90% pure. In some embodiments, the crystalline Form I is about 80% to 85% pure. In some embodiments, the crystalline Form I is about 75% to 80% pure. In some embodiments, the crystalline Form I is about 70% to 75% pure. In certain embodiments, the crystalline Form I is about 65% to 70% pure. In some embodiments, the crystalline Form I is about 60% to 65% pure. In other embodiments, the crystalline Form I is about 55% to 60% pure. In yet other embodiments, the crystalline Form I is about 50% to 55% pure. In some embodiments, the crystalline Form I is about 45% to 50% pure.

In some embodiments, the crystalline Form I may comprise one or more impurities and/or a degradation product, such as a hydrolysis product, acetylation product, a formylation product, an oxidation product, a water-mediated degradation product, and/or a deamidation product. In some embodiments, a composition comprising the crystalline Form I may comprise one or more impurities and/or a degradation product, such as a hydrolysis product, acetylation product, a formylation product, an oxidation product, a water-mediated degradation product, and/or a deamidation product. In some embodiments, the one or more impurities may be biologically active.

In some embodiments, the crystalline Form I and/or the composition comprising the crystalline Form I can contain any desired purity relative to hydrolysis product(s). In some embodiments, the composition comprises less than about 10% by weight of hydrolysis product(s), relative to the total weight of Form I and/or the composition, such as, for example, less than about 7.5 wt. %, less than about 5 wt. %, or less than about 2 wt. % of hydrolysis product(s). In some embodiments, the crystalline Form I and/or the composition comprises from about 0.05% to about 5% by weight of hydrolysis product(s). In some embodiments, the crystalline Form I and/or the composition comprises from about 0.05% to about 2% by weight of the hydrolysis product(s). In some embodiments, the crystalline Form I and/or the composition comprises from about 0.1% to about 2% by weight of the hydrolysis product(s). In some embodiments, the crystalline Form I and/or the composition comprises from about 0.01% to about 2% by weight of the hydrolysis product(s).

Alternatively, or in addition, the crystalline Form I and/or the composition comprising the crystalline Form I can contain any desired purity relative to acetylation product(s). In some embodiments, the acetylation product may comprise less than 10% by weight of the crystalline Form I and/or the composition. In some embodiments, the acetylation product may comprise less than 7.5% by weight of the crystalline Form I and/or the composition. In some embodiments, the acetylation product may comprise less than 5% by weight of the crystalline Form I and/or the composition. In some embodiments, the acetylation product may comprise less than 2% by weight of the crystalline Form I and/or the composition. In some embodiments, the acetylation product may comprise less than 1% by weight of the crystalline Form I and/or the composition. In some embodiments, the acetylation product may comprise less than 0.5% by weight of Form I and/or the composition. In some embodiments, the acetylation product may comprise from about 0.05% to about 5% by weight of Form I and/or the composition. In some embodiments, the acetylation product may comprise from about 0.05% to about 2% by weight of Form I and/or the composition. In some embodiments, the acetylation product may comprise from about 0.1% to about 2% by weight of Form I and/or the composition. In some embodiments, the acetylation product may comprise from about 0.01% to about 2% by weight of the composition.

Alternatively, or in addition, the crystalline Form I and/or the composition comprising the crystalline Form I can contain any desired purity relative to formylation product(s). In some embodiments, the formylation product may comprise less than 10% by weight of Form I and/or the composition. In some embodiments, the formylation product may comprise less than 7.5% by weight of Form I and/or the composition. In some embodiments, the formylation product may comprise less than 5% by weight of Form I and/or the composition. In some embodiments, the formylation product may comprise less than 2% by weight of Form I and/or the composition. In some embodiments, the formylation product may comprise from about 0.05% to about 5% by weight of Form I and/or the composition. In some embodiments, the formylation product may comprise from about 0.05% to about 2% by weight of Form I and/or the composition. In some embodiments, the formylation product may comprise from about 0.1% to about 2% by weight of Form I and/or the composition.

Alternatively, or in addition, the crystalline Form I and/or the composition comprising the crystalline Form I can contain any desired purity relative to oxidation product(s). In some embodiments, the oxidation product may comprise less than 10% by weight of Form I and/or the composition. In some embodiments, the oxidation product may comprise less than 7.5% by weight of Form I and/or the composition. In some embodiments, the oxidation product may comprise less than 5% by weight of Form I and/or the composition. In some embodiments, the oxidation product may comprise less than 2% by weight of Form I and/or the composition. In some embodiments, the oxidation product may comprise from about 0.05% to about 5% by weight of Form I and/or the composition. In some embodiments, the oxidation product may comprise from about 0.05% to about 2% by weight of Form I and/or the composition. In some embodiments, the oxidation product may comprise from about 0.1% to about 2% by weight of Form I and/or the composition. In some embodiments, the oxidation product may comprise from about 0.01% to about 2% by weight of Form I and/or the composition.

Alternatively, or in addition, the crystalline Form I and/or the composition comprising the crystalline Form I can contain any desired purity relative to water-mediated degradation product(s). In some embodiments, the water-mediated degradation product(s) may comprise less than 10% by weight of Form I and/or the composition. In some embodiments, the water-mediated degradation product(s) may comprise less than 7.5% by weight of Form I and/or the composition. In some embodiments, the water-mediated degradation product(s) may comprise less than 5% by weight of Form I and/or the composition. In other embodiments, the water-mediated degradation product(s) may comprise less than 2% by weight of Form I and/or the composition. In some embodiments, the water-mediated degradation product(s) may comprise from about 0.05% to about 5% by weight of Form I and/or the composition. In exemplary embodiments, the water-mediated degradation product(s) may comprise from about 0.05% to about 2% by weight of Form I and/or the composition. In some embodiments, the water-mediated degradation product(s) may comprise from about 0.1% to about 2% by weight of Form I and/or the composition. In some embodiments, the water-mediated degradation product(s) may comprise from about 0.01% to about 2% by weight of Form I and/or the composition Alternatively, or in addition, the crystalline Form I and/or the composition comprising the crystalline Form I can contain any desired purity relative to deamidation product(s). In some embodiments, the deamidation product may comprise less than 10% by weight of Form I and/or the composition. In some embodiments, the deamidation product may comprise less than 7.5% by weight of Form I and/or the composition. In some embodiments, the deamidation product may comprise less than 5% by weight of Form I and/or the composition. In other embodiments, the deamidation product may comprise less than 2% by weight of Form I and/or the composition. In some embodiments, the deamidation product may comprise from about 0.05% to about 5% by weight of Form I and/or the composition. In some embodiments, the deamidation product may comprise from about 0.05% to about 2% by weight of Form I and/or the composition. In some embodiments, the deamidation product may comprise from about 0.1% to about 2% by weight of Form I and/or the composition. In some embodiments, the deamidation product may comprise from about 0.01% to about 2% by weight of Form I and/or the composition.

In some embodiments, a composition is provided comprising the crystalline Form I and less than 10 wt. % such as less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of a degradation product, such as a hydrolysis product, a formylation product, an oxidation product, a water-mediated degradation product, and/or a deamidation product.

In some embodiments, a composition is provided comprising the crystalline Form I and less than 20 wt. % such as less than 18 wt. %, less than 16 wt. %, less than 14 wt. %, less than 12 wt. %, less than 10 wt. %, less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of a degradation product, such as a hydrolysis product, an acetylation product, a formylation product, an oxidation product, a water-mediated degradation product, and/or a deamidation product.

In some embodiments, a composition is provided comprising the crystalline Form I and less than 10 wt. % such as less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of one or more impurities and/or a degradation product, such as a hydrolysis product, a formylation product, an oxidation product, a water-mediated degradation product, and/or a deamidation product.

In some embodiments, a composition is provided comprising the crystalline Form I and less than 20 wt. % such as less than 18 wt. %, less than 16 wt. %, less than 14 wt. %, less than 12 wt. %, less than 10 wt. %, less than 8 wt. %, less than 6 wt. %, less than 5 wt. %, less than 4 wt. %, less than 3 wt. %, less than 2 wt. %, less than 1 wt. %, less than 0.5 wt. %, or less than 0.25 wt. % of a combined total of one or more impurities and/or a degradation product, such as a hydrolysis product, an acetylation product, a formylation product, an oxidation product, a water-mediated degradation product, and/or a deamidation product.

In some embodiments, a composition is provided comprising the crystalline Form I and less than about 40 wt %, such as less than about 30 wt. %, less than about 20 wt. %, less than about 15 wt. %, less than about 10 wt. %, less than about 8 wt. %, less than about 6 wt. %, less than about 5 wt. %, less than about 4 wt. %, less than about 3 wt. %, less than about 2 wt. %, less than about 1 wt. %, less than about 0.5 wt. %, less than about 0.1 wt. %, or less than about 0.01 wt. % of amorphous form of the compound of Formula I.

In some embodiments, a composition is provided comprising from about 50:50 and 99:1 Form I to amorphous form of the compound of Formula I, such as, for example, from about 55:45 and 95:5 Form I to amorphous form of the compound of Formula I, from about 60:40 and 90:10 Form I to amorphous form of the compound of Formula I, from about 70:30 and 85:15 Form I to amorphous form of the compound of Formula I, or from about 75:25 and 99:1 Form I to amorphous form of the compound of Formula I.

In some embodiments, processes for preparing crystalline forms of the compound of Formula I are provided. In some embodiments, the crystalline Form I is produced by precipitating and crystallizing the compound of Formula I and optionally isolating the crystalline Form 1. In some embodiments, the crystalline Form I is prepared by precipitating and crystallizing the compound of Formula I in an organic solvent and optionally isolating the crystalline Form I. In some embodiments, the crystalline Form I is prepared by precipitating and crystallizing the compound of Formula I in a super saturated organic solvent and optionally isolating the crystalline Form I.

Any suitable organic solvent can be used in this regard, such as, for example, water, DMSO, acids, and polar or non-polar solvents, at various strengths or concentrations. Such solvents may include, but are not limited to, tetrahydrofuran, tert-butylmethyl ether, methyl ethyl ketone, heptane, 2-methyl tetrahydrofuran, toluene, anisole, DMSO, water, ethanol, butanol, methanol, dichloromethane, ethyl acetate, acetone, ethyl acetate, dimethylformamide, acetonitrile, dimethyl sulfoxide, propylene carbonate, formic acid, isopropanol, propanol, acetic acid, nitromethane, and a combination thereof. In some embodiments, the organic solvent is selected from tetrahydrofuran, DMSO, tert-butylmethyl ether, methyl ethyl ketone, heptane, 2-methyl tetrahydrofuran, toluene, anisole, ethyl acetate, methanol, water, 2-propanol, ethanol, and a combination thereof. In some embodiments, the water does not have any additional components or solvents added to it. In some embodiments, the organic solvent comprises methyl ethyl ketone and heptane. In some embodiments, the organic solvent comprises tert-butylmethyl ether and heptane. In some embodiments, the organic solvent comprises tetrahydrofuran and heptane. In some embodiments, the organic solvent is tert-butylmethyl ether. In some embodiments, the organic solvent is heptane. In some embodiments, the organic solvent is t-butylmethyl ether. In some embodiments, the organic solvent does not contain water. In some embodiments, the organic solvent contains water.

The crystalline Form I of the compound of Formula I may be identified, characterized, and distinguished from amorphous form using any suitable manner. One skilled in the art will know many different methods of identification and characterization of the crystalline Form I. For example, the crystalline Form I of the compound of Formula I may be identified and characterized based on differences in diffraction, thermal, intensity, and/or spectroscopic properties of the amorphous and crystalline form. Suitable methods include, but are not limited to, X-ray diffractometry, capillary melting point determination, thermogravimetric analysis (TGA), differential scanning calorimetry (DSC), and/or spectroscopic methods.

In some embodiments, the crystalline Form I is precipitated from water. FIGS. 16 and 25 shows an example characterization of Form I using X-ray powder diffraction and DSC. In some embodiments, the crystalline Form I was precipitated from an organic solvent and was characterized by HPLC and microscopy. FIG. 32-34 shows example HPLC chromatograms of the crystalline Form I prepared from different organic solvents.

FIG. 1 shows the X-ray powder diffraction pattern of the amorphous form of the compound of Formula I obtained using organic solvent. In some embodiments, the crystalline Form I is precipitated from supersaturated organic solvent. XRD characterization from supersaturated organic solvent indicates that the crystalline Form I is crystalline material as shown in FIG. 16. DSC thermogram of the crystalline Form I in FIG. 25 also showed different endothermic transitions from the amorphous form of the compound of Formula I, with the last endothermic peak at around 95° C.-98° C.

Figure 8:
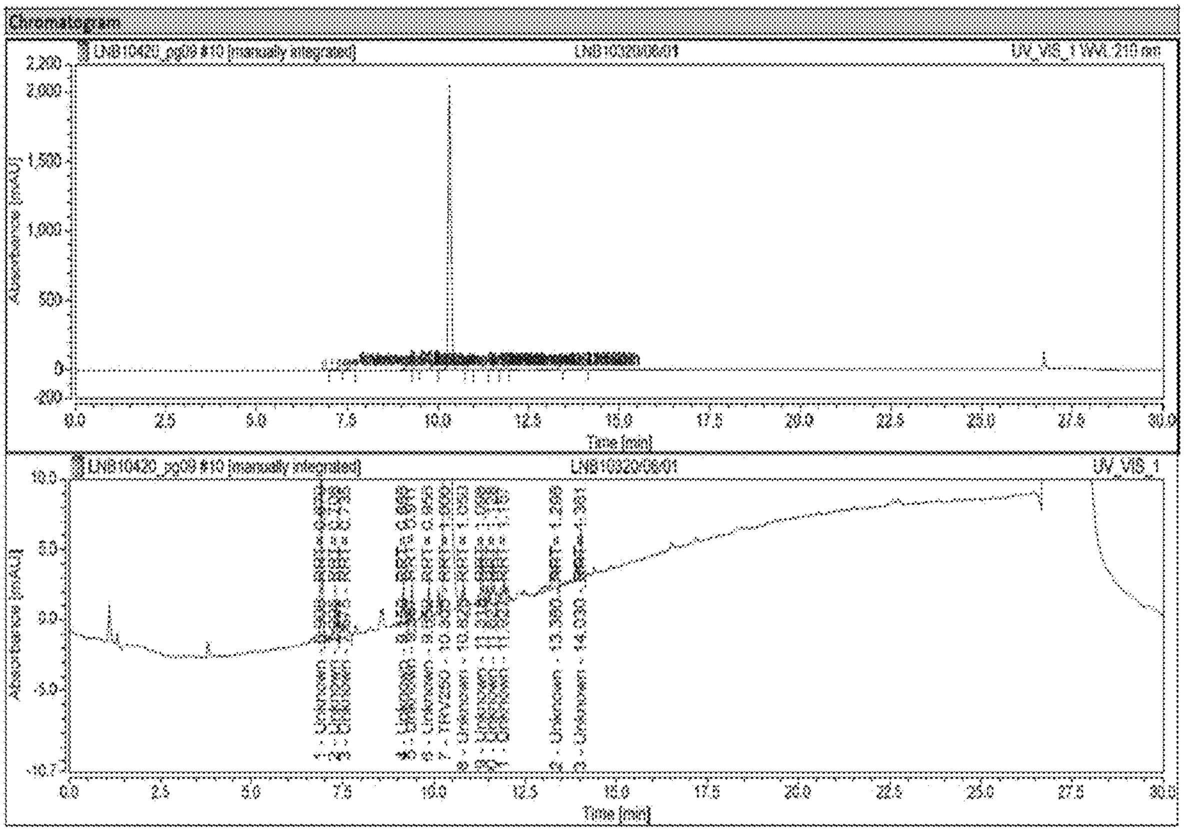
FIG. 8 shows HPLC chromatograms of the amorphous form of the compound of Formula I in free base form.
Figure 9:
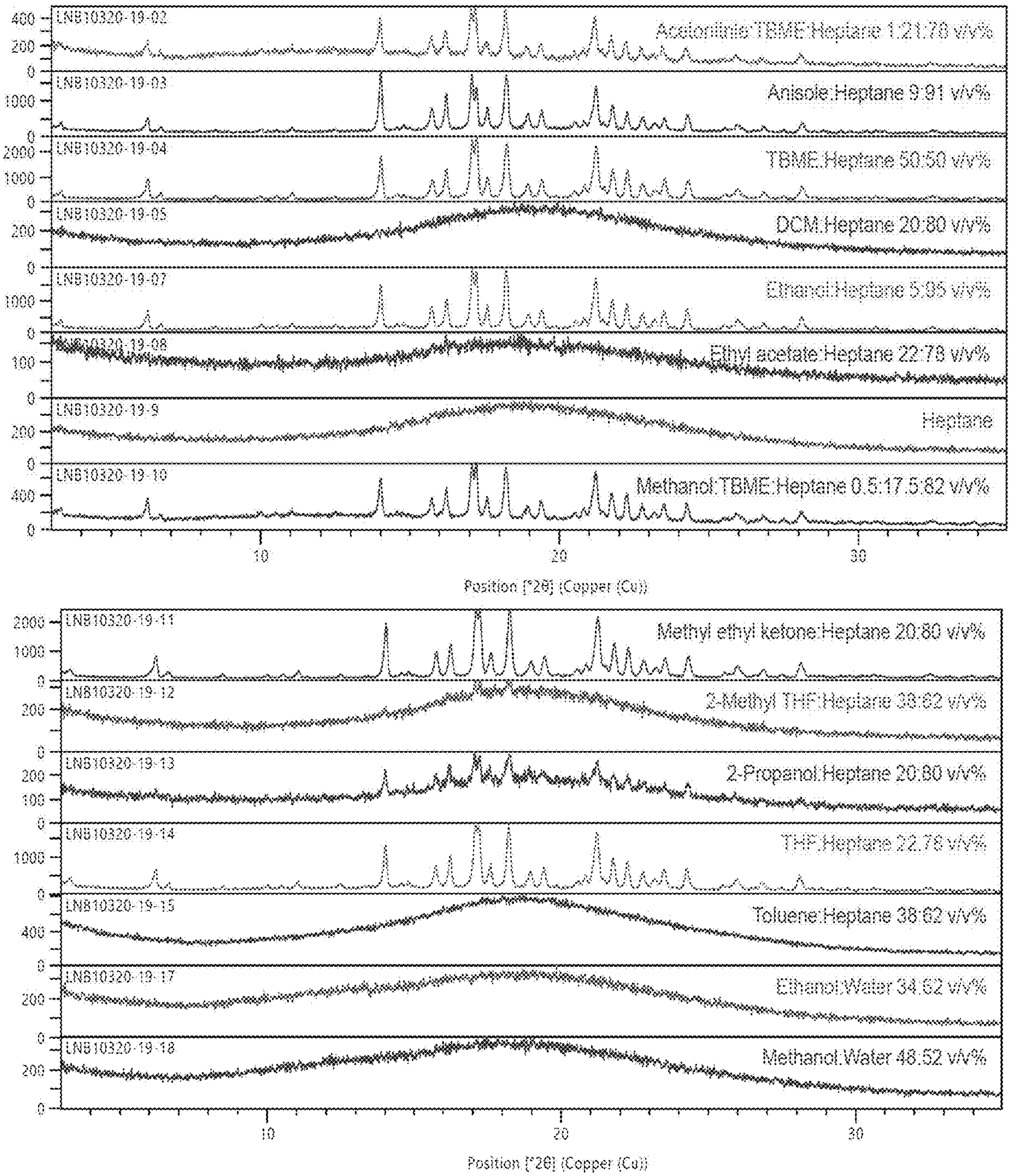
FIG. 9 shows X-ray powder diffraction patterns of the material directly isolated after anti-solvent addition (wet solids).
Figure 10:
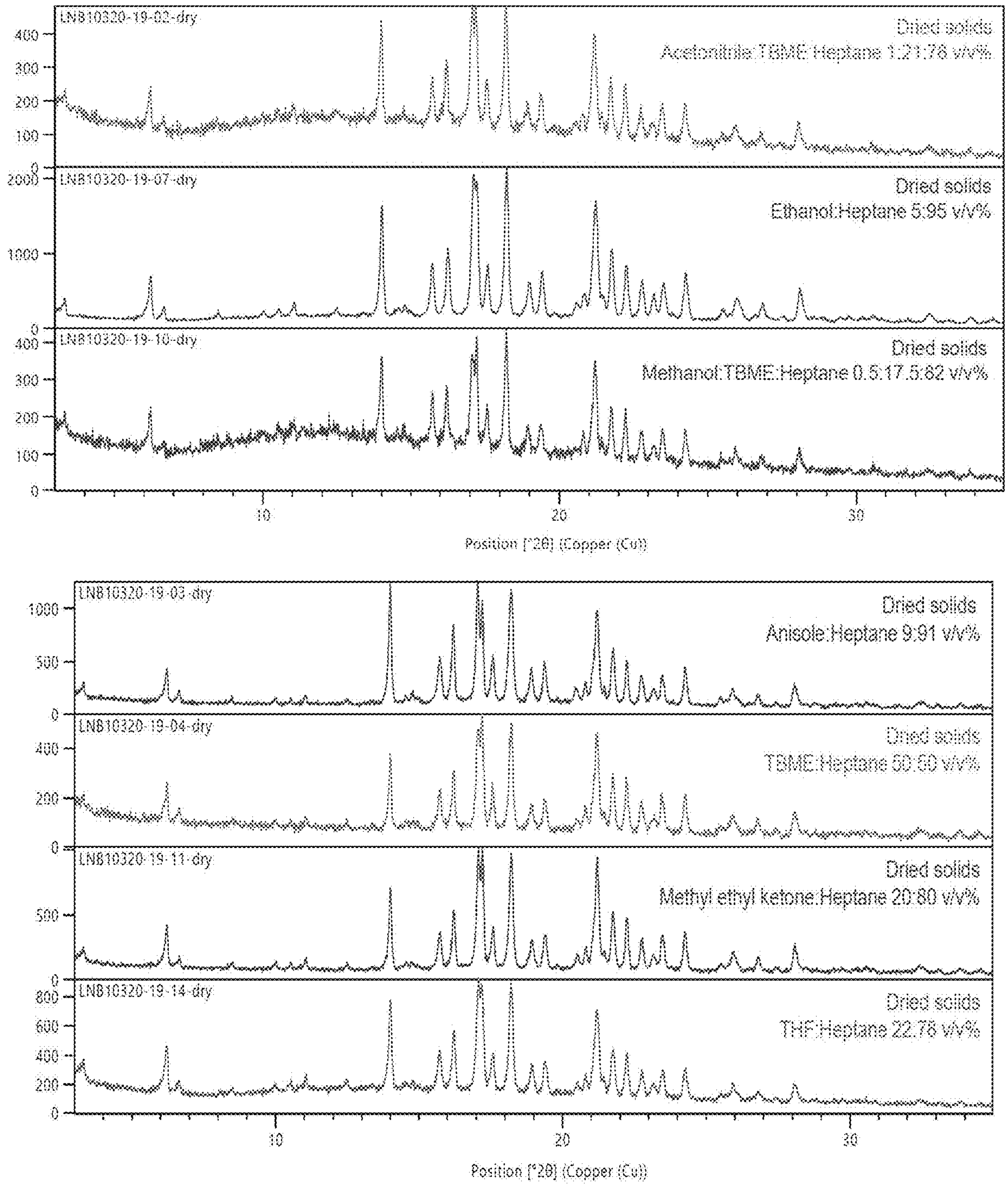
FIG. 10 shows X-ray powder diffraction patterns of the material isolated after anti-solvent addition and after drying under vacuum (dry solids).
Figure 12:
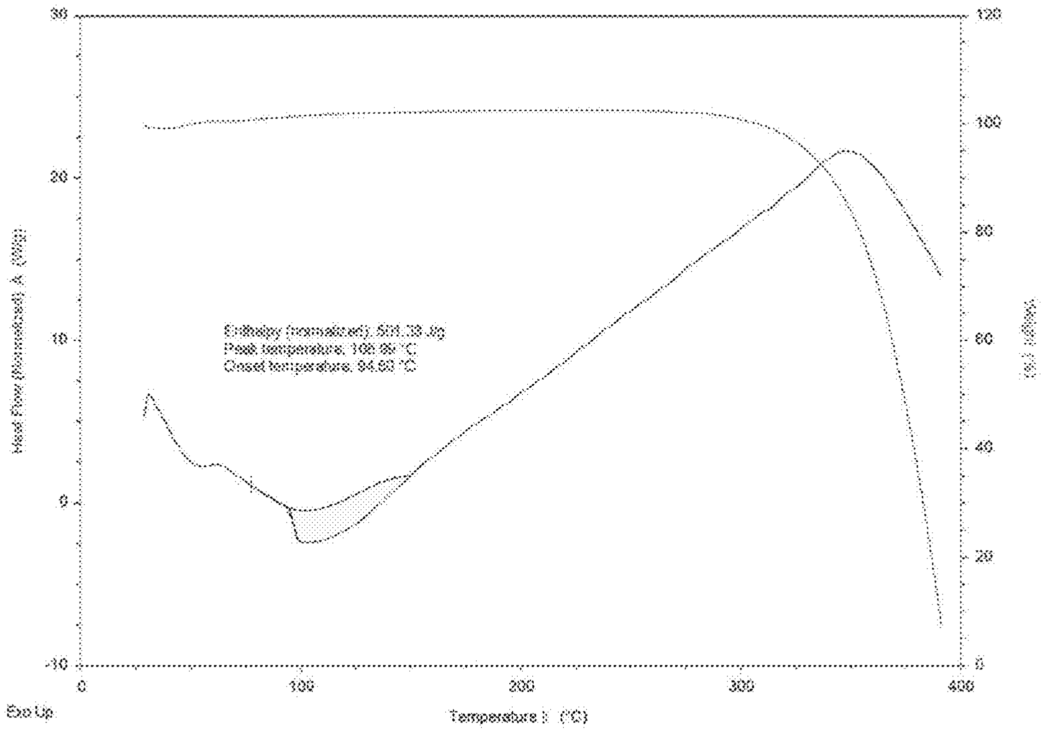
FIG. 12 shows Thermogravimetric/Differential Scanning Calorimetry (TG/DSC) thermogram of the material isolated from tBME:Heptane 50:50 v/v %.
Figure 13:
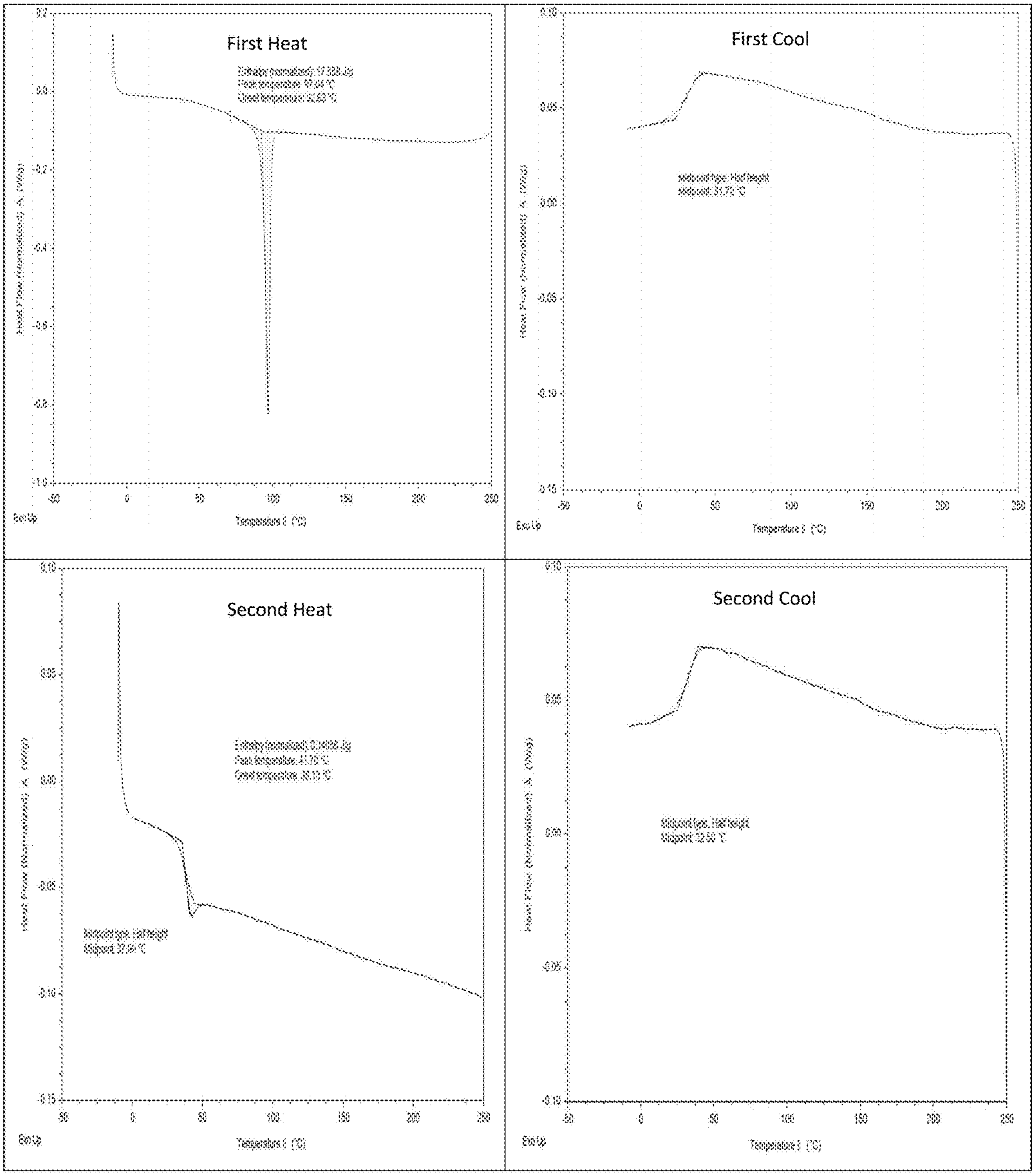
FIG. 13 shows Thermogravimetric/Differential Scanning Calorimetry (TG/DSC) thermogram of the material isolated from MEK:Heptane 20:80 v/v %.

FIGS. 8 and 32 shows exemplary HPLC chromatograms of amorphous and crystalline Form I of the compound of Formula I respectively. Comparing FIG. 32 to FIG. 8, the HPLC chromatograms confirmed that the crystalline form prepared from organic solvent is chemically the same as the compound of Formula I amorphous form. These results demonstrate that Form I is a crystalline form of the compound of Formula I.

Figure 19:
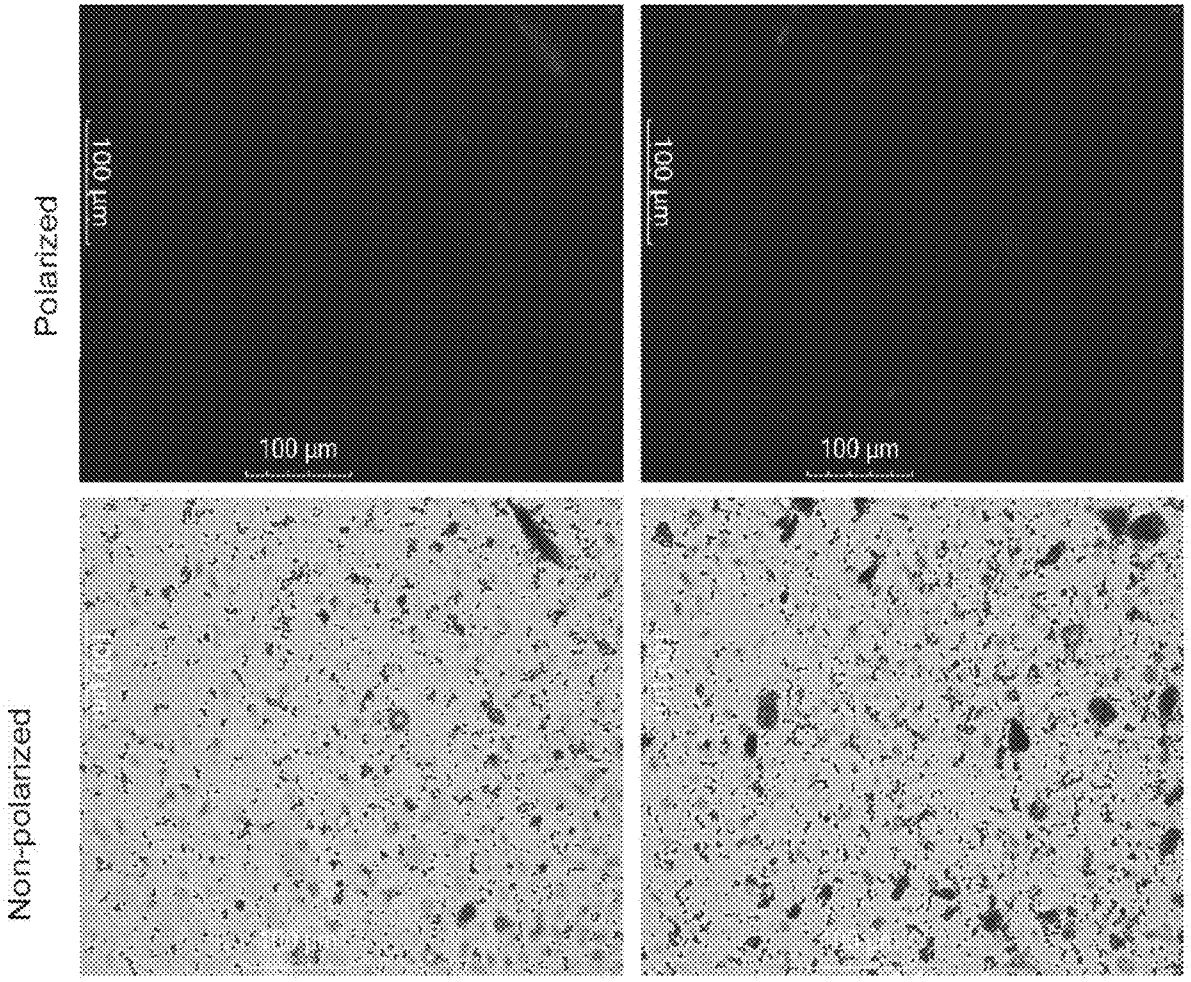
FIG. 19 shows microscopy image and particle size of the crystalline Form I prepared from tBME:Heptane 50:50 v/v % under both polarized and non-polarized light.
Figure 20:
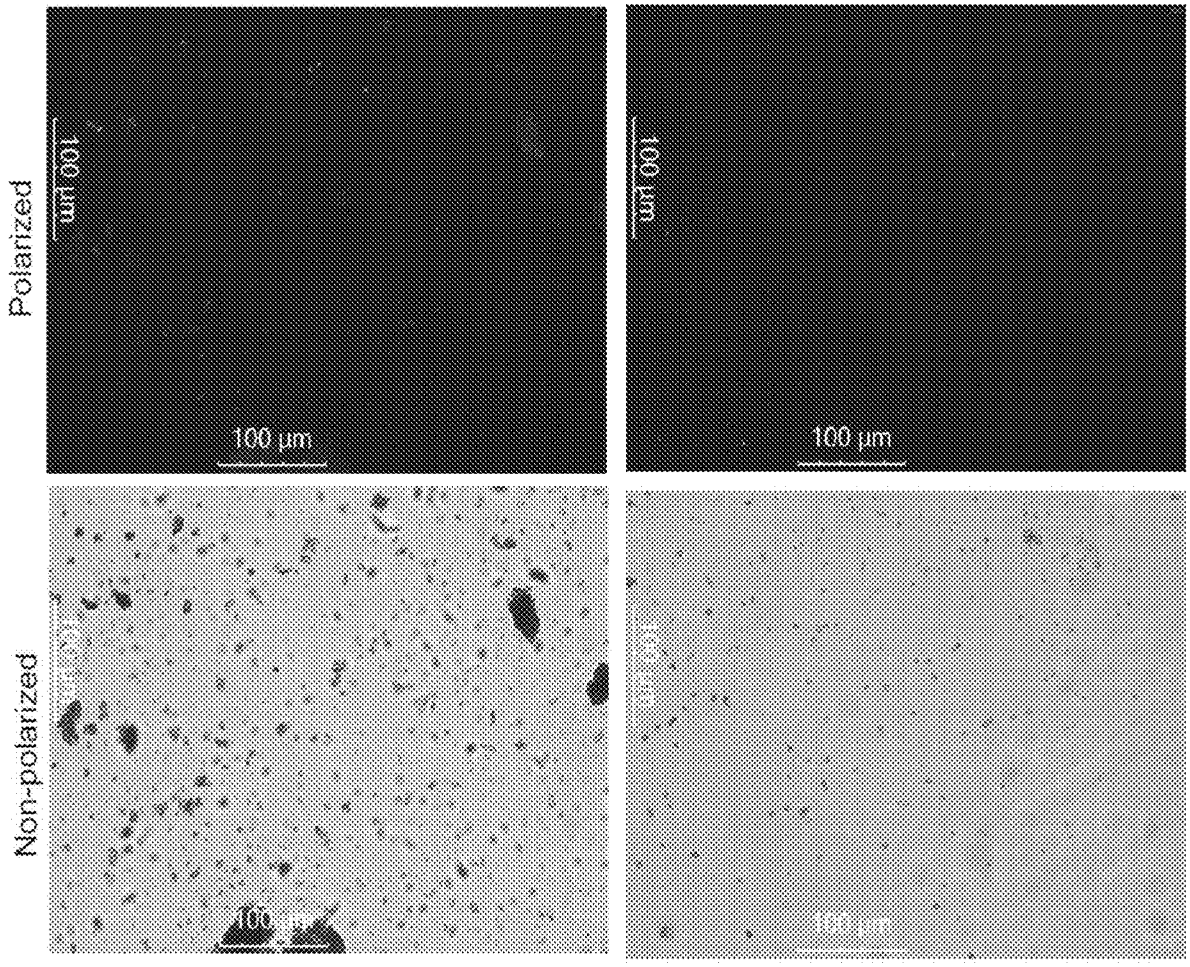
FIG. 20 shows microscopy image and particle size of the crystalline Form I prepared from MEK:Heptane 20:80 v/v % under both polarized and non-polarized light.
Figure 21:
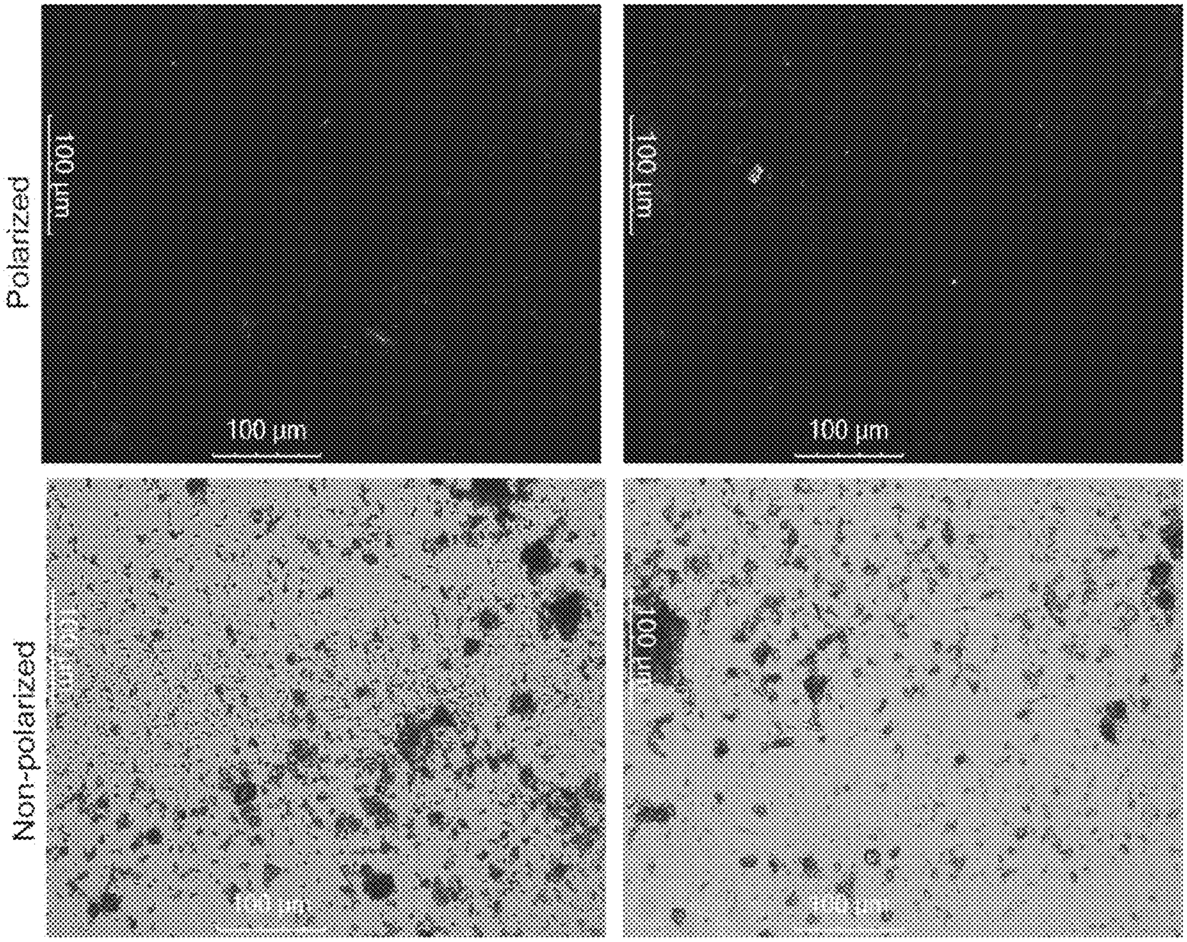
FIG. 21 shows microscopy image and particle size of the crystalline Form I prepared from THF:Heptane 22:78 v/v % under both polarized and non-polarized light.
Figure 22:
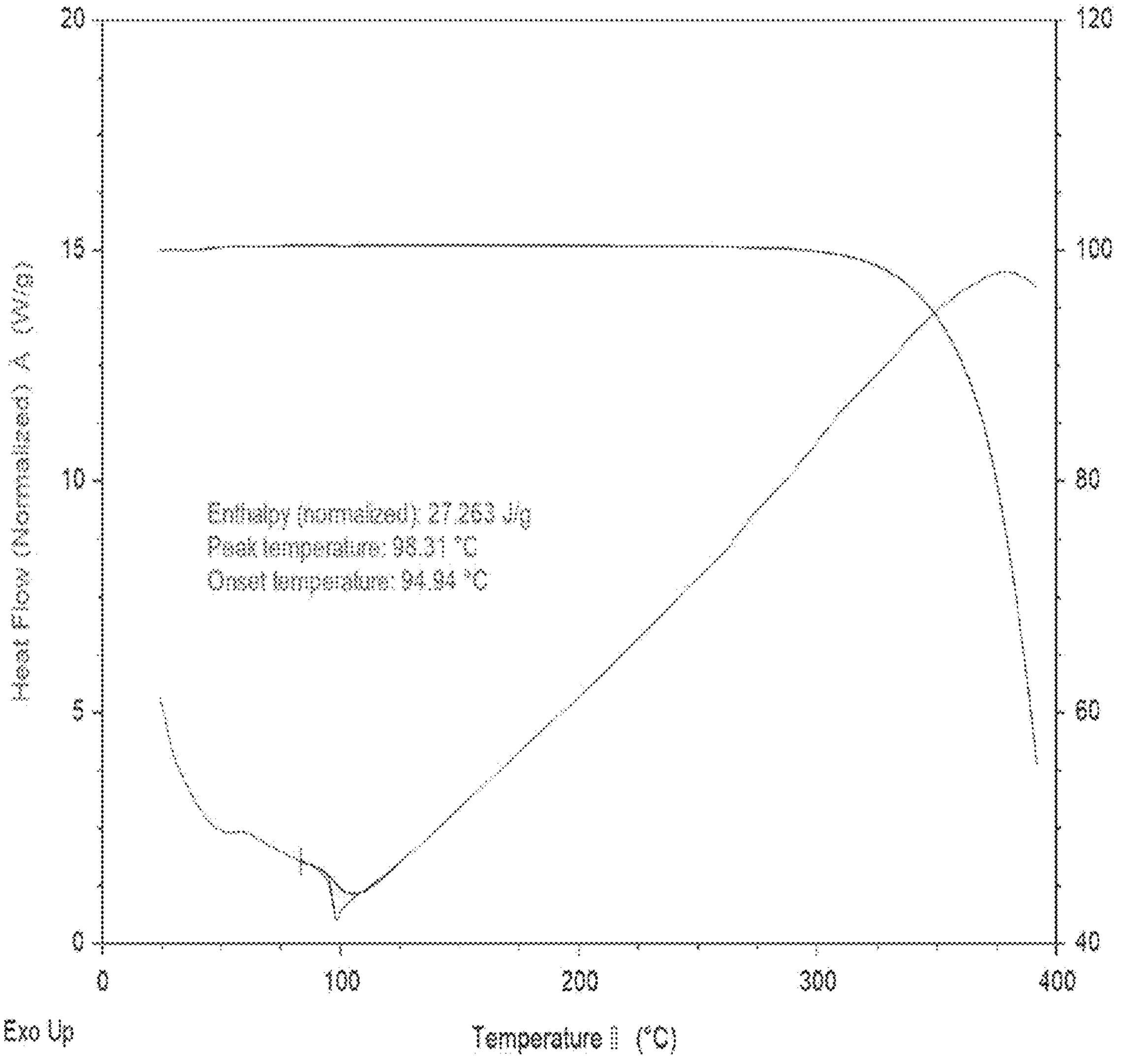
FIG. 22 shows Thermogravimetric/Differential Scanning Calorimetry (TG/DSC) thermogram of the crystalline Form I prepared from tBME:Heptane 50:50 v/v %.
Figure 23:
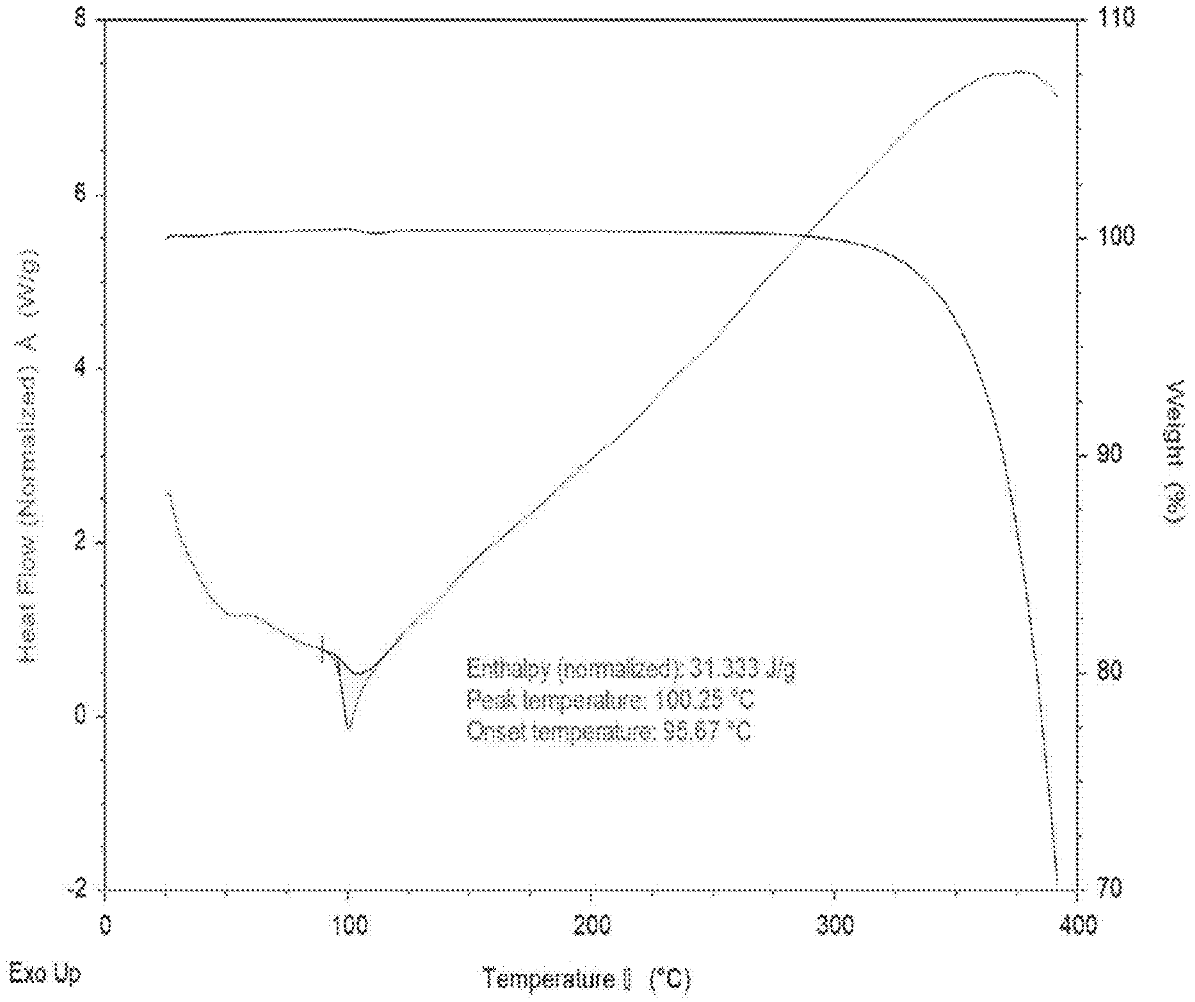
FIG. 23 shows Thermogravimetric/Differential Scanning Calorimetry (TG/DSC) thermogram of the crystalline Form I prepared from MEK:Heptane 20:80 v/v %.
Figure 24:
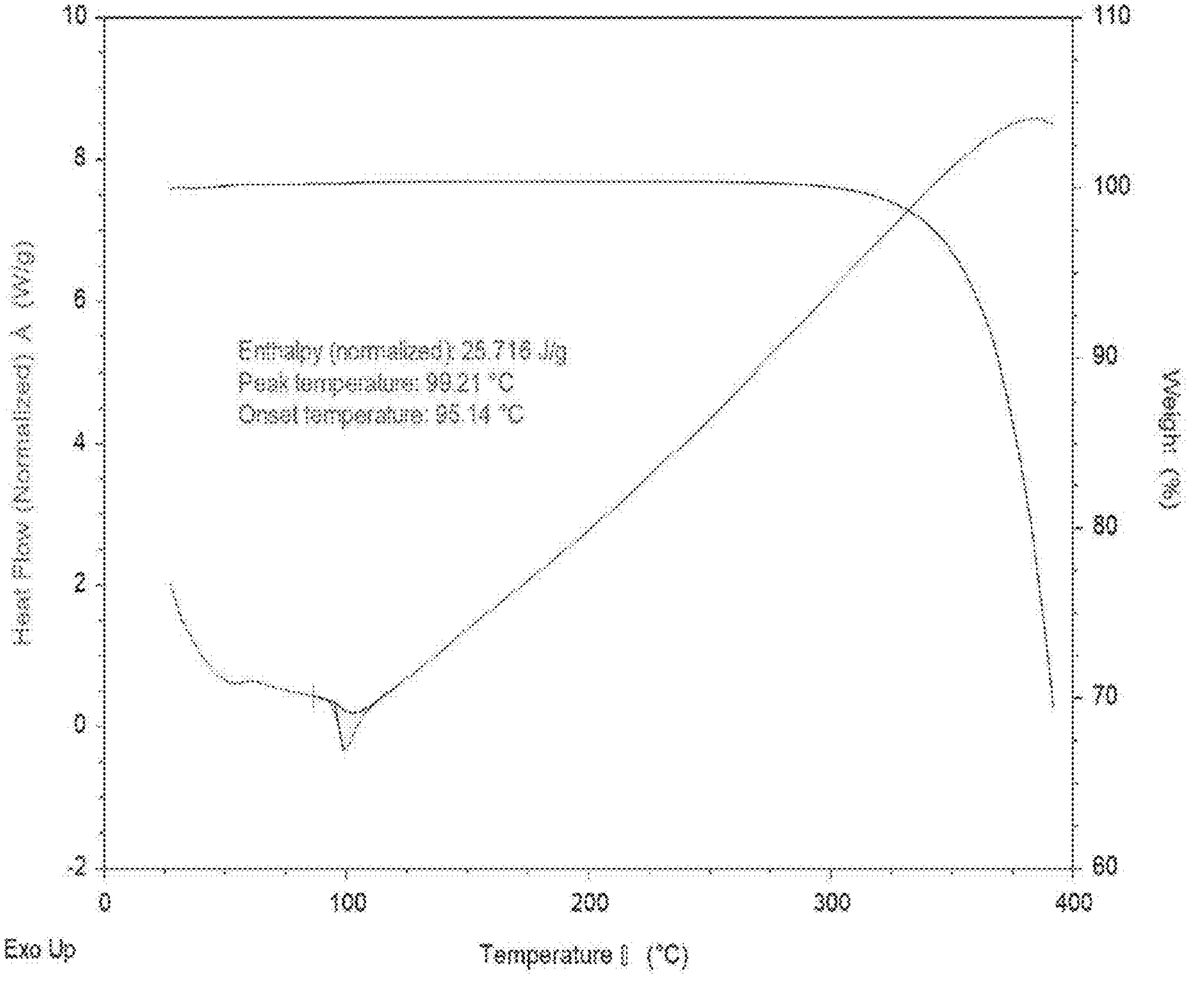
FIG. 24 shows Thermogravimetric/Differential Scanning Calorimetry (TG/DSC) thermogram of the crystalline Form I prepared from THF:Heptane 22:78 v/v %.

The crystalline Form I was further examined using polarized microscopy. FIGS. 19-21 show example microscopy images and particle sizes of crystalline Form I under both polarized and non-polarized light. These results confirmed that Form I was crystalline material as birefringence was observed in the sample under the polarized light in FIGS. 19-21.

In some embodiments, processes for preparing the compound of Formula I are provided. In some embodiments, amorphous form of the compound of Formula I is prepared by precipitating the compound of Formula I and optionally isolating the compound of Formula I. In some embodiments, amorphous form of the compound of Formula I was precipitated from a solution comprising acetone, diethyl ether, methanol, ethanol, 2-propanol, tert-butylmethyl ether, pentane, heptane, acetonitrile, dichloromethane, isopropyl acetate, tetrahydrofuran, or water, or a combination thereof. In some embodiments, amorphous form of the compound of Formula I was precipitated from a solution comprising methanol and tert-butylmethyl ether. In some embodiments, amorphous form of the compound of Formula I was precipitated from a solution comprising methanol and water. In some embodiments, amorphous form of the compound of Formula I was precipitated from a solution comprising acetonitrile and tert-butylmethyl ether. In some embodiments, amorphous form of the compound of Formula I was precipitated from a solution comprising heptane and tert-butylmethyl ether. In some embodiments, amorphous form of the compound of Formula I was precipitated from a solution comprising ethanol and water. In some embodiments, amorphous form of the compound of Formula I was precipitated from a solution comprising 2-propanol and water. In some embodiments, amorphous form of the compound of Formula I was precipitated from a solution comprising acetone and water. In some embodiments, amorphous form of the compound of Formula I was precipitated from a solution comprising tetrahydrofuran and heptane. In some embodiments, amorphous form of the compound of Formula I was precipitated from a solution comprising dichloromethane and heptane. In some embodiments, amorphous form of the compound of Formula I was precipitated from a solution comprising dichloromethane and pentane. In some embodiments, amorphous form of the compound of Formula I was precipitated from a solution comprising dichloromethane and diethyl ether. In some embodiments, amorphous form of the compound of Formula I was precipitated from a solution comprising heptane. In some embodiments, amorphous form of the compound of Formula I was precipitated from a solution comprising tert-butylmethyl ether. In some embodiments, amorphous form of the compound of Formula I was precipitated from a solution comprising tetrahydrofuran.

In some embodiments, processes for preparing a crystalline form of the compound of Formula I, comprising crystallizing the compound of Formula I to form the crystalline Form I and optionally isolating the crystalline Form I of the compound of Formula I are provided.

In some embodiments, provided are processes for preparing a crystalline form of the compound of Formula I, wherein the crystallizing step comprises dissolving the compound of Formula I in an organic solvent to form a solution. In some embodiments, the compound of Formula I can be dissolved in an organic solvent of, for example, without limiting, tert-butylmethyl ether, followed by addition of heptane, wherein the percentage of tert-butylmethyl ether in the resulting solution may be from approximately 95% and 5% v/v. In some embodiments, the percentage of tert-butylmethyl ether in the resulting solution may be approximately 90% v/v and the remainder of the solution approximately is heptane. In some embodiments, the percentage of tert-butylmethyl ether in the resulting solution may be approximately 80% v/v and the remainder of the solution approximately is heptane. In some embodiments, the percentage of tert-butylmethyl ether in the resulting solution may be approximately 70% v/v and the remainder of the solution approximately is heptane. In some embodiments, the percentage of tert-butylmethyl ether in the resulting solution may be approximately 60% v/v and the remainder of the solution approximately is heptane. In some embodiments, the percentage of tert-butylmethyl ether in the resulting solution may be approximately 55% v/v and the remainder of the solution approximately is heptane. In some embodiments, the percentage of tert-butylmethyl ether in the resulting solution may be approximately 50% v/v and the remainder of the solution approximately is heptane. In some embodiments, the percentage of tert-butylmethyl ether in the resulting solution may be approximately 45% v/v and the remainder of the solution approximately is heptane. In some embodiments, the percentage of tert-butylmethyl ether in the resulting solution may be approximately 40% v/v and the remainder of the solution approximately is heptane. In some embodiments, the percentage of tert-butylmethyl ether in the resulting solution may be approximately 35% v/v and the remainder of the solution approximately is heptane. In some embodiments, the percentage of tert-butylmethyl ether in the resulting solution may be approximately 30% v/v and the remainder of the solution approximately is heptane. In some embodiments, the percentage of tert-butylmethyl ether in the resulting solution may be approximately 25% v/v and the remainder of the solution approximately is heptane. In some embodiments, the percentage of tert-butylmethyl ether in the resulting solution may be approximately 20% v/v and the remainder of the solution approximately is heptane. In some embodiments, the percentage of tert-butylmethyl ether in the resulting solution may be approximately 15% v/v and the remainder of the solution approximately is heptane. In some embodiments, the percentage of tert-butylmethyl ether in the resulting solution may be approximately 10% v/v and the remainder of the solution approximately is heptane. In some embodiments, the percentage of tert-butylmethyl ether in the resulting solution may be approximately 5% v/v and the remainder of the solution approximately is heptane.

In some embodiments, the compound of Formula I can be dissolved in an organic solvent of, for example, without limiting, methyl ethyl ketone, followed by addition of heptane, wherein the percentage of methyl ethyl ketone in the resulting solution may be from approximately 95% and 5% v/v. In some embodiments, the percentage of methyl ethyl ketone in the resulting solution may be approximately 90% v/v and the remainder of the solution approximately is heptane. In some embodiments, the percentage of methyl ethyl ketone in the resulting solution may be approximately 80% v/v and the remainder of the solution approximately is heptane. In some embodiments, the percentage of methyl ethyl ketone in the resulting solution may be approximately 70% v/v and the remainder of the solution approximately is heptane. In some embodiments, the percentage of methyl ethyl ketone in the resulting solution may be approximately 60% v/v and the remainder of the solution approximately is heptane. In some embodiments, the percentage of methyl ethyl ketone in the resulting solution may be approximately 55% v/v and the remainder of the solution approximately is heptane. In some embodiments, the percentage of methyl ethyl ketone in the resulting solution may be approximately 50% v/v and the remainder of the solution approximately is heptane. In some embodiments, the percentage of methyl ethyl ketone in the resulting solution may be approximately 45% v/v and the remainder of the solution approximately is heptane. In some embodiments, the percentage of methyl ethyl ketone in the resulting solution may be approximately 40% v/v and the remainder of the solution approximately is heptane. In some embodiments, the percentage of methyl ethyl ketone in the resulting solution may be approximately 35% v/v and the remainder of the solution approximately is heptane. In some embodiments, the percentage of methyl ethyl ketone in the resulting solution may be approximately 30% v/v and the remainder of the solution approximately is heptane. In some embodiments, the percentage of methyl ethyl ketone in the resulting solution may be approximately 25% v/v and the remainder of the solution approximately is heptane. In some embodiments, the percentage of methyl ethyl ketone in the resulting solution may be approximately 20% v/v and the remainder of the solution approximately is heptane. In some embodiments, the percentage of methyl ethyl ketone in the resulting solution may be approximately 15% v/v and the remainder of the solution approximately is heptane. In some embodiments, the percentage of methyl ethyl ketone in the resulting solution may be approximately 10% v/v and the remainder of the solution approximately is heptane. In some embodiments, the percentage of methyl ethyl ketone in the resulting solution may be approximately 5% v/v and the remainder of the solution approximately is heptane.

In some embodiments, the compound of Formula I can be dissolved in an organic solvent of, for example, without limiting, tetrahydrofuran, followed by addition of heptane, wherein the percentage of tetrahydrofuran in the resulting solution may be from approximately 95% and 5% v/v. In some embodiments, the percentage of tetrahydrofuran in the resulting solution may be approximately 90% v/v and the remainder of the solution approximately is heptane. In some embodiments, the percentage of tetrahydrofuran in the resulting solution may be approximately 80% v/v and the remainder of the solution approximately is heptane. In some embodiments, the percentage of tetrahydrofuran in the resulting solution may be approximately 70% v/v and the remainder of the solution approximately is heptane. In some embodiments, the percentage of tetrahydrofuran in the resulting solution may be approximately 60% v/v and the remainder of the solution approximately is heptane. In some embodiments, the percentage of tetrahydrofuran in the resulting solution may be approximately 55% v/v and the remainder of the solution approximately is heptane. In some embodiments, the percentage of tetrahydrofuran in the resulting solution may be approximately 50%/v/v and the remainder of the solution approximately is heptane. In some embodiments, the percentage of tetrahydrofuran in the resulting solution may be approximately 45% v/v and the remainder of the solution approximately is heptane. In some embodiments, the percentage of tetrahydrofuran in the resulting solution may be approximately 40% v/v and the remainder of the solution approximately is heptane. In some embodiments, the percentage of tetrahydrofuran in the resulting solution may be approximately 35% v/v and the remainder of the solution approximately is heptane. In some embodiments, the percentage of tetrahydrofuran in the resulting solution may be approximately 30% v/v and the remainder of the solution approximately is heptane. In some embodiments, the percentage of tetrahydrofuran in the resulting solution may be approximately 25% v/v and the remainder of the solution approximately is heptane. In some embodiments, the percentage of tetrahydrofuran in the resulting solution may be approximately 24% v/v and the remainder of the solution approximately is heptane. In some embodiments, the percentage of tetrahydrofuran in the resulting solution may be approximately 23% v/v and the remainder of the solution approximately is heptane. In some embodiments, the percentage of tetrahydrofuran in the resulting solution may be approximately 22% v/v and the remainder of the solution approximately is heptane. In some embodiments, the percentage of tetrahydrofuran in the resulting solution may be approximately 21% v/v and the remainder of the solution approximately is heptane. In some embodiments, the percentage of tetrahydrofuran in the resulting solution may be approximately 20% v/v and the remainder of the solution approximately is heptane. In some embodiments, the percentage of tetrahydrofuran in the resulting solution may be approximately 15% v/v and the remainder of the solution approximately is heptane. In some embodiments, the percentage of tetrahydrofuran in the resulting solution may be approximately 10% v/v and the remainder of the solution approximately is heptane. In some embodiments, the percentage of tetrahydrofuran in the resulting solution may be approximately 5% v/v and the remainder of the solution approximately is heptane.

Additionally, any suitable organic solvent can be used in this regard, such as, for example, water, DMSO, acids, and polar or non-polar solvents, at various strengths or concentrations. Such solvents may include, but are not limited to, tetrahydrofuran, tert-butylmethyl ether, methyl ethyl ketone, heptane, 2-methyl tetrahydrofuran, toluene, anisole, DMSO, water, ethanol, butanol, methanol, dichloromethane, ethyl acetate, acetone, ethyl acetate, dimethylformamide, acetonitrile, dimethyl sulfoxide, propylene carbonate, formic acid, isopropanol, propanol, acetic acid, nitromethane, and a combination thereof. In some embodiments, the solvent is selected from tetrahydrofuran, DMSO, tert-butylmethyl ether, methyl ethyl ketone, heptane, 2-methyl tetrahydrofuran, toluene, anisole, ethyl acetate, methanol, water, 2-propanol, ethanol, and a combination thereof.

Precipitates from, for example, but not limited to, the solutions described herein, including, but not limited to, a solution of tert-butylmethyl ether and heptane, a solution of methyl ethyl ketone and heptane, and a solution of tetrahydrofuran and heptane produce precipitate showing the same XRD pattern as the amorphous form of the compound of Formula I. The results described herein demonstrate that the precipitates contain amorphous, mostly amorphous, a mixture of amorphous and crystalline forms, one or more crystalline forms, or a mixture of amorphous and one or more crystalline forms. Each of the preceding are considered as separate embodiments.

In some embodiments, the precipitate of the crystalline Form I from, for example, but not limited to, a solution of tert-butylmethyl ether and heptane, a solution of methyl ethyl ketone and heptane, or a solution of tetrahydrofuran and heptane may comprise amorphous, mostly amorphous, a mixture of amorphous and crystalline forms, one or more crystalline forms, or a mixture of amorphous and one or more crystalline forms. Each of which is considered as a separate embodiment.

In some embodiments, a precipitate comprising between about 50:50 and 99:1 the crystalline Form I to amorphous form of the compound of Formula I is provided. In some embodiments, the precipitate may comprise amorphous form of the compound of Formula I. In some embodiments, for example, the precipitate may comprise mostly amorphous form of the compound of Formula I at about 99% to about 1% by weight, ranging from about less than 90%, less than 80%, less than 70%, less than 60%, less than 40%, less than 30%, less than 20%, less than 10%, less than 5%, less than 1%, less than 0.50%, less than 0.25% by weight.

In some embodiments, the precipitate may comprise mostly crystalline the compound of Formula I at about 99% to about 1% by weight, ranging from about less than 90%, less than 80%, less than 70%, less than 60%, less than 40%, less than 30%, less than 20%, less than 10%, less than 5%, less than 1%, less than 0.50%, less than 0.25% by weight. In some other embodiments, for example, the precipitate may comprise one or more crystalline forms of the compound of Formula I.

In some embodiments, the precipitate may comprise a mixture of one or more crystalline forms of the compound of Formula I and amorphous form of the compound of Formula I. For example, the precipitate may comprise crystalline the compound of Formula I at about 99% to about 1% by weight, ranging from about less than 90%, less than 80%, less than 70%, less than 60%, less than 40%, less than 30%, less than 20%, less than 10%, less than 5%, less than 10%, less than 0.50%, or less than 0.25% by weight of the mixture. Alternatively, the precipitate may comprise amorphous form of the compound of Formula I at about 99% to about 1% by weight, ranging from about less than 90%, less than 80%, less than 70%, less than 60%, less than 40%, less than 30%, less than 20%, less than 10%, less than 5%, less than 1%, less than 0.50%, or less than 0.25% by weight of the mixture.

In some embodiments, provided are processes for preparing a crystalline form of the compound of Formula I, wherein the crystallizing step further comprises heating the solution of the compound of Formula I in the organic solvent. In some embodiments, the solution is heated to at least, or about, 10, 20, 30, 40, 50, or 60° C. before being cooled or allowed to cool to ambient temperature or a specific temperature. In some embodiments, the solution is heated to about 10-20, 10-30, 10-40, 10-50, 20-30, 20-40, 20-50, 20-60, 30-40, 30-50, 30-60, 40-50, 40-60, 50-60, 25-45, 35-45, or 35-50, 45-55, or 45-60° C. or any temperature between the respective ranges. In some embodiments, the solution is heated to about 40° C. In some embodiments, the solution is heated at given temperature for about 0.5 to about 2 hours, about 1 to about 2 hours, about 0.5 to about 1.5 hours, or about 1 to about 1.5 hours. In some embodiments, the solution is heated at given temperature for about 0.5 hour, 1 hour, 1.5 hours, 2 hours, 2.5 hours, 3 hours, 3.5 hours, 4 hours, 4.5 hours, or 5 hours. In some embodiments, the solution is heated at about 40° C. for about 0.5 to about 2 hours, about 1 to about 2 hours, about 0.5 to about 1.5 hours, about 1 to about 1.5 hours, or any temperature between the respective ranges. In some embodiments, the solution is heated at about 40° C. for about 0.5 hour, 1 hour, 1.5 hours, 2 hours, 2.5 hours, 3 hours, 3.5 hours, 4 hours, 4.5 hours, or 5 hours. In some embodiments, the solution is heated at about 40° C. for about 0.5 hour. In some embodiments, the solution is heated at about 40° C. for 1.5 hours. In some embodiments, the solution is heated at about 40° C. for 2 hours. In some embodiments, the solution is heated at about 40° C. for 2.5 hours. In some embodiments, the solution is heated at about 40° C. for 3 hours. In some embodiments, the solution is heated at about 40° C. for 3.5 hours. In some embodiments, the solution is heated at about 40° C. for 4 hours. In some embodiments, the solution is heated at about 40° C. for 4.5 hours. In some embodiments, the solution is heated at about 40° C. for 5 hours. In some embodiments, the solution was stirred at about 40° C. for about 1 hour.

In some embodiments, provided are processes for preparing a crystalline form of the compound of Formula I, wherein the crystallizing step further comprises cooling the heated solution to ambient temperature. In some embodiments, ambient temperature is 20-25° C. In some embodiments, the solution is cooled to 10-20° C. In some embodiments, the heated solution is cooled at a rate of about 0.5° C./min. In some embodiments, the heated solution is cooled at a rate of about 1° C./min. In some embodiments, the heated solution is cooled at a rate of about 1.5° C./min. In some embodiments, the heated solution is cooled at a rate of about 2° C./min. In some embodiments, the heated solution is cooled at a rate of about 2.5° C./min. In some embodiments, the heated solution is cooled at a rate of about 3° C./min. In some embodiments, the heated solution is cooled at a rate of about 3.5° C./min. In some embodiments, the heated solution is cooled at a rate of about 4° C./min.

In some embodiments, the crystal form is precipitated at a temperature of about 5 to about 40° C., about 5 to about 35° C., about 5 to about 30° C., about 5 to about 25° C., about 5 to about 20° C., about 5 to about 15° C., about 5 to about 10° C., 10 to about 40° C., about 10 to about 35° C., about 10 to about 30° C., about 10 to about 25° C., about 10 to about 20° C., about 10 to about 15° C., 15 to about 40° C., about 15 to about 35° C., about 15 to about 30° C., about 15 to about 25° C., about 15 to about 20° C., 20 to about 40° C., about 20 to about 35° C., about 20 to about 30° C., about 20 to about 25° C., 30 to about 40° C., about 30 to about 35° C., about 35 to about 40° C., or any temperature between the respective ranges. In some embodiments, the precipitates are allowed to form for about, or at least, 1, 2, 3, 4, 5, 6, 7, 8, 9, 10, 12, 13, 14, 15, 16, 17, 18, 19, 20, 21, 22, 23, or 24 hours. In some embodiments, the precipitates are allowed to form for about 2 to about 24, about 2 to about 17, about 2 to about 12, about 2 to about 10, about 2 to about 8, about 2 to about 6, about 2 to about 4, about 4 to about 24, about 4 to about 17, about 2 to about 12, about 4 to about 10, about 4 to about 8, about 4 to about 6, about 5 to about 24, about 5 to about 17, about 5 to about 12, about 5 to about 10, about 5 to about 8, about 5 to about 6, about 6 to about 24, about 6 to about 18, about 6 to about 12, about 6 to about 10, about 6 to about 8, about 8 to about 24, about 8 to about 17, about 8 to about 12, or about 8 to about 10 hours.

In some embodiments, provided are processes for preparing a crystalline form of the compound of Formula I, wherein the crystallizing step further comprises adding one or more anti-solvents to the cooled solution to form a mixture. In some embodiments, provided are processes for preparing a crystalline form of the compound of Formula I, wherein the crystallizing step comprises further comprising adding one anti-solvent to the cooled solution to form a mixture. In some embodiments, the anti-solvent is as defined in the embodiments as described herein. In some embodiments, the anti-solvent is heptane. In some embodiments, the anti-solvent is heptane. In some embodiments, the anti-solvent is t-butylmethyl ether. In some embodiments, the anti-solvent is water. In some embodiments, the anti-solvent is a combination of heptane and t-butylmethyl ether as described in the embodiments as described herein. In some embodiments, an additional volume of the anti-solvent is added once the solution.

In some embodiments, provided are processes for preparing a crystalline form of the compound of Formula I, wherein the crystallizing step further comprises heating the mixture resulting from addition of the anti-solvent to the solution comprising the compound of Formula I. In some embodiments, the mixture is heated to at least, or about, 10, 20, 30, 40, 50, or 60° C. before being cooled or allowed to cool to ambient temperature or a specific temperature. In some embodiments, the solution is heated to about 10-20, 10-30, 10-40, 10-50, 20-30, 20-40, 20-50, 20-60, 30-40, 30-50, 30-60, 40-50, 40-60, 50-60, 25-45, 35-45, or 35-50, 45-55, or 45-60° C. or any temperature between the respective ranges. In some embodiments, the solution is heated to about 40° C.

In some embodiments, provided are processes for preparing a crystalline form of the compound of Formula I, wherein the crystallizing step comprises further comprising temperature cycling of the mixture resulting from addition of the anti-solvent to the solution comprising the compound of Formula I. In some embodiments, the temperature cycling of the mixture is between 40° C. and 5° C. In some embodiments, the mixture is cooled at a rate of about 0.5° C./min. In some embodiments, the mixture is cooled at a rate of about 1° C./min. In some embodiments, the mixture is cooled at a rate of about 1.5° C./min. In some embodiments, the mixture is cooled at a rate of about 2° C./min. In some embodiments, the mixture is cooled at a rate of about 2.5° C./min. In some embodiments, the mixture is cooled at a rate of about 3° C./min. In some embodiments, the mixture is cooled at a rate of about 3.5° C./min. In some embodiments, the mixture is cooled at a rate of about 4° C./min. In some embodiments, the mixture is heated at a rate of about 0.5° C./min. In some embodiments, the mixture is heated at a rate of about 1° C./min. In some embodiments, the mixture is heated at a rate of about 1.5° C./min. In some embodiments, the mixture is heated at a rate of about 2° C./min. In some embodiments, the mixture is heated at a rate of about 2.5° C./min. In some embodiments, the mixture is heated at a rate of about 3° C./min. In some embodiments, the mixture is heated at a rate of about 3.5° C./min. In some embodiments, the mixture is heated at a rate of about 4° C./min. In some embodiments, the mixture is held at about 40° C. for about 0.5, 1, 1.5, 2, 2.5, 3, 3.5, 4, 4.5, or 5 hours during each cycle. In some embodiments, the mixture is held at about 40° C. for about 1 hour. In some embodiments, the temperature cycling is maintained for about 5, 6, 7, 8, 9, 10, 12, 13, 14, 15, 16, 17, 18, 19, 20, 21, 22, 23, or 24 hours. In some embodiments, the temperature cycling is maintained for about 17 hours.

In some embodiments, provided are processes for preparing a crystalline form of the compound of Formula I, wherein the crystallizing step comprises further comprising settling the mixture at about 5° C. after the temperature recycling.

In some embodiments, provided are processes for preparing a crystalline form of the compound of Formula I, wherein the isolating step comprises centrifuging the crystallized compound of Formula I to isolate the crystalline form.

In some embodiments, provided are processes for preparing a crystalline form of the compound of Formula I further comprising drying the precipitate of the compound of Formula I. In some embodiments, the precipitate is in a crystalline form. In some embodiments, provided are processes for preparing a crystalline form of the compound of Formula I, wherein the crystallizing step comprises further comprising drying the crystalline form of the compound of Formula I. In some embodiments, the crystalline form is dried under vacuum. In some embodiments, the crystalline form is dried at a temperature of about 30° C. to about 50° C., about 35° C. to about 50° C., about 30° C. to about 45° C., about 35° C. to about 45° C., or about 40° C. to about 45° C. In some embodiments, the crystalline form is dried at a temperature of about 30° C., about 35° C., about 40° C., about 45° C. or about 50° C. For the avoidance of doubt, the drying can at a specific temperature can be performed under vacuum. In some embodiments, the dried material is also lyophilized.

In some embodiments, the precipitations and crystallization steps described above can be repeated. In some embodiments, the process is repeated one, two, or three times.

Pharmaceutical Compositions/Formulations

Embodiments described herein can be used in pharmaceutical compositions and can be formulated by standard techniques using one or more physiologically acceptable carriers or excipients. In some embodiments, the formulations may contain a buffer and/or a preservative. The crystalline Form I and their physiologically acceptable salts, anhydrates, hydrates and/or solvates, can be formulated for administration by any suitable route, including via inhalation, topically, nasally, orally, parenterally (for example, intravenously, intraperitoneally, intravesically or intrathecally) or rectally in a vehicle comprising one or more pharmaceutically acceptable carriers, the proportion of which is determined by the route of administration and standard biological practice. Other routes of administration are also described herein and can be used as well.

In some embodiments, pharmaceutical compositions are provided comprising effective amounts of the crystalline Form I with, for example, pharmaceutically acceptable diluents, preservatives, solubilizers, emulsifiers, adjuvants and/or other carriers. Such compositions are known to one skilled in the art and the compositions can be formulated using standard techniques. For example, diluents of various buffer content such as, but not limited to, TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as detergents and solubilizing agents (e.g., surfactants such as Pluronics, Tween 20, Tween 80 (Polysorbate 80), Cremophor, polyols such as polyethylene glycol, propylene glycol, etc.), anti-oxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes may be used. Hyaluronic acid may also be used. Such compositions can be employed to influence the physical state, stability, rate of in vivo release, and rate of in vivo clearance of a composition comprising the crystalline Form I as described herein. See, e.g., Remington's Pharmaceutical Sciences, 18th Ed. (1990, Mack Publishing Co., Easton, Pa. 18042) pages 1435-1712 which are herein incorporated by reference. Where a buffer is to be included in the formulations, the buffer can be, for example, but not limited to, sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, or mixtures thereof. Each buffer can be used independently or in combination with another buffer. In some embodiments, the buffer is glycylglycine, sodium dihydrogen phosphate, disodium hydrogen phosphate, sodium phosphate or mixtures thereof.

Where a pharmaceutically acceptable preservative is to be included in the formulations, the preservative can be, but is not limited to, phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. In some embodiments, the preservative is phenol and/or m-cresol.

In some embodiments, the preservative is present in a concentration from about 0.1 mg/ml to about 100 mg/ml, more preferably in a concentration from about 0.1 mg/ml to about 50 mg/ml, about 0.1 mg/ml to about 25 mg/ml. In some embodiments, the preservative is present in a concentration from about 0.1 mg/ml to about 10 mg/ml.

The use of a preservative in pharmaceutical compositions is well known to the skilled person. For convenience, reference is made to Remington: The Science and Practice of Pharmacy, 19th edition, 1995.

In some embodiments, the formulation may further comprise a chelating agent where the chelating agent may be salts of ethlenediaminetetraacetic acid (EDTA), citric acid, and aspartic acid, and mixtures thereof.

In some embodiments, the chelating agent is present in a concentration from 0.1 mg/ml to 10 mg/ml, particularly in a concentration from 0.1 mg/ml to 5 mg/ml. In some embodiments, the chelating agent is present in a concentration from 0.1 mg/ml to 2 mg/ml. In some embodiments, the chelating agent is present in a concentration from 2 mg/ml to 5 mg/ml.

The use of a chelating agent in pharmaceutical compositions is well known to the skilled person. For convenience, reference is made to Remington: The Science and Practice of Pharmacy, 19th edition, 1995.

In some embodiments, the formulation may further comprise a stabilizer selected from the group of high molecular weight polymers or low molecular compounds where such stabilizers include, but are not limited to, polyethylene glycol (e.g., PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. In some embodiments, the stabilizer is L-histidine, imidazole, arginine, or any combination thereof.

In some embodiments, the high molecular weight polymer is present in a concentration from 0.1 mg/ml to 100 mg/ml, in a concentration from 0.1 mg/ml to 50 mg/ml. In some embodiments, the high molecular weight polymer is present in a concentration from 0.1 mg/ml to 5 mg/ml. In some embodiments, the high molecular weight polymer is present in a concentration from 5 mg/ml to 10 mg/ml. In some embodiments, the high molecular weight polymer is present in a concentration from 10 mg/ml to 20 mg/mi. In some embodiments, the high molecular weight polymer is present in a concentration from 20 mg/ml to 30 mg/ml. In some embodiments, the high molecular weight polymer is present in a concentration from 30 mg/ml to 50 mg/ml.

In some embodiments, the low molecular weight polymer is present in a concentration from 0.1 mg/ml to 100 mg/ml. In some embodiments, the low molecular weight polymer is present in a concentration from 0.1 mg/ml to 50 mg/ml. In some embodiments, the low molecular weight polymer is present in a concentration from 0.1 mg/ml to 5 mg/ml. In some embodiments, the low molecular weight polymer compound is present in a concentration from 5 mg/ml to 10 mg/ml. In some embodiments, the low molecular weight polymer is present in a concentration from 10 mg/ml to 20 mg/ml. In some embodiments, the low molecular weight polymer is present in a concentration from 20 mg/ml to 30 mg/ml. In some embodiments, the low molecular weight polymer is present in a concentration from 30 mg/ml to 50 mg/ml. In some embodiments, the low molecular weight polymer is present in a concentration from 50 mg/ml to 60 mg/ml. In some embodiments, the low molecular weight polymer is present in a concentration from 60 mg/ml to 80 mg/ml. In some embodiments, the low molecular weight polymer is present in a concentration from 80 mg/ml to 100 mg/ml.

The use of a stabilizer in pharmaceutical compositions is well known to the skilled person. For convenience, reference is made to Remington: The Science and Practice of Pharmacy, 19th edition, 1995.

In some embodiments, the formulation may comprise a surfactant where a surfactant can be a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g., Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g., 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g., lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the positively charged DODAC, DOTMA, DCP, BISHOP, lysophosphatidylserine and lysophosphatidylthreonine, zwitterionic surfactants (e.g., N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g., cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g., sodium tauro-dihydrofusidate etc.), long-chain fatty acids and salts thereof C6-C12 (e.g., oleic acid and caprylic acid), acylcarnitines and derivatives, $N_\alpha$-acylated derivatives of lysine, arginine or histidine, or side-chain acylated derivatives of lysine or arginine, $N_\alpha$-acylated derivatives of dipeptide comprising any combination of lysine, arginine or histidine and a neutral or acidic amino acid, $N_\alpha$-acylated derivative of a tripeptide comprising any combination of a neutral amino acid and two charged amino acids, imidazoline derivatives, or any mixture thereof.

The use of a surfactant in pharmaceutical compositions is well-known to the skilled person. For convenience, reference is made to Remington: The Science and Practice of Pharmacy, 19th edition, 1995.

The formulations may also comprise a pharmaceutically acceptable sweetener. In some embodiments, the sweetener comprises at least one intense sweetener such as, but not limited to, saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, or from about 0.06% in the low-dosage formulations and about 0.08% in the high-dosage ones. The bulk sweetener can effectively be used in larger quantities ranging from about 10% to about 35% or from about 10% to 15% (w/v).

The formulations may be prepared by conventional techniques, for example, as described in Remington's Pharmaceutical Sciences, 1985 or in Remington: The Science and Practice of Pharmacy, 19th edition, 1995, where such conventional techniques of the pharmaceutical industry involve dissolving and mixing the ingredients as appropriate to give the desired end product.

Administration of the compound or the formulations described herein may be carried out using any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, inhalation, or by oral administration. In some embodiments, the compound or formulation is administered intravenously or by injection.

For oral administration, the crystalline Form I or a therapeutically acceptable salt thereof can be formulated in unit dosage forms such as gel caps, caplets, granules, lozenges, bulk powders, capsules or tablets. The tablets or capsules may be prepared by conventional means with pharmaceutically acceptable excipients, including binding agents, for example, pregelatinized maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate: or wetting agents, for example, sodium lauryl sulphate. Tablets can be coated by methods well known in the art.

Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For topical administration, the crystalline Form I can be formulated in a pharmaceutically acceptable vehicle containing 0.1 to 10 percent, preferably 0.5 to 5 percent, of the active compound(s). Such formulations can be in the form of a cream, lotion, sublingual tablet, aerosols and/or emulsions and can be included in a transdermal or buccal patch of the matrix or reservoir type as are conventional in the art for this purpose.

For parenteral administration, the crystalline Form I or an amorphous form of the compound can be administered by either intravenous, subcutaneous, or intramuscular injection, in compositions with pharmaceutically acceptable vehicles or carriers. Form I can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Additionally, the compound can be precipitated and stored in an ampule or other container and then dissolved in a solution prior to being administered to a subject.

For administration by injection, the compound can be used in solution, and, for example, in a sterile aqueous vehicle which may also contain other solutes such as buffers or preservatives as well as sufficient quantities of pharmaceutically acceptable salts or of glucose to make the solution isotonic. In some embodiments, the pharmaceutical compositions may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's pharmaceutical Sciences" by E. W. Martin.

For administration by inhalation, the compound may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. For intranasal administration, the compound may be used, for example, as a liquid spray, as a powder or in the form of drops.

The compound can also be formulated in rectal compositions, for example, suppositories or retention enemas, for example, containing conventional suppository bases, for example, cocoa butter or other glycerides.

Furthermore, the compound can be formulated as a depot preparation. Such long-acting formulations can be administered by implantation (for example, subcutaneously or intramuscularly) or by intramuscular injection. Thus, for example, the compound can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack can also contain individual vials or other containers. The pack or dispenser device can be accompanied by instructions for administration.

Dosages

The crystalline Form I may be administered to a patient at therapeutically effective doses to prevent, treat, or control diseases and disorders mediated, in whole or in part, by a GPCR-ligand interaction described herein. Pharmaceutical compositions comprising the crystalline Form I may be administered to a patient in an amount sufficient to elicit an effective protective or therapeutic response in the patient. The dose will be determined by the efficacy of the particular compound employed and the condition of the subject, as well as the body weight or surface area of the area to be treated. The size of the dose also will be determined by the existence, nature, and extent of any adverse effects that accompany the administration of a particular compound or vector in a particular subject.

The amount and frequency of administration of the compound comprising the crystalline Form I or another amorphous form prepared according to a method described herein and/or the pharmaceutically acceptable salts thereof can be regulated according to the judgment of the attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general, it is contemplated that an effective amount would be from 0.001 mg/kg to 10 mg/kg body weight, and in particular from 0.01 mg/kg to 1 mg/kg body weight. More specifically, it is contemplated that an effective amount would be to continuously infuse by intravenous administration from 0.01 micrograms/kg body weight/min to 100 micrograms/kg body weight/min for a period of 12 hours to 14 days. It may be appropriate to administer the required dose as two, three, four or more sub-doses at appropriate intervals throughout the day. Sub-doses may be formulated as unit dosage forms, for example, containing 0.01 to 500 mg, and in particular 0.1 mg to 200 mg of active ingredient per unit dosage form.

In some embodiments, the pharmaceutical preparation is in a unit dosage form. In such form, the preparation is subdivided into suitably sized unit doses containing appropriate quantities of the active component, e.g., an effective amount to achieve the desired purpose. The quantity of active compound in a unit dose of preparation may be varied or adjusted from about 0.01 mg to about 1000 mg, from about 0.01 mg to about 750 mg, from about 0.01 mg to about 500 mg, or from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

Medical Use

A composition comprising a crystalline form of the compound of Formula I or an amorphous form prepared according to a method described herein can be used for treating or preventing pain, neuropathic pain, migraine, headache, depression, Parkinson's disease, anxiety, overactive bladder, medication overuse headache, hyperalgesia, decreasing nociceptive sensitization, pain in an opioid exposed subject, PTSD, or related disorders and conditions or any combination thereof.

A composition comprising the crystalline Form I of the compound of Formula I can be used for treating or preventing pain, neuropathic pain, migraine, headache, depression, Parkinson's disease, anxiety, overactive bladder, medication overuse headache, hyperalgesia, decreasing nociceptive sensitization, pain in an opioid exposed subject, PTSD, or related disorders and conditions or any combination thereof.

A composition comprising the crystalline Form I of the compound of Formula I can be used for treating or preventing hyperalgesia. In some embodiments, the hyperalgesia is opioid induced hyperalgesia. In some embodiments, the opioid induced hyperalgesia is morphine, oxycodone, hydrocodone, hydromorphone, fentanyl, meperidine, alfentanil, remifentanil, sufentanil, etorphine, buprenorphine, methadone, and/or heroin induced hyperalgesia. In some embodiments, the subject has been administered an opioid prior to being administered the crystalline Form I of the compound of Formula I or a pharmaceutical composition thereof.

A composition comprising the crystalline Form I of the compound of Formula I can be used for treating pain in a subject comprising: administering an opioid agonist to the subject until the opioid increases nociceptive sensitization in the subject; and administering to a patient in need thereof, the crystalline Form I of the compound of Formula I or a pharmaceutical composition thereof.

A composition comprising the crystalline Form I of the compound of Formula I can be used for treating pain in an opioid exposed subject comprising: a) administering an opioid agonist to the subject; b) administering to the subject of step a), in the absence of the opioid administered in step a), a crystalline Form I of the compound of Formula I or a pharmaceutical composition thereof. In some embodiments, In some embodiments, the opioid agonist is morphine, oxycodone, hydrocodone, hydromorphone, fentanyl, meperidine, alfentanil, remifentanil, sufentanil, etorphine, buprenorphine, methadone, and/or heroin, or a pharmaceutically acceptable salt thereof A composition comprising the crystalline Form I of the compound of Formula I can be used for decreasing nociceptive sensitization in a subject. In some embodiments, the subject has opioid induced nociceptive sensitization.

A composition comprising the crystalline Form I of the compound of Formula I can be used for treating medication overuse headache in a subject comprising administering to a patient in need thereof, a crystalline form of the compound of Formula I or a pharmaceutical composition thereof. In some embodiments, the medication overuse headache is caused by acetaminophen, aspirin, a mu-opioid agonist, a non-steroidal anti-inflammatory drug (NSAID), or a triptan. In some embodiments, the triptan is sumatriptan, rizatriptan, naratriptan, zolmitriptan, eletriptan, almotriptan, frovatriptan, avitriptan, or donitriptan, or a pharmaceutically acceptable salt thereof. In some embodiments, the mu-opioid agonist is morphine, oxycodone, hydrocodone, hydromorphone, fentanyl, meperidine, alfentanil, remifentanil, sufentanil, etorphine, buprenorphine, methadone, or heroin, or a pharmaceutically acceptable salt thereof.

A composition comprising the crystalline Form I of the compound of Formula I can be used for treating a migraine in a subject, the method comprising: administering a triptan to a subject; and administering to a patient in need thereof, a crystalline form of the compound of Formula I or a pharmaceutical composition thereof. In some embodiments, the crystalline form of the compound of Formula I or a pharmaceutical composition thereof is administered in the absence of the triptan. In some embodiments, the triptan is sumatriptan, rizatriptan, naratriptan, zolmitriptan, eletriptan, almotriptan, frovatriptan, avitriptan, or donitriptan, or a pharmaceutically acceptable salt thereof. In some embodiments, the subject develops mediation overuse headache prior to being administered the crystalline form of the compound of Formula I or a pharmaceutical composition thereof.

Combination Therapies

Methods are also provided for treating or preventing pain, neuropathic pain, migraine, headache, depression, Parkinson's disease, anxiety, overactive bladder, medication overuse headache, hyperalgesia, decreasing nociceptive sensitization, pain in an opioid exposed subject, PTSD, or related disorders and conditions or any combination thereof by administering crystalline Form I and/or an amorphous form prepared according to a method described herein, and/or pharmaceutically acceptable salts thereof, in combination with other drugs for the treatment of pain, neuropathic pain, migraine, headache, depression, Parkinson's disease, anxiety, overactive bladder, medication overuse headache, hyperalgesia, decreasing nociceptive sensitization, pain in an opioid exposed subject, PTSD, or related disorders and conditions or any combination thereof.

In the combination therapies, crystalline Form I or the amorphous form is co-administered with one or more drugs for the treatment of pain, neuropathic pain, migraine, headache, depression, Parkinson's disease, anxiety, overactive bladder, medication overuse headache, hyperalgesia, decreasing nociceptive sensitization, pain in an opioid exposed subject, PTSD, or related disorders and conditions or any combination thereof to increase efficacy and to reduce side effects associated with high doses of these therapeutics.

The combination therapies described above have synergistic and additive therapeutic effects. An improvement in the drug therapeutic regimen can be described as the interaction of two or more agents so that their combined effect reduces the incidence of adverse event (AE) of either or both agents used in co-therapy. This reduction in the incidence of adverse effects can be a result of, e.g., administration of lower dosages of either or both agent used in the co-therapy. For example, if the effect of Drug A alone is 25% and has an adverse event incidence of 45% at labeled dose; and the effect of Drug B alone is 25% and has an adverse event incidence of 30% at labeled dose, but when the two drugs are combined at lower than labeled doses of each, if the overall effect is 35% (an improvement, but not synergistic or additive) and the adverse incidence rate is 20%, there is an improvement in the drug therapeutic regimen.

In some embodiments, the compounds described herein are administered as a mono-therapy. In some embodiments, the compounds described herein are administered as part of a combination therapy. For example, a compound may be used in combination with other drugs or therapies that are used in the treatment/prevention/suppression and/or amelioration of the diseases or conditions for which compounds are useful.

Such other drug(s) may be administered, by a route and in an amount commonly used therefore, contemporaneously or sequentially with the compounds described herein. When a compound described herein is used contemporaneously with one or more other drugs, a pharmaceutical unit dosage form containing such other drugs in addition to the compound described herein may be employed. Accordingly, the pharmaceutical compositions include those that also contain one or more other active ingredients, in addition to the compounds described herein.

A subject or patient in whom administration of the therapeutic compound is an effective therapeutic regimen for a disease or disorder is often a human, but can be any animal, including a laboratory animal in the context of a clinical trial or screening or activity experiment. Thus, as can be readily appreciated by one of ordinary skill in the art, the methods, compound and compositions are particularly suited to administration to any animal, such as a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The following examples are merely illustrative and should not be construed as limiting the scope of the embodiments in any way as many variations and equivalents that are encompassed by these embodiments will become apparent to those skilled in the art upon reading the present disclosure.

In order that the embodiments disclosed herein may be more efficiently understood, examples are provided below. It should be understood that these examples are for illustrative purposes only and are not to be construed as limiting the embodiments in any manner.

In some embodiments, the following non-limiting embodiments are provided:

1. A crystalline form of (−)-6-{[(trans, trans)-4-[3-(2-methoxyethoxy)phenyl]-2-methyl-1-[2-(1H-pyrrol-1-yl)ethyl]piperidin-3-yl]methoxy}-2,3-dihydro-1H-isoindol-1-one having a formula of Formula I

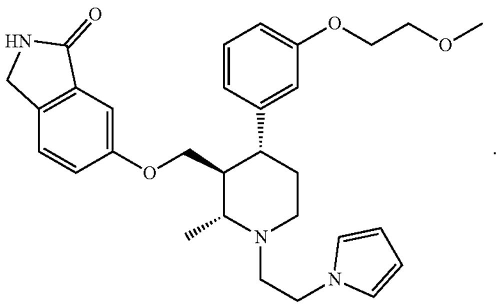

2. A crystalline Form I of (−)-6-{[(trans, trans)-4-[3-(2-methoxyethoxy)phenyl]-2-methyl-1-[2-(1H-pyrrol-1-yl)ethyl]piperidin-3-yl]methoxy}-2,3-dihydro-1H-isoindol-1-one having a formula of Formula I

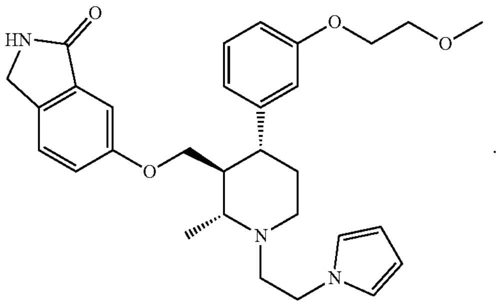

3. The crystalline Form I of embodiment 2 characterized by an X-ray powder diffraction pattern comprising a peak at about 18.3±0.5 degrees 2θ.

4. The crystalline Form I of embodiment 2 characterized by an X-ray powder diffraction pattern comprising a peak at about 17.1±0.5 degrees 2θ.

5. The crystalline Form I of embodiment 2 characterized by an X-ray powder diffraction pattern comprising a peak at about 17.3±0.5 degrees 2θ.

6. The crystalline Form I of embodiment 2 characterized by an X-ray powder diffraction pattern comprising a peak at about 21.2±0.5 degrees 2θ.

7. The crystalline Form I of embodiment 2 characterized by an X-ray powder diffraction pattern comprising a peak at about 14.0±0.5 degrees 2θ.

8. The crystalline Form I of embodiment 2 characterized by an X-ray powder diffraction pattern comprising peaks at about 18.3 and at about 17.1±0.5 degrees 2θ.

9. The crystalline Form I of embodiment 2 characterized by an X-ray powder diffraction pattern comprising peaks at about 17.1 and at about 17.3±0.5 degrees 2θ.

10. The crystalline Form I of embodiment 2 characterized by an X-ray powder diffraction pattern comprising peaks at about 17.3 and at about 21.2±0.5 degrees 2θ.

11. The crystalline Form I of embodiment 2 characterized by an X-ray powder diffraction pattern comprising peaks at about 21.2 and at about 17.1±0.5 degrees 2θ.

12. The crystalline Form I of embodiment 2 characterized by an X-ray powder diffraction pattern comprising peaks at about 21.2 and at about 14.0±0.5 degrees 2θ.

13. The crystalline Form I of embodiment 2 characterized by an X-ray powder diffraction pattern comprising peaks at about 21.2, at about 17.1, and at about 14.0±0.5 degrees 2θ.

14. The crystalline Form I of embodiment 2 characterized by an X-ray powder diffraction pattern comprising peaks at about 17.3, at about 18.3, and at about 21.2±0.5 degrees 2θ.

15. The crystalline Form I of embodiment 2 characterized by an X-ray powder diffraction pattern comprising one or more peaks at about 18.3, at about 17.1, at about 17.3, at about 21.2, and at about 14.0±0.5 degrees 2θ.

16. The crystalline Form I of embodiment 2 characterized by an X-ray powder diffraction pattern comprising one or more peaks as shown in FIG. 16.

17. The crystalline Form I of embodiment 2 characterized by an X-ray powder diffraction pattern comprising one or more d-spacing values at about 6.3, at about 5.1, at about 5.2, at about 4.9, and at about 4.2±0.5 degrees angstroms.

18. A pharmaceutical composition comprising a crystalline form of any one of embodiments 1-17.

19. A pharmaceutical composition comprising the crystalline Form I of embodiment 2.

20. The pharmaceutical composition of embodiment 19, wherein the crystalline Form I is a compound of Formula I.

21. The pharmaceutical composition of embodiment 19, further comprising an additional drug for the treatment of pain, migraine, headache, depression, Parkinson's disease, anxiety, overactive bladder, medication overuse headache, hyperalgesia, decreasing nociceptive sensitization, pain in an opioid exposed subject, PTSD other disorders and conditions described herein or any combination thereof 22. A process for preparing a crystalline form of the compound of Formula I, comprising crystallizing the crystalline form of the compound of Formula I and optionally isolating the crystalline form of the compound of Formula I.

23. The process of embodiment 22, wherein the crystallizing step comprises dissolving the compound of Formula I in an organic solvent to form a solution.

24. The process of embodiment 23, wherein the organic solvent is selected from tetrahydrofuran, tert-butylmethyl ether, methyl ethyl ketone, heptane, 2-methyl tetrahydrofuran, toluene, anisole, DMSO, water, ethanol, butanol, methanol, dicholoromethane, ethyl acetate, acetone, ethyl acetate, dimethylformamide, acetonitrile, dimethyl sulfoxide, propylene carbonate, formic acid, isopropanol, propanol, acetic acid, nitromethane, and a combination thereof.

25. The process of embodiment 23, wherein the organic solvent is tert-butylmethyl ether, methyl ethyl ketone, or tetrahydrofuran, or a combination thereof.

26. The process of embodiment 23, wherein the organic solvent is tert-butylmethyl ether.

27. The process of embodiment 23, wherein the organic solvent is methyl ethyl ketone.

28. The process of embodiment 23, wherein the organic solvent is tetrahydrofuran.

29. The process of any one of embodiments 23-28, further comprising heating the solution of the compound of Formula I in the organic solvent.

30. The process of embodiment 29, wherein the solution is heated to a temperature of about 40° C.

31. The process of embodiment 30, wherein the solution was stirred at about 40° C. for about 1 h.

32. The process of any one of embodiments 29-31, further comprising cooling the heated solution to a temperature of about 20° C.

33. The process of embodiment 32, wherein the heated solution is cooled at a rate of about 1° C./min.

34. The process according to embodiments 32 or 33, further comprising adding one or more anti-solvents to the cooled solution to form a mixture.

35. The process according to embodiments 32 or 33, further comprising adding one anti-solvent to the cooled solution to form a mixture.

36. The process according to embodiments 34 or 35, wherein the anti-solvent is heptane, t-butylmethyl ether, or water, or a combination thereof.

37. The process according to embodiments 34 or 35, wherein the anti-solvent is heptane.

38. The process according to embodiments 34 or 35, wherein the anti-solvent is t-butylmethyl ether.

49. The process according to embodiments 34 or 35, wherein the anti-solvent is water.

40. The process according to embodiments 34 or 35, wherein the anti-solvent is a combination of heptane and t-butylmethyl ether.

41. The process of any one of embodiments 34-40, further comprising heating the mixture to about 40° C.

42. The process of embodiment 41, wherein the mixture is heated at a rate of about 1° C./min.

43. The process according to embodiments 41 or 42, further comprising temperature cycling of the mixture between 40° C. and 5° C.

44. The process of embodiment 43, wherein the temperature cycling comprises holding the mixture at about 40° C. for about 1 h and holding the mixture at about 5° C. for about 1 h during each cycle.

45. The process according to embodiments 43 or 44, wherein the temperature cycling is maintained for about 17 h.

46. The process of any one of embodiments 43-45, further comprising settling the mixture at about 5° C.

47. The process of any one of embodiments 22-46, wherein the isolating step comprises centrifuging the crystallized compound of Formula I to isolate the crystalline form.

48. The process of any one of embodiments 22-47, further comprising drying the crystalline form of the compound of Formula I.

49. The process of embodiment 48, wherein the drying is under vacuum.

50. A pharmaceutical composition comprising the compound of Formula I prepared by precipitating the compound of Formula I.

51. The pharmaceutical composition of embodiment 50, wherein the compound of Formula I is precipitated from an organic solvent.

52. The pharmaceutical composition of embodiment 51, wherein the organic solvent is selected from tetrahydrofuran, tert-butylmethyl ether, methyl ethyl ketone, heptane, 2-methyl tetrahydrofuran, toluene, anisole, DMSO, water, ethanol, butanol, methanol, dicholoromethane, ethyl acetate, acetone, ethyl acetate, dimethylformamide, acetonitrile, dimethyl sulfoxide, propylene carbonate, formic acid, isopropanol, propanol, acetic acid, nitromethane, and a combination thereof.

53. A method of treating or preventing pain, neuropathic pain, migraine, headache, depression, Parkinson's disease, anxiety, overactive bladder, medication overuse headache, hyperalgesia, decreasing nociceptive sensitization, pain in an opioid exposed subject, PTSD, or related disorders and conditions or any combination thereof comprising administering to a patient in need thereof comprising administering to a patient in need thereof, a crystalline form prepared according the any one of embodiment 22-49, or a pharmaceutical composition of any one of embodiments 50-52.

54. A method of treating or preventing pain, neuropathic pain, migraine, headache, depression, Parkinson's disease, anxiety, overactive bladder, medication overuse headache, hyperalgesia, decreasing nociceptive sensitization, pain in an opioid exposed subject, PTSD, or related disorders and conditions or any combination thereof comprising administering to a patient in need thereof, the crystalline Form I of embodiment 2 or a pharmaceutical composition of any one of embodiments 19-21.

55. A method of treating hyperalgesia in a subject comprising administering to the subject comprising administering to a patient in need thereof, the crystalline Form I of embodiment 2 or a pharmaceutical composition of any one of embodiments 19-21.

56. The method of embodiment 55, wherein the hyperalgesia is opioid induced hyperalgesia.

57. The method of embodiment 56, wherein the opioid induced hyperalgesia is morphine, oxycodone, hydrocodone, hydromorphone, fentanyl, meperidine, alfentanil, remifentanil, sufentanil, etorphine, buprenorphine, methadone, and/or heroin induced hyperalgesia.

58. The method of embodiment 57, wherein the subject has been administered an opioid prior to being administered the crystalline Form I of embodiment 2 or a pharmaceutical composition thereof.

59. A method of decreasing nociceptive sensitization in a subject comprising administering to a patient in need thereof, the crystalline Form I of embodiment 2 or a pharmaceutical composition of any one of embodiments 19-21.

60. The method of embodiment 59, wherein the subject has opioid induced nociceptive sensitization.

61. A method of treating pain in a subject comprising administering an opioid agonist to the subject until the opioid increases nociceptive sensitization in the subject and administering to a patient in need thereof, the crystalline Form I of embodiment 2 or a pharmaceutical composition of any one of embodiments 19-21.

62. The method of embodiment 61, wherein the opioid agonist is morphine, oxycodone, hydrocodone, hydromorphone, fentanyl, meperidine, alfentanil, remifentanil, sufentanil, etorphine, buprenorphine, methadone, and/or heroin, or a pharmaceutically acceptable salt thereof.

63. A method of treating pain in an opioid exposed subject comprising:

a) administering an opioid agonist to the subject;

b) administering to the subject of step a), in the absence of the opioid administered in step a), the crystalline Form I of embodiment 2 or a pharmaceutical composition of any one of embodiments 19-21.

64. The method of embodiment 63, wherein the opioid is morphine, oxycodone, hydrocodone, hydromorphone, fentanyl, meperidine, alfentanil, remifentanil, sufentanil, etorphine, buprenorphine, methadone, and/or heroin, or a pharmaceutically acceptable salt thereof.

65. A method of treating medication overuse headache in a subject comprising administering to a patient in need thereof, the crystalline Form I of embodiment 2, or a pharmaceutical composition of any one of embodiments 19-21.

66. The method of embodiment 65, wherein the medication overuse headache is caused by acetaminophen, aspirin, a mu-opioid agonist, a non-steroidal anti-inflammatory drug (NSAID), or a triptan.

67. The method of embodiment 66, wherein the triptan is sumatriptan, rizatriptan, naratriptan, zolmitriptan, eletriptan, almotriptan, frovatriptan, avitriptan, or donitriptan, or a pharmaceutically acceptable salt thereof.

68. The method of embodiment 67, wherein the mu-opioid agonist is morphine, oxycodone, hydrocodone, hydromorphone, fentanyl, meperidine, alfentanil, remifentanil, sufentanil, etorphine, buprenorphine, methadone, or heroin, or a pharmaceutically acceptable salt thereof.

69. A method of treating a migraine in a subject, the method comprising:

a) administering a triptan to a subject; and b) administering to a patient in need thereof, the crystalline Form I of embodiment 2, or a pharmaceutical composition of any one of embodiments 19-21.

70. The method of embodiment 69, wherein the crystalline Form I or a pharmaceutical composition thereof is administered in the absence of the triptan.

71. The method of embodiment 69, wherein the triptan is sumatriptan, rizatriptan, naratriptan, zolmitriptan, eletriptan, almotriptan, frovatriptan, avitriptan, or donitriptan, or a pharmaceutically acceptable salt thereof.

72. The method of embodiment 69, wherein the subject develops mediation overuse headache prior to being administered the crystalline Form I or the pharmaceutical composition.

EXAMPLES

Example 1

Preparation of the Compound of Formula I in Free Base Form

The compound of Formula I in free base form was prepared with a salt break procedure where saturated potassium carbonate used to remove the HCl and the free base extracted into dichloromethane. The compound of Formula I in free base form was successfully prepared from the input (HCl salt of a compound of Formula I) on a 0.5 g scale, using saturated potassium carbonate solution and extraction into dichloromethane. XRPD analysis of the isolated solids indicated that the material was amorphous with purity of ca. 98.5% area obtained by HPLC, consistent with the input material. HPLC-CAD analysis was consistent with free base formation, with no chloride detected. $^{1}H$ NMR spectroscopy showed a shift in resonances δ 1.5 ppm and a loss of the peaks at δ 1.1 ppm as shown in FIG. 6. after a HCl salt had been formed. An isolated yield of ca. 90% was obtained and the material contained 1.4% wt. dichloromethane. The $^{13}C$ NMR spectrum was consistent with the structure of the compound of Formula I free base and FT-IR analysis showed a νC═O stretch at 1689 $cm^{-1}$. PLM analysis indicated that the material was slightly birefringent, with poorly defined, glassy morphology. TG analysis showed weight loss of 1.2% up to 280° C., while DSC analysis showed a broad, endothermic event with onset ca. 30° C. (peak at 41° C.), followed by a second broad, endothermic event with onset ca. 44° C. (peak at 61° C.) during the first heat. A glass transition with a mid-point half-height of ca. 35° C. was observed during the first cool. The second heat showed an endothermic event with onset ca. 35° C. (peak at 41° C.), while the second cool showed a glass transition with a mid-point half-height of ca. 34° C. The results of XRPD, PLM, TG, DSC, FT-IR, NMR, and HPLC analysis are shown in FIGS. 1-8.

Preparation of the free base was successfully scaled-up to 7 g, with an isolated yield of 92%. The resulted compound of Formula I in free base form had the characterization data consistent with that prepared in the 0.5 g scale as described herein.

Example 2

Approximate Solubility Studies of the Amorphous Form of the Compound of Formula I The approximate solubility values of the amorphous free base in the selected solvent systems (see Table 1) was estimated by the solvent addition technique. The following procedure was used for the study:

Approximately 10 mg of material was weighed out into 18×2 mL push-cap vials.

Each solvent/solvent mixture was added to the appropriate vial in 5 volume aliquots (50 μL) until either 1 mL of solvent had been added or until the material dissolved.

In between additions, the sample was stirred at 40° C.

If 1000 μL of solvent was added without dissolution of the material, solubility was calculated to be below this point.

Once addition was complete, all experiments were temperature cycled between 40° C. and 5° C. (1 h hold; 0.1° C./min ramp/cool) for ca. 21 h.

Residual solids were isolated by centrifugation (0.22 μm nylon filter) or by decanting the mother liquor and analyzed by XRPD.

Anti-solvent addition (ASA) at 20° C. was carried out on solutions, followed by further temperature cycling for 21 h.

Any solids were then isolated by centrifugation (0.22 μm nylon filter) or by decanting the mother liquor and analyzed by XRPD.

Experiments which remained solutions had further AS added at 20° C. and were temperature cycled for a further 21 h.

Residual solids were isolated by centrifugation (0.22 μm nylon filter) or by decanting the mother liquor and analyzed by XRPD.

Selected isolated material was dried under vacuum at ambient temperature (ca. 20° C.) for ca. 19-21 h then re-analyzed by XRPD.

Selected dried solids were analyzed by PLM, TG/DSC, DSC, $^{1}H$ NMR spectroscopy and HPLC.

Further details can be found in Table 1.

TABLE 1

Solvent systems used for approximate solubility and initial crystallization trials of free base

| | Initial Solvent System | | Additional Solvents | | | Final S:AS |
|---|---|---|---|---|---|---|
| | Solvent System (v/v) | Vol./μL | Anti-Solvent | ASA (1) Vol./μL | ASA (2) Vol./μL | Ratio/ v/v/v % |
| | Acetone | 50 | Heptane | 80 | | 38:62 |
| 2 | Acetonitrile | 50 | tBME | 400 | 400, 3000* | 1:21:78 |
| 3 | Anisole | 50 | Heptane | 500 | | 9:91 |
| 4 | t-Butylmethyl ether (tBME) | 1000 | | 1000 | | 50:50 |
| 5 | Dichloromethane | 50 | | 200 | | 20:80 |
| 6 | Dimethylsulfoxide (DMSO) | 50 | tBME | 200 | | 20:80 |
| 7 | Ethanol | 50 | Heptane | 200 | 800 | 5:95 |
| 8 | Ethyl acetate | 50 | | 180 | | 22:78 |
| 9 | Heptane | 1000 | | | | |
| 10 | Methanol | 50 | tBME | 1900 | 9000* | 0.5:17.5:82 |
| 11 | Methyl ethyl ketone (MEK) | 50 | Heptane | 200 | | 20:80 |
| 12 | 2-Methyl THF | 50 | | 80 | | 38:62 |
| 13 | 2-Propanol | 50 | | 200 | | 20:80 |
| 14 | Tetrahydrofuran (THF) | 50 | | 180 | | 22:78 |
| 15 | Toluene | 50 | | 80 | | 38:62 |
| 16 | Water | 1000 | | | | |
| 17 | Ethanol:Water 75:25 | 50 | Water | 60 | | 34:66 |
| 18 | Methanol:Water 77:23 | 200 | | 120 | | 48:52 |

*Heptane used as second anti-solvent during ASA 2.

ASA: Anti-solvent addition

The approximate solubility values of the amorphous free base in a range of different solvent systems was determined at ambient temperature, with heating to 40° C. between solvent aliquots. The solutions and slurries obtained were then used in initial small-scale crystallization trials (see Table 1 for details). The following observations and results were obtained from these experiments:

The free base had excellent solubility (>200 mg/mL) in almost all solvents investigated, including acetone, acetonitrile, anisole, dichloromethane, dimethylsulfoxide, ethanol, ethyl acetate, methanol, methyl ethyl ketone, 2-methyl THF, 2-propanol, THF and toluene.

Excellent solubility was also obtained in ethanol:water 75:25 v/v.

The free base had moderate solubility (50 mg/mL) in methanol:water 77:23 v/v.

The free base had poor solubility (≤10 mg/mL) in water, tBME and heptane.

A slurry (with material on the wall of the vial) was obtained after temperature cycling the residual solids from the experiment in heptane. The material formed gel in water.

Oiling was observed after ASA to experiments carried out in acetone, acetonitrile, DMSO, ethanol, MEK and 2-propanol.

Gum formed after ASA to experiments carried out in anisole, dichloromethane, ethyl acetate, 2-Me THF, toluene, ethanol:water 75:25 v/v and methanol:water 77:23 v/v.

After further temperature cycling, solids were obtained from experiments carried out using tBME, MEK and THF as the initial solvent system. The remaining experiments formed oil, gel or remained clear solutions.

After further ASA and temperature cycling, solids were obtained from experiments carried out using acetonitrile, ethanol and methanol as the initial solvent system.

XRPD analysis of the material isolated after ASA and further temperature cycling indicated that crystalline material was isolated from acetonitrile:tBME:heptane 1:21:78 v/v %, anisole:heptane 38:62 v/v %, tBME:heptane 50:50 v/v %, ethanol:heptane 5:95 v/v %, methanol:tBME:heptane 0.5:17.5:82 v/v %, MEK:heptane 20:80 v/v % and THF:heptane 22:78 v/v %. All diffractograms had the same pattern, which was designated the crystalline Form I.

The crystalline solids remained crystalline, with no change in diffraction pattern, after drying under vacuum.

XRPD analysis of the material isolated after ASA and further temperature cycling indicated that poorly crystalline material (consistent with the crystalline Form I) was isolated from 2-propanol:heptane 20:80 v/v %.

XRPD analysis of the material isolated after ASA and further temperature cycling indicated that amorphous material was isolated from dichloromethane:heptane 20:80 v/v %, ethyl acetate:heptane 22:78 v/v %, 2-Me THF:heptane 38:62 v/v %, toluene:heptane 38:62 v/v %, ethanol:water 34:66 v/v % and methanol:water 48:52 v/v %.

Amorphous material was also isolated after temperature cycling in heptane.

The crystalline solids isolated from experiment 4 (final solvent system of tBME:heptane 50:50 v/v %) had a chemical purity of 99.0% area (cf. input material purity of 98.5% area).

The crystalline solids isolated from experiment 11 (final solvent system of MEK:heptane 20:80 v/v %) had a chemical purity of 99.1% area (cf. input material purity of 98.5% area).

PLM analysis of the crystalline solids isolated from experiments 4 and 11 indicated that the solids were non-birefringent and agglomerated, with no clear morphology.

TG/DSC analysis of the material isolated from tBME: heptane 50:50 v/v % showed no weight loss prior to decomposition. One endothermic event was observed, with an onset temperature of ca. 95° C. and a peak temperature of 109° C.

with onset ca. 38° C. (peak at 42° C.), while the second cool showed a glass transition with a mid-point half-height of ca. 33° C.

$^1$H NMR spectroscopy of the material isolated from tBME:heptane 50:50 v/v % was consistent with the structure of the compound of Formula I free base. The residual tBME could not be quantified, due to overlapping signals with the API. Residual heptane was observed, equal to 0.46% w/w, or 0.02 equivalents.

See Table 2 for further details.

The results of XRPD, PLM, TG, DSC, FT-JR, NMR, and HPLC analysis are shown in FIGS. 9-15.

TABLE 2

Results of approximate solubility and initial crystallization trials of free base

| | Initial Solvent System (v/v) | Approximate Solubility/ mg/mL | Anti-Solvent | Observations: After Temp. Cycling | Observations: After ASA | Observations: After Further ASA and T/C | XRPD Wet | XRPD Dry |
|---|---|---|---|---|---|---|---|---|
| 1 | Acetone | >200 | Heptane | Clear solution | Oil | | NS | |
| 2 | Acetonitrile | >200 | tBME, Heptane | Clear solution | Clear solution | Solids [a] | CRY | CRY |
| 3 | Anisole | >200 | Heptane | Clear solution | Gum | | CRY | CRY |
| 4 | tBME | 10 | | Clear solution | Slurry | | CRY | CRY |
| 5 | Dichloromethane | >200 | | Clear solution | Gel | | AM | |
| 6 | DMSO | >200 | tBME | Clear solution | Oil | | NS | |
| 7 | Ethanol | >200 | Heptane | Clear solution | Clear solution | Slurry | CRY | CRY |
| 8 | Ethyl acetate | >200 | | Clear solution | Gel | | AM | |
| 9 | Heptane | <10 | | Solids [a] | | | AM | |
| 10 | Methanol | >200 | tBME, Heptane | Clear solution | Clear solution | Solids [a] | CRY | CRY |
| 11 | MEK | >200 | Heptane | Clear solution | Solids [a] | | CRY | CRY |
| 12 | 2-Methyl THF | >200 | | Clear solution | Gel | | AM* | |
| 13 | 2-Propanol | >200 | | Clear solution | Gel | | PAM | |
| 14 | THF | >200 | | Clear solution | Solids [a] | | CRY | CRY |
| 15 | Toluene | >200 | | Clear solution | Gel | | AM | |
| 16 | Water | <10 | | Gel | | | NS | |
| 17 | Ethanol:Water 75:25 | >200 | Water | Clear solution | Gel | | AM | |
| 18 | Methanol:Water 77:23 | 50 | | Clear solution | Gel | | AM | |

AM: Amorphous;
PAM: Poorly crystalline;
CRY: Crystalline;
NS: No solids:
[a] Solids on vial walls;
*Predominantly DSC analysis of material isolated from MEK:heptane 20:80 v/v % was carried out between −10° C. and 250° C. and showed an endothermic event with onset ca. 93° C. (peak at 97° C.) during the first heat. A glass transition with a mid-point half-height of ca. 32° C. was observed during the first cool. The second heat showed a glass transition with a mid-point half-height of ca. 38° C., with an endothermic recovery event also observed Approximate solubility studies were carried out using the amorphous free base in a range of different solvent systems at 20° C., heating to 40° C. between additions of solvent aliquots. The free base had excellent solubility (>200 mg/mL) in almost all solvents investigated, including acetone, acetonitrile, anisole, dichloromethane, dimethylsulfoxide, ethanol, ethyl acetate, methanol, methyl ethyl ketone, 2-methyl THF, 2-propanol, THF and toluene. Excellent solubility was also obtained in ethanol:water 75:25 v/v, with moderate solubility of ca. 50 mg/mL obtained in methanol:water 77:23 v/v. Poor solubility (≤10 mg/mL) was obtained in water, tBME and heptane, giving limited options for antisolvents. Once the solubility screen was complete, the residual slurries and solutions were temperature cycled, with anti-solvent addition then carried out where experiments remained solutions. XRPD analysis indicated that crystalline material was isolated from several experiments (7 out of 18) after ASA and temperature cycling, from acetonitrile:tBME:heptane 1:21:78 v/v %, anisole:heptane 38:62 v/v %, tBME:heptane 50:50 v/v %, ethanol:heptane 5:95 v/v %, methanol:tBME:heptane 0.5:17.5:82 v/v %, MEK:heptane 20:80 v/v % and THF:heptane 22:78 v/v %. Poorly crystalline material was isolated from 2-propanol:heptane 20:80 v/v %. Amorphous, or predominantly amorphous material was recovered from 7 experiments, using heptane, dichloromethane:heptane 20:80 v/v %, ethyl acetate:heptane 22:78 v/v %, 2-Me THF:heptane 38:62 v/v %, toluene: heptane 38:62 v/v %, ethanol:water 34:66 v/v % and methanol:water 48:52 v/v %. The remaining experiments yielded gel or oil.

All of the crystalline diffractograms had the same pattern, designated the crystalline Form I and further analysis was carried out on material isolated from tBME:heptane 50:50 v/v % and MEK:heptane 20:80 v/v %. TG/DSC analysis indicated that the crystalline Form I was an anhydrous form with no weight loss observed prior to decomposition and a single endothermic event at onset 95° C. (peak at 109° C.). DSC analysis carried out between −10° C. and 250° C. showed an endothermic event with onset ca. 93° C. (peak at 97° C.) during the first heat, while the second heat showed a glass transition with a mid-point half-height of ca. 38° C. and an endothermic recovery event with onset ca. 38° C. (peak at 42° C.). The cooling cycles showed glass transitions with mid-point half-heights of ca. 32-33° C. $^{1}$H NMR spectroscopy of the material isolated from tBME:heptane 50:50 v/v % was consistent with the structure of the compound of Formula I free base, while PLM analysis indicated that the solids were non-birefringent and agglomerated, with no clear morphology. HPLC analysis indicated that the crystalline solids isolated from tBME:heptane 50:50 v/v % had purity of 99.0% area, while the material isolated from MEK:heptane 20:80 v/v % had a purity of 99.1% area, showing some uplift from the input material (98.5% area).

Example 3A

Mini Scale Crystallization of the Compound of Formula I in Free Base Form

Approximately 50 mg of the compound of Formula I in free base form was weighed into 3 vials respectively and a stirrer bar was added to each vial. The appropriate volume of the desired solvent was added to each vial at 20° C. with stirring (see Table 3 for details). The experiments were heated to 40° C. over ca. 10-15 min. The experiments were stirred for 1 h at 40° C. and then cooled to 20° C. at 1° C./min. Anti-solvent addition of heptane was carried out at 20° C. (see Table 3 for details). After the anti-solvent addition was complete, the experiments were heated to 40° C. over ca. 10-15 min. The experiments were temperature cycled between 40° C. and 5° C. for ca. 22 h (1 h hold at 40° C. and 5° C.; 0.1° C./min ramp/cool). After temperature cycling was complete, stirring was halted and solids allowed settling at 5° C. Mother liquors were decanted and solids were isolated by centrifugation (0.22 μm nylon filter) and analyzed by XRPD. Solids were dried under vacuum at 20° C. for ca. 22 h. The dried solids were characterized by XRPD, PLM, TG/DSC, $^{1}$H NMR spectroscopy and HPLC, with further characterization carried out by DSC, DVS and KF where material amounts allowed. FIG. 16 shows the X-ray powder diffraction pattern of Form I of the compound of Formula I.

TABLE 3

| | Initial Solvent System | | | Anti-Solvent | | |
|---|---|---|---|---|---|---|
| | Initial Solvent | Vol./μL | Conc/mg/mL | Anti-Solvent | Vol./μL | Final S:AS Ratio/v/v % |
| 1 | tBME | 5000 | 10 | Heptane | 5000 | 50:50 |
| 2 | MEK | 250 | 200 | | 1000 | 20:80 |
| 3 | THF | 250 | 200 | | 886 | 22:78 |

The following results and observations were obtained from this experiment (see Table 4 for further details):

- After anti-solvent addition to the solutions at 20° C., the experiment carried out using tBME as the initial solvent system had solid adhered to the vial walls. The experiments carried out using MEK and THF as the initial solvent systems were cloudy, with some oil/gum formation noted.
- After temperature cycling overnight, all experiments formed slurries. Material was adhered to the vial walls in experiments carried out in MEK/heptane and THF/heptane.
- XRPD analysis showed that all isolated solids were consistent with the crystalline Form I, which was retained after drying.
- HPLC analysis indicated that the isolated materials had purity of 98.9-99.2% area (cf. input material purity of 98.5% area).
- 30-35 mg of the crystalline Form I was obtained from the scale-up experiments, giving isolated yields of 60-71%.
- PLM analysis of material isolated from tBME:heptane 50:50 v/v % showed that the crystalline Form I was slightly birefringent, with small particles and some rod-like morphology.
- PLM analysis of material isolated from MEK:heptane 20:80 v/v % showed that the crystalline Form I was slightly birefringent, with small particles and some rod-like morphology. Some agglomeration was observed.
- PLM analysis of material isolated from THF:heptane 22:78 v/v % showed that the crystalline Form I was slightly birefringent, with small particles and some rod-like morphology.
- TG/DSC analysis of the material isolated from tBME: heptane 50:50 v/v % showed no weight loss prior to decomposition. One endothermic event was observed, with an onset temperature of ca. 95° C. and a peak temperature of 98° C.
- TG/DSC analysis of the material isolated from MEK: heptane 20:80 v/v % showed no weight loss prior to decomposition. One endothermic event was observed, with an onset temperature of ca. 96° C. and a peak temperature of 100° C.

TG/DSC analysis of the material isolated from THF: heptane 22:78 v/v % showed no weight loss prior to decomposition. One endothermic event was observed, with an onset temperature of ca. 95° C. and a peak temperature of 99° C.

DSC analysis of the crystalline Form I isolated from tBME:heptane 50:50 v/v % carried out between −10-250° C. showed an endothermic event with onset ca. 95° C. (peak at 98° C.) during the first heat. A glass transition with a mid-point half-height of ca. 32° C. was observed during the first cool. The second heat showed a glass transition with a mid-point half-height of ca. 38° C., with an endothermic recovery event also observed with onset ca. 40° C. (peak at 40° C.), while the second cool showed a glass transition with a mid-point half-height of ca. 32° C.

$^1$H NMR spectroscopy of the crystalline Form I isolated from tBME:heptane 50:50 v/v % was consistent with the structure of the compound of Formula I free base. The residual tBME could not be quantified, due to overlapping signals with the API. Residual heptane was observed, equal to 0.91% w/w, or 0.05 equivalents.

$^1$H NMR spectroscopy of the crystalline Form I isolated from MEK:heptane 20:80 v/v % was consistent with the structure of the compound of Formula I free base. The residual MEK could not be quantified, due to overlapping signals with the API. Residual heptane was observed, equal to 0.51% w/w, or 0.02 equivalents.

$^1$H NMR spectroscopy of the crystalline Form I isolated from THF:heptane 22:78 v/v % was consistent with the structure of the compound of Formula I free base. The residual THF could not be quantified, due to overlapping signals with the API. Residual heptane was observed, equal to 0.26% w/w, or 0.01 equivalents.

KF analysis of the crystalline Form I isolated from MEK:heptane 20:80 v/v % indicated a water content of 0.1%.

DVS analysis of material isolated from tBME:heptane 50:50 v/v % showed that the crystalline Form I was slightly hygroscopic, with mass uptake of ca. 0.5% w/w observed at 25° C./80% RH. Post-DVS XRPD analysis indicated that the crystalline Form I was retained.

Appearance testing of the crystalline Form I indicated that it was a white solid (NE12). The results of XRPD, PLM, TG, DSC, FT-IR, DVS, NMR, and HPLC analysis are shown in FIGS. 16-34.

TABLE 4

Results for mini scale-up crystallization trials

| | Observations: Alter Solvent Addition | Observations: After ASA | Observations: After Temp. Cycling | Isolated Yield/% | Solid Purity/ % area | XRPD Wet | XRPD Dry |
|---|---|---|---|---|---|---|---|
| 1 tBME:Heptane 50:50 | Clear solution | Solid[a] | Slurry | 60 | 99.2 | CRY | CRY |
| 2 MEK:Heptane 20:80 | Clear solution | Cloudy solution + oil | Slurry[a] | 66 | 99.0 | CRY | CRY |
| 3 THF:Heptane 22:78 | Clear solution | Cloudy solution + gum | Slurry[a] | 71 | 98.9 | CRY | CRY |

[a]Solids on vial walls;
CRY: Crystalline

Example 3B

Crystallization of the Compound of Formula I in Free Base Form from Different Batches Approximately 10 mg of the compound of Formula I in free base form from 3 different batches (LNB18319/13/1, LNB18319/22/1 and LNB18319/148/1) was weighed into 3×2 mL vials and a stirrer bar was added to each vial as Experiment 1, 2, and 3 respectively. 1 mL of tBME was added to each vial at 20° C. with stirring. The experiments were heated to 40° C. over 10-15 min. The experiments were stirred for 1 h at 40° C. and then cooled to 20° C. at 1° C./min. Anti-solvent addition of 1 mL of heptane was carried out at 20° C. After anti-solvent addition was complete, the experiments were temperature cycled for ca. 19 h: hold 1 h at 40° C., ramp 0.1° C./min to 5° C., hold 1 h at 5° C., and ramp 0.1° C./min to 40° C. After temperature cycling was complete, stirring was halted and the resulting solids were allowed to settle at 5° C. The solids were isolated by centrifugation (0.22 μm nylon filter) as wet solids. The wet solids were analyzed by XRPD. The XRPD plate was dried under vacuum at ca. 20° C. for ca. 22 h, then the dried solids were re-analyzed by XRPD. FIG. 35 shows the X-ray powder diffraction patterns of the wet solids and dry solids.

The following results and observations were obtained from these experiments (see Table 5 for further details):

The free base material prepared from HCl batch of the compound of Formula I: FP-000704 did not fully dissolve in all experiments, even after stirring at 40° C. for 1 h. Gum remained on the bottom of the vials for two of the batches of free base.

After anti-solvent addition at 20° C., thin slurries were present in all experiments, with some gum remaining in experiments using two of the batches of free base.

After temperature cycling overnight, all experiments formed slurries.

XRPD analysis showed that all isolated solids were consistent with the crystalline Form I, which was retained after drying.

TABLE 5

Results for small-scale crystallization trials using different batches of the compound of Formula I free base

| | Final Solvent System/v/v % | Observations After Solvent Addition | After ASA | After Temp. Cycling | XRPD Wet | XRPD Dry |
|---|---|---|---|---|---|---|
| 1 | BME:Heptane 50:50 | Clear solution | Thin slurry | Slurry | CRY | CRY |
| 2 | | Some gum | Thin slurry, some gum | Slurry | CRY | CRY |
| 3 | | Some gum | Thin slurry, some gum | Slurry | CRY | CRY |

CRY: Crystalline

Example 3C

Figure 36:
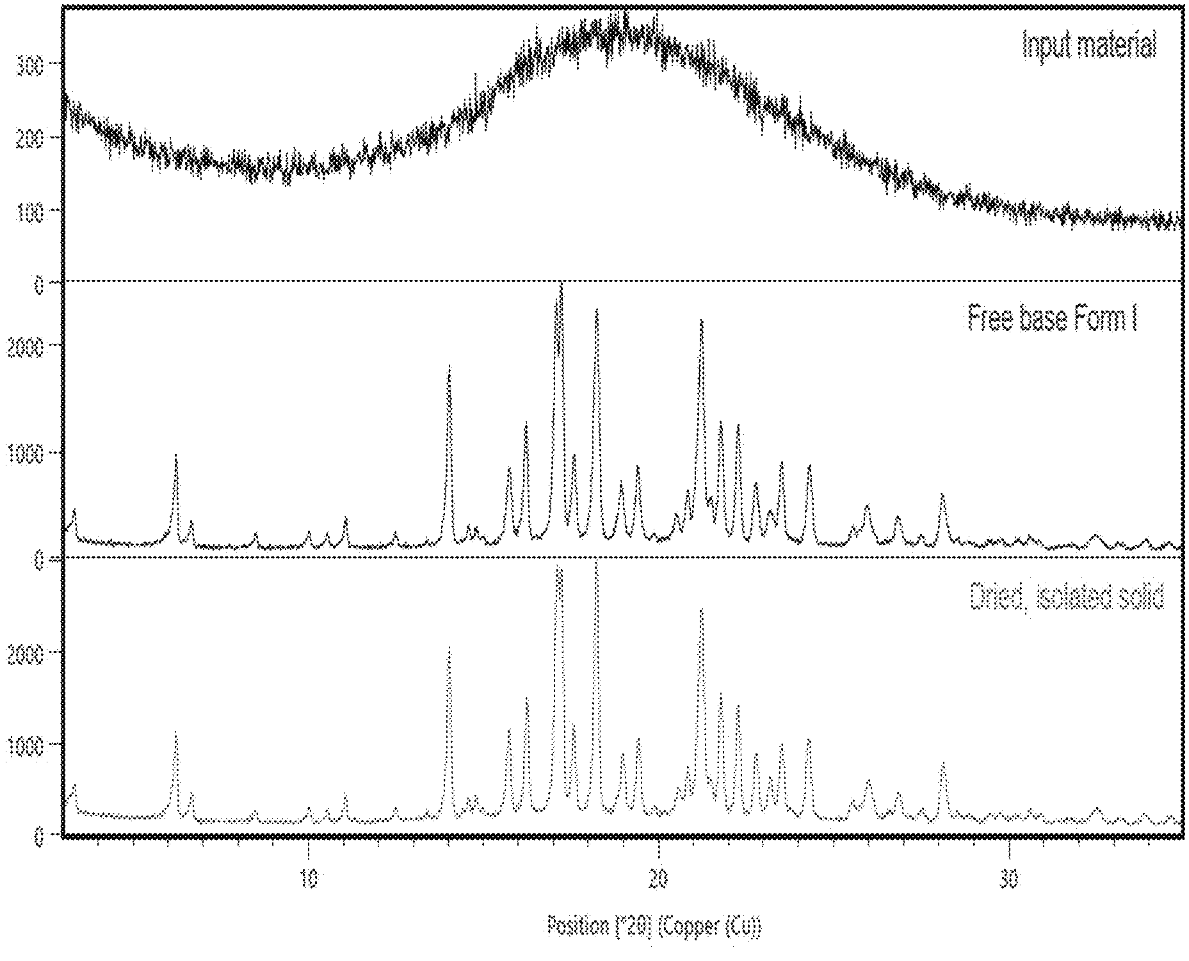
FIG. 36 shows the X-ray powder diffraction pattern comparisons between the dry solids from the scale-up and the amorphous form from Example 1 and the crystalline Form I from Example 3B.

Scale-Up of the Crystalline Form I of the Compound of Formula I in Free Base Form Approximately 75 mg of the compound of Formula I free base was weighed into a 20 mL screw-cap vial and a stirrer bar was added. 7.5 mL of tBME was added to the vial at 20° C. while stirring. The experiment was heated to 40° C. over ca. 10-15 min. The experiment was stirred for 1 h at 40° C. and then cooled to 20° C. at 1° C./min. Anti-solvent addition of 7.5 mL of heptane was carried out at 20° C. (0.5 or 1.0 mL aliquots). After anti-solvent addition was complete, the experiment was heated to 40° at 1° C./min. The experiment was temperature cycled between 40° C. and 5° C. for ca. 17 h (1 h hold at 40° C. and 5° C.; 0.1° C./min ramp/cool). After the temperature cycling was complete, stirring was halted and the resulting solids allowed to settle at 5° C. Mother liquors were decanted and the solids were isolated by centrifugation (0.22 μm nylon filter). FIG. 36 shows the X-ray powder diffraction pattern comparisons between the dry solids from the scale-up and the amorphous form from Example 1 and the crystalline Form I from Example 3B.

The following results and observations were obtained from this experiment:

- After 1 h at 40° C., most of the input material had dissolved. A small amount of gum was observed.
- After anti-solvent addition of heptane at 20° C., the experiment had some gum adhered to the vial walls and the bottom of the vial.
- After temperature cycling overnight, a slurry formed. Some material was adhered to the vial walls and was reintroduced to the slurry 45 min prior to isolation.
- XRPD analysis showed that the solid was consistent with the crystalline Form I after drying.
- HPLC analysis indicated that the isolated material had purity of 99.4% area (cf. input material purity of 98.5% area) as shown in FIG. 37.
- 56 mg of the crystalline Form I was obtained from this experiment, giving an isolated yield of 74%.

Figure 39:
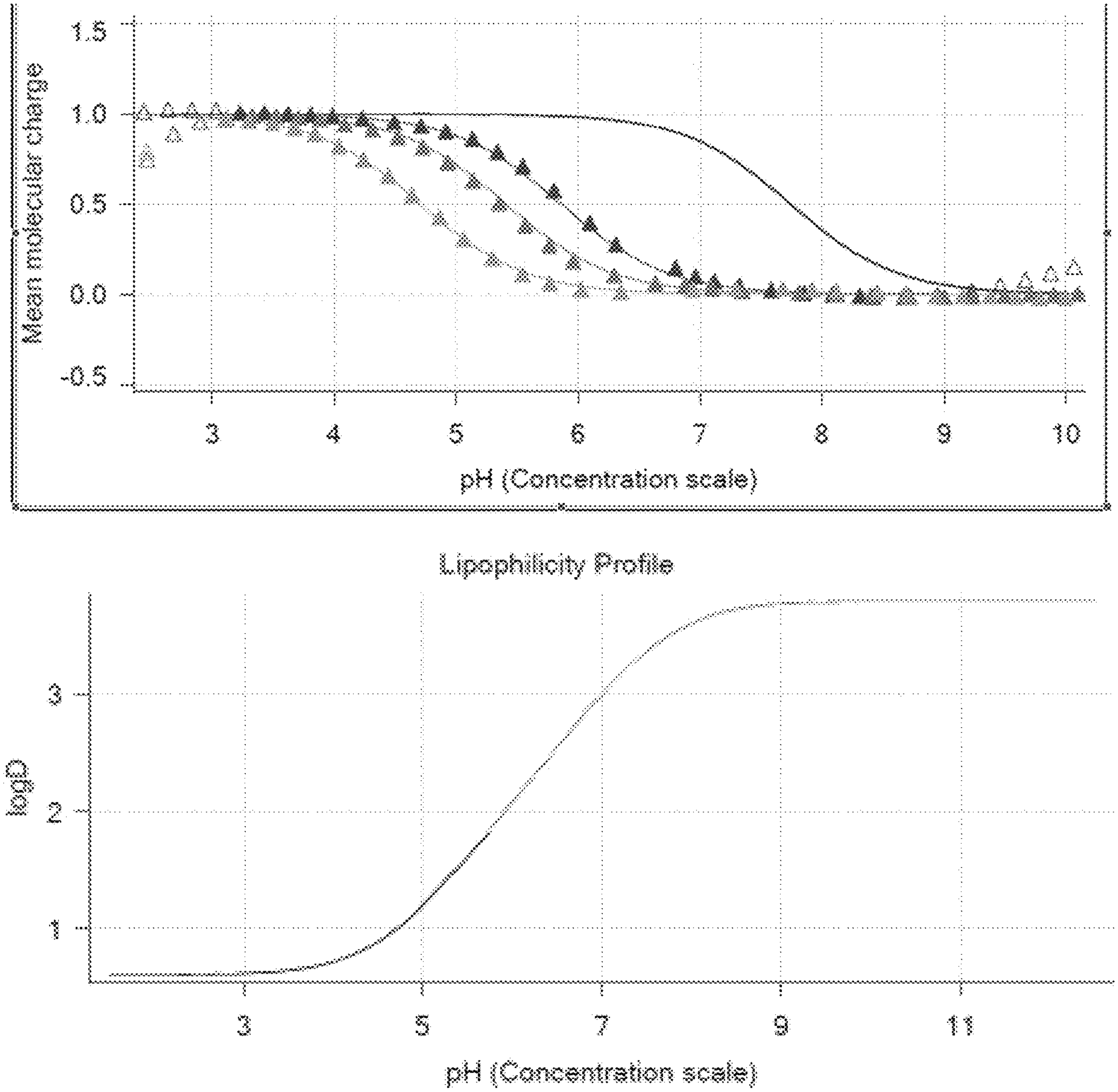
FIG. 39 shows the Potentiometric (pH-metric) LogP result of the crystalline Form I from the scale-up in Example 3C.

The crystalline Form I of the compound of Formula I in free base form prepared from the 75 mg scale in tBME: heptane 50:50 v/v % was subject to further analysis. The crystalline Form I was obtained in 74% isolated yield, with purity of 99.4% area. The free base had a spectrometric pKa with a value of 7.74±0.04 (base), determined from the spectroscopic data collected by Yasuda-Shedlovsky extrapolation of individual results as shown in FIG. 38. Potentiometric measurements were used to calculate the logP of the neutral (3.81±0.02) and the cationic (0.60±0.03) species as shown in FIG. 39.

A summary of the data obtained for the crystalline Form I is detailed in Table 6. The data in the Table 6 were obtained with the methods and analysis as described in the present disclosure.

TABLE 6

Summary of data for the crystalline Form I

| | | Free Base | |
|---|---|---|---|
| Final Solvent System/v/v % | | tBME:Heptane 50:50 | |
| Material Purity/ % area | Input | 98.5 | |
| | Solid | 99.2-99.4 | |
| Appearance | | White solid, NE12 | |
| Crystallibity (XRPD) | | Good, Form I | |
| Morphology (PLM) | | Small, some rod-like particles | |
| TGA | Mass Loss to 250° C./% | None | |
| | Endothermic Events/° C. | Onset 95, peak at 98 | |
| DSC (Endothermic Event, First Heat) | Onset/° C. | 95 | |
| | Peak/° C. | 98 | |
| $^{1}$H NMR | Solvent, % wt. | Heptane, 0.9 | |
| Water Uptake (DVS, 25° C.) | At 25° C./80%, RH, % | 0.5 | |
| | Post-DVS XRPD | Form I | |
| 14-Day Stability | Ambient | 98.6 | Form I |
| | 40° C./75% RH | 99.0 | Form I |
| Aqueous Solubility/mg/mL | | 0.097 | |
| $pK_a$ (Spectrometric) | | 7.74 ± 0.04 | |
| LogP (Potentiometric) | | 3.81 ± 0.02 (neutral)<br>0.60 ± 0.03 (cationic) | |

Example 4

Attempted Crystallization of HCl Salt

Attempts to crystallize the HCl salt of the compound of Formula I were unsuccessful under the conditions listed in Table 7. The HCl salt was prepared with the following procedures:

- Approximately 20 mg of amorphous free base was weighed out into 1.5 mL screw-cap vials and a stirrer bar was added.
- 200 μL of the appropriate solvent system was added to the free base.
- The experiments were stirred at 40° C. for ca. 1 min and then 1.1 eq. of HCl was added to the solutions of free base.
- Experiments were temperature cycled between 40° C. and 5° C. (1 h hold; 0.1° C./min ramp/cool) for ca. 23 h.
- ASA at 20° C. was carried out for all experiments followed by further temperature cycling for ca. 22 h. Further ASA was then carried out if required, prior to isolation. See Table 7 for details.
- Material was isolated at 10° C. by decanting the mother liquor and analyzed by XRPD.
- All isolated material was dried under vacuum at 40° C. for ca. 21 h then re-analyzed by XRPD.
- The XRPD plate was stored at 40° C./75% RH for 94-96 h and then samples were re-analyzed.

TABLE 7

| | Experimental details for HCl salt crystallization experiments | | | | | |
|---|---|---|---|---|---|---|
| | Initial Solvent System | | Additional Solvents | | | |
| | Solvent System (v/v) | Vol./μL | Anti-Solvent | ASA (1) Vol./μL | ASA (2) Vol./μL | Final S:AS:AS Ratio/v/v/v % |
| 1 | Acetone | 200 | Heptane | 750 | 200 | 17:83 |
| 2 | Acetonitrile | 200 | tBME | 750 | 600 | 13:87 |
| 3 | Ethanol | 200 | Heptane | 750 | 200, 500* | 12:58:30 |
| 4 | Ethyl acetate | 200 | Heptane | 750 | 200 | 17:83 |
| 5 | THF | 200 | Heptane | 750 | 200 | 17:83 |
| 6 | 2-PrOH:Water 75:25 | 200 | tBME | 750 | 600 | 13:87 |

*tBME used as second anti-solvent during ASA 2.
ASA: Anti-solvent addition

Figure 41:
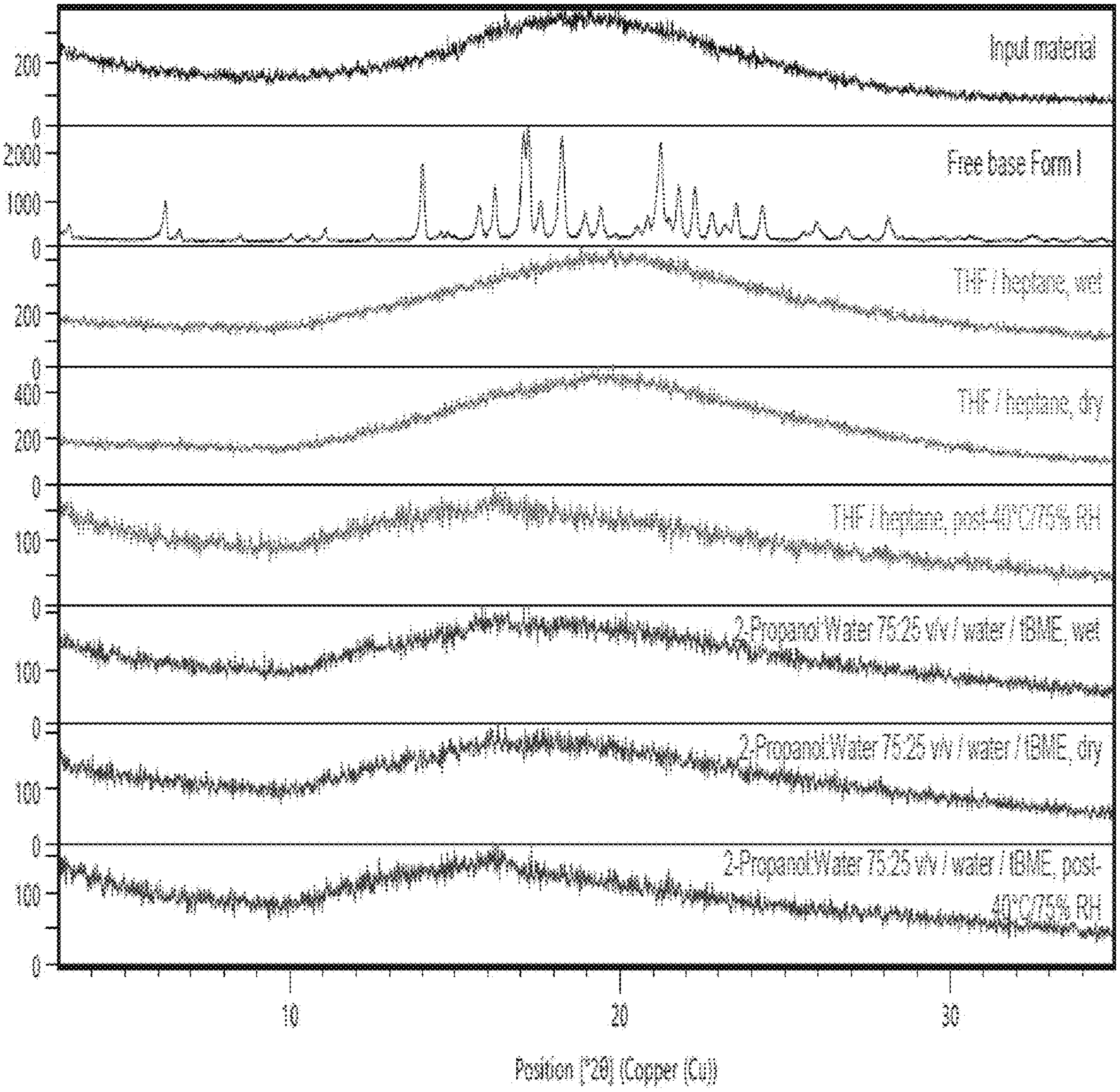

FIGS. 40 and 41 shows X-ray powder diffraction patterns of the HCl salt of the compound of Formula I directly isolated from various conditions in comparison with the free base Form I and amorphous form of the compound of Formula I.

The following results and observations were obtained from these experiments:

- Solutions were obtained after addition of the acid in acetone, acetonitrile, ethanol and 2-propanol:water 75:25 v/v, which were maintained after temperature cycling.
- Gum was obtained from experiments initially carried out in acetone and acetonitrile after ASA, with gum also obtained from experiments initially carried out in ethyl acetate and THF.
- Separation was noted after ASA in experiments carried out in ethanol and 2-propanol:water 75:25 v/v; however, gum was obtained after temperature cycling for the experiment carried out using 2-propanol:water 75:25 v/v.
- After isolation, gums were obtained from most experiments. The material isolated from the experiment carried out in ethyl acetate was sticky solid.
- XRPD analysis indicated that all isolated materials were amorphous, with no change to the diffractograms noted after drying or storage at 40° C./75% RH.
- See Table 8 for further details.

TABLE 8

| | Results and observations from HCl salt formation experiments | | | | | | | | | | | |
|---|---|---|---|---|---|---|---|---|---|---|---|---|
| | | | Final | Observations | | | | | | | | |
| | Initial Solvent | Anti- | S:AS Ratio | Acid | Temp. Cycling | | Temp. Cycling | | XRPD | | | |
| | System (v/v) | Solvent | v/v | Addition | (1) | ASA | (2) | Isolation | Wet | Dry | 40/75 |
| 1 | Acetone | Heptane | 17:83 | Solution | Solution | Gum | Gum | Gum | AM | AM | AM |
| 2 | Acetonitrile | tBME | 13:87 | Solution | Solution | Gum | Gum | Gum | AM | AM | AM |
| 3 | Ethanol | Heptane * | 12:58:30 | Solution | Solution | Separated | Separated | Gum | AM | AM | AM |
| 4 | Ethyl acetate | Heptane | 17:83 | Gum | Gum | Gum | Gum | Sticky solid | AM | AM | AM |
| 5 | THF | Heptane | 17:83 | Cloudy | Gum | Gum | Gum | Gum | AM | AM | AM |
| 6 | 2-PrOH:$H_2O$ (75:25) | tBME | 13:87 | Solution | Solution | Separated | Gum | Gum | AM | AM | AM |

* tBME used as second anti-solvent during ASA 2;
AM: Amorphous

Example 5

XRPD Analysis

The X-ray powder diffraction patterns of Example 1 were determined using a PANalytical X'pert pro with PIXcel detector (128 channels), scanning the samples between 3 and 35° 2θ. The material was gently ground (where required) to release any agglomerates and loaded onto a multi-well plate with Mylar polymer film to support the sample. The multi-well plate was then placed into the diffractometer and analyzed using Cu K radiation ($\alpha_1 \lambda$=1.54060 Å; $\alpha_2$=1.54443 Å; β=1.39225 Å; α1: $\alpha_2$ ratio=0.5) running in transmission mode (step size 0.0130° 2θ, step time 18.87 s) using 40 kV/40 mA generator settings. Data were visualized and images generated using the HighScore Plus 4.7 desktop application (PANalytical, 2017). FIG. 8 shows the X-ray powder diffraction pattern for the crystalline Form I. Peak positions are provided in Table 9.

TABLE 9

| Angle (2θ) | d value (Angstrom) |
|---|---|
| 3.3557 | 26.33028 |
| 6.2528 | 14.13565 |
| 6.7076 | 13.17800 |
| 8.5373 | 10.35747 |

TABLE 9-continued

| Angle (2θ) | d value (Angstrom) |
|---|---|
| 10.0648 | 8.78868 |
| 10.5705 | 8.36933 |
| 11.0872 | 7.98048 |
| 11.3306 | 7.80953 |
| 12.4996 | 7.08171 |
| 13.3894 | 6.61301 |
| 14.0399 | 6.30806 |
| 14.5916 | 6.07077 |
| 14.8264 | 5.97515 |
| 15.0130 | 5.90128 |
| 15.7617 | 5.62262 |
| 16.2674 | 5.44896 |
| 17.1052 | 5.1839 |
| 17.2582 | 5.1383 |
| 17.6034 | 5.03829 |
| 18.2555 | 4.85978 |
| 18.9918 | 4.67300 |
| 19.4355 | 4.56731 |
| 19.9279 | 4.45554 |
| 20.1779 | 4.40091 |
| 20.5819 | 4.31542 |
| 20.8530 | 4.25994 |
| 21.2479 | 4.18165 |
| 21.4811 | 4.13677 |
| 21.7838 | 4.07997 |
| 22.2628 | 3.99326 |
| 22.7698 | 3.90225 |
| 22.8328 | 3.89483 |
| 23.2006 | 3.83392 |
| 23.5437 | 3.77882 |
| 23.8107 | 3.73705 |
| 24.3278 | 3.65878 |
| 25.5647 | 3.48449 |
| 25.9949 | 3.42779 |
| 26.5815 | 3.35346 |
| 26.8967 | 3.31488 |
| 27.5214 | 3.24104 |
| 28.1223 | 3.17313 |
| 28.5405 | 3.12759 |
| 28.8662 | 3.09303 |
| 29.4659 | 3.03144 |
| 29.7634 | 3.00181 |
| 30.2450 | 2.95510 |
| 30.6144 | 2.92028 |
| 30.9458 | 2.88975 |
| 31.7973 | 2.81429 |
| 32.4476 | 2.75936 |
| 33.1572 | 2.70191 |
| 33.8784 | 2.64602 |
| 34.6636 | 2.58786 |

Example 6

Thermogravimetric/Differential Scanning Calorimetry (TG/DSQ)

Crystalline forms of the compound of Formula I, including the crystalline Form I, were analyzed using Thermogravimetric/Differential Scanning Calorimetry. Approximately 1-5 mg of material was added into a pre-tared open aluminum pan and loaded into a TA Instruments Discovery SDT 650 Auto—Simultaneous DSC and held at room temperature. The sample was then heated at a rate of 10° C./min from 30° C. to 400° C. during which time the change in sample weight was recorded along with the heat flow response (DSC). Nitrogen was used as the sample purge gas, at a flow rate of 200 $cm^3$/min.

Example 7

Differential Scanning Calorimetric Analysis (DSC)

Crystalline forms of the compound of Formula I, including the crystalline Form I, were analyzed using Differential Scanning Calorimetry. Approximately 5 mg of material was weighed into an aluminum DSC pan and sealed nonhermetically with a pierced aluminum lid. The sample pan was then loaded into a Seiko DSC6200 (equipped with a cooler) or a TA DSC2500 and held at 20° C. Once a stable heat-flow response was obtained, the sample and reference were heated to the required upper temperature (250° C.) at a scan rate of 10° C./min and the resulting heat flow response monitored. The sample was held at the upper temperature for 3 minutes, before it was cooled at 10° C./min to 20° C. and then reheated to the upper temperature at 10° C./min. Nitrogen was used as the purge gas, at a flow rate of 50 $cm^3$/min.

Example 8

Polarized Light Microscopy (PLM)

Crystalline forms of the compound of Formula I, including the crystalline Form I, were determined using an Olympus BX53 polarizing microscope, equipped with a Motic camera. Images were captured using Motic Images Plus 3.0. All images were recorded using the 20× objective, unless otherwise stated.

Example 9

Nuclear Magnetic Resonance Spectroscopy (NMR)

Crystalline forms of the compound of Formula I, including the crystalline Form I, were analyzed using $^1H$ NMR spectroscopic experiments, which were performed on a Bruker AV400 (frequency: 400 MHz for protons). Experiments were performed in d6-dimethylsulfoxide and samples were prepared to ca. 5-10 mM concentration.

Example 10

Infrared Spectroscopy (FT-IR)

Crystalline forms of the compound of Formula I, including the crystalline Form I, were analyzed using Infrared spectroscopy, which was carried out on a Bruker ALPHA P spectrometer. Sufficient material was placed onto the center of the plate of the spectrometer and the spectra were obtained using the following parameters:

Resolution: 4 cm−1

Background Scan Time: 16 scans Sample

Scan Time: 16 scans

Data Collection: 4000 to 400 cm−1

Result Spectrum: Transmittance

Software: OPUS version 6.

Example 11

Dynamic Vapour Sorption (DVS)

Crystalline forms of the compound of Formula I, including the crystalline Form I, were analyzed using Dynamic Vapour Sorption (DVS). Approximately 10-15 mg of sample was placed into a mesh vapour sorption balance pan and loaded into a DVS Intrinsic dynamic vapour sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 minutes, maximum step length 120 minutes) at 25° C. After completion of the sorption cycle, the sample was dried using the same procedure to 0% RH and then a second sorption cycle back to 40% RH was carried out. Two cycles were performed. The weight change during the sorption/desorption cycles were plotted, allowing the hygroscopic nature of the sample to be determined. XRPD analysis was then carried out on the residual solid.

Example 12

Karl Fischer Coulometric Titration (KF)

Crystalline forms of the compound of Formula I, including the crystalline Form I, were analyzed using Karl Fischer Coulometric Titration (KF). Approximately 10-15 mg of solid material was weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

Example 13

Appearance Testing

Crystalline forms of the compound of Formula I, including the crystalline Form I, were analyzed using Appearance Testing. The solid sample, in a clear, colorless, glass vial, was examined against a matt white background. The color of the material was determined with reference to the Sigma Aldrich color chart.

Example 14

High Performance Liquid Chromatography-Ultraviolet Detection (HPLC-UV)

Crystalline forms of the compound of Formula I, including the crystalline Form I, were analyzed using High Performance Liquid Chromatography-Ultraviolet Detection (HPLC-UV).

Column: Waters XSelect CSH XP C18 (100×4.6 mm; 2.5 μm)

Mobile Phase A: 0.1% Phosphoric acid in water

Mobile Phase B: 0.1% Phosphoric acid in acetonitrile

Needle Wash: Water:acetonitrile 90:10 v/v

Diluent: Water:acetonitrile 90:10 v/v (dissolve in acetonitrile, then add water)

Autosampler Temperature: Ambient

Flow Rate: 1.0 mL/min

Runtime: 30 minutes

Column Temperature: 25° C. (±1° C.) Injection Volume: 5 μL

Sample Concentration: 0.25 mg/mL Detection: 210 nm

Gradient Program:

| Time/min | MP A (%) | MP B (%) |
|---|---|---|
| 0.0 | 90 | 10 |
| 10.0 | 70 | 30 |
| 25.0 | 10 | 90 |
| 25.1 | 90 | 10 |
| 30.0 | 90 | 10 |

Example 15

High Performance Liquid Chromatography-Charged Aerosol Detection (HPLC-CAD)

Crystalline forms of the compound of Formula I, including the crystalline Form I, were analyzed using High Performance Liquid Chromatography-Charged Aerosol Detection (HPLC-CAD).

Guard Column: Phenomenex Aeris XB-C18 100 Å, 150×4.6 mm, 3.6 μm

Column: P2 Acclaim Trinity 50×2.1 mm, 3 μm

Mobile Phase A: Water

Mobile Phase B: 100 mM Ammonium formate pH 3.65

Diluent: Water:acetonitrile 50:50 v/v

Autosampler Temperature: Ambient

Flow Rate: 0.45 mL/min

Runtime: 23 minutes

Column Temperature: 30° C. (±1° C.)

Injection Volume: 4 μL

Counterion Concentration: 0.2 mg/mL of chloride (based on expected stoichiometry)

Detection: CAD Corona Ultra RS

CAD Filter: Corona for Corona Ultra CAD Nebulizer Temperature: 30° C.

Gradient Program:

| Time/min | MP A (%) | MP B (%) |
|---|---|---|
| 0.0 | 80 | 20 |
| 1.7 | 80 | 20 |
| 7.0 | 5 | 95 |

-continued

| Time/min | MP A (%) | MP B (%) |
|---|---|---|
| 11.7 | 5 | 95 |
| 12.3 | 80 | 20 |
| 23.0 | 80 | 20 |

Example 16

Stability Studies

Crystalline forms of the compound of Formula I, including the crystalline Form I, including the crystalline Form I were analyzed regarding stability. Approximately 10 mg of free base Form I was subjected to 14-day stability testing under the following conditions to assess developability:

40° C./75% RH (open vial);

Ambient light, temperature and humidity conditions (open vial).

Figure 42:
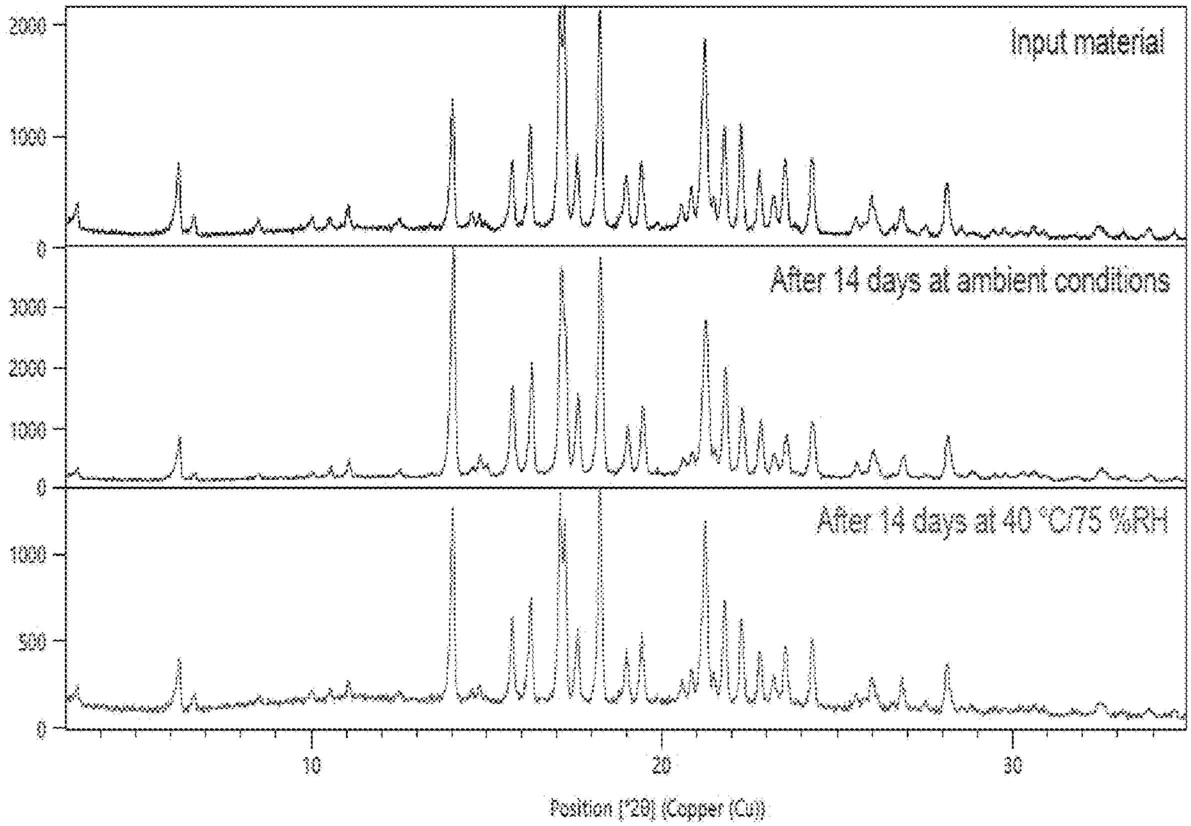
FIG. 42 shows X-ray powder diffraction patterns of the crystalline Form I before and after 14-days under ambient conditions and at 40° C./75% relative humidity respectively.

After 2 weeks under the specified conditions, XRPD and HPLC analysis was carried out on the resultant solid material. The sample appearance was monitored over 14 days. FIG. 42 shows X-ray powder diffraction patterns of the crystalline Form I before and after 14 days at ambient conditions and at 40° C./75% relative humidity.

The following results were obtained from these experiments:

XRPD analysis showed that the crystalline Form I was retained under both storage conditions.

HPLC analysis showed that there was no significant degradation of the crystalline Form I at 40° C./75% RH and under ambient conditions (decrease in purity of ≤0.3% area) as shown in FIG. 43-44.

See Table 10 for further details.

TABLE 10

Results and observations from stability studies

| Input Material | | | Solid | | | |
|---|---|---|---|---|---|---|
| Material | Purity/ % area | Appearance* | Storage Conditions | Purity/ % area | XRPD | Post-Storage Observations |
| Crystalline Form I | 98.9 | White solid (NE12) | Ambient | 98.6 | CRY | White solid (NE12) |
| | | | 40° C./75% RH | 99.0 | CRY | White solid (NE12) |

*Appearance testing carried out with respect to the Sigma Aldrich color chart
CRY: Crystalline

Example 17

Aqueous Solubility Studies

The aqueous solubility of the crystalline Form I was assessed using the following procedure:

Approximately 10 mg of the dried material was slurried in deionized water (100 μL) at 20° C. with stirring.

Further aliquots of water (50 μL) were added until a mobile slurry was obtained. A total of 600 μL was used.

The slurry was stirred at 20° C. for 24 h then separated by centrifugation (0.22 μm nylon filter).

Figure 45:
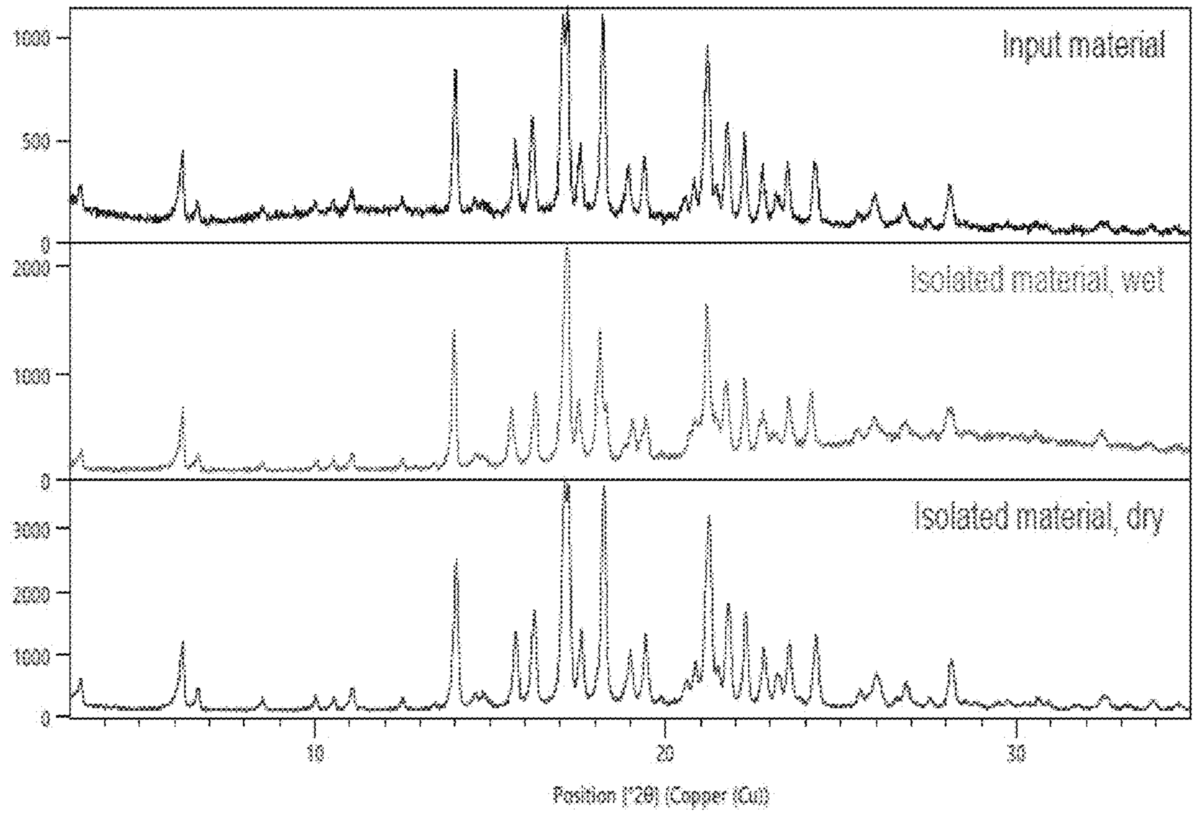
FIG. 45 shows X-ray powder diffraction patterns of the isolated materials from the aqueous solubility studies in dry and wet forms.

The residual solid was analyzed by XRPD and then dried under vacuum at ambient temperature (ca. 20° C.) for 72 h, prior to re-analysis by XRPD. The results are shown in FIG. 45.

The pH of the mother liquor was measured.

The mother liquors were analyzed by HPLC for purity and concentration.

The following results were obtained from this experiment:

The crystalline Form I was retained after slurrying in water at 20° C. and after drying. The diffractogram of the wet material had slightly lower crystallinity than both the input material and the dried material, likely due to some solvent retention after centrifugation.

Figure 47:
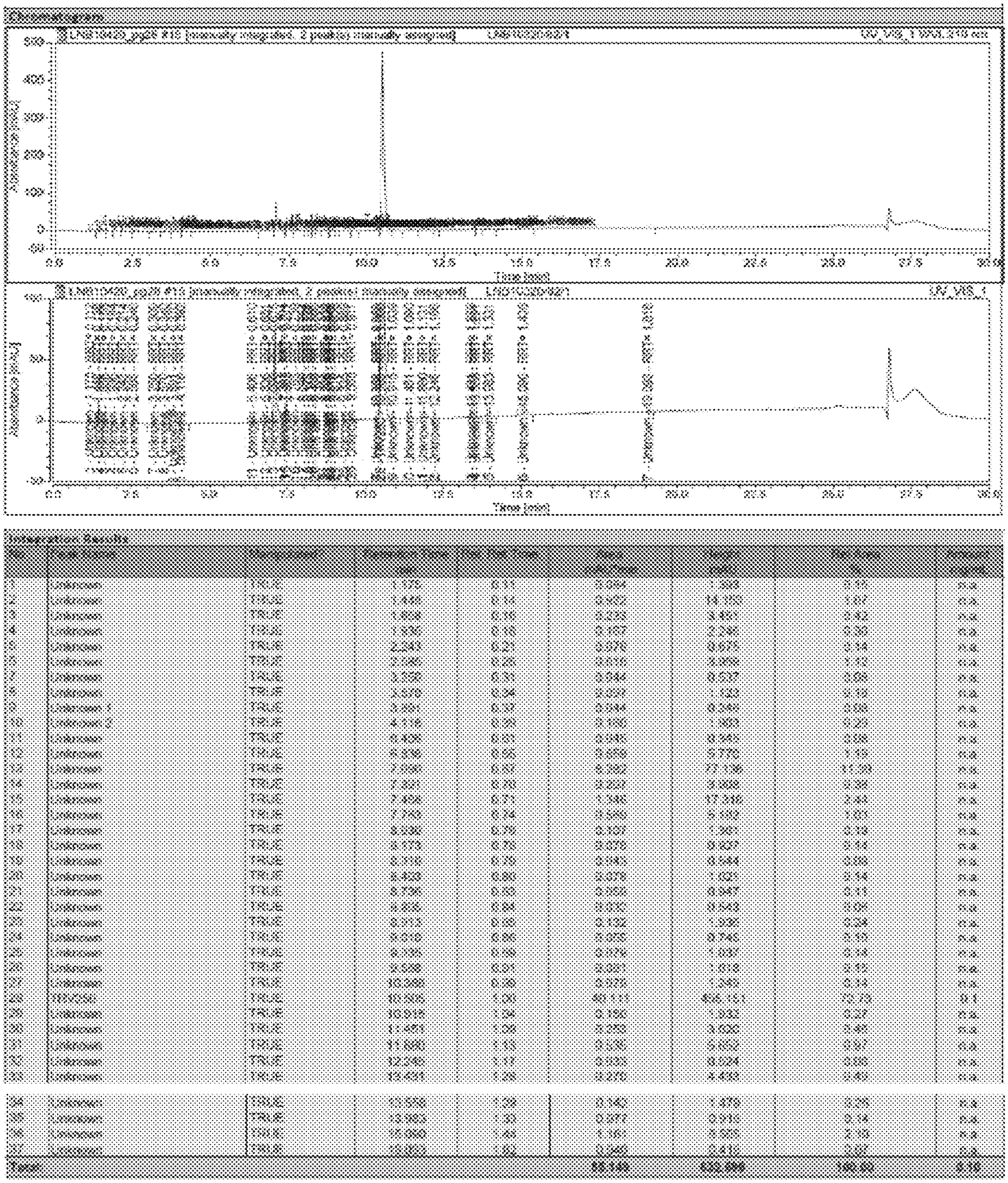
FIG. 47 shows the HPLC chromatogram of the solution with the dissolved compound of Formula I from the aqueous solubility studies.

HPLC analysis indicated that the crystalline Form I had aqueous solubility of 0.097 mg/mL, with solution purity of 72.8% area (note that the low concentration of the mother liquor resulted in the concentration of the sample analyzed for purity being below the working concentration of the method). The pH of the mother liquor was ca. 6.8. The results are shown in FIG. 46-47.

The dried, residual solid isolated after slurrying the crystalline Form I in water at 20° C. had purity of 99.4% area (cf. 99.2% area for input material).

See Table 11 for further details.

TABLE 11

| Results from aqueous solubility study | | | | | | | |
|---|---|---|---|---|---|---|---|
| Input Material | | Solution | | | Solid | | |
| | Slurry | Concentration/ | Purity/ | | Purity/ | XRPD | |
| Material | Conc/mg/mL | mg/mL | % area | pH | % area | Wet | Dry |
| The crystalline Form I | 17 | 0.097 | 72.8* | 6.84 | 99.4 | CRY | CRY |

*concentration of solution was below working concentration of purity method
CRY: Crystalline Example 18 pKa and LogP

Crystalline forms of the compound of Formula I, including the crystalline Form I, were analyzed using pKa and LogP. An automated titrator system with an incorporated UV-Vis spectrometer (SiriusT3™, Pion Inc.) was used to acquire the spectrometric and potentiometric data. The optical system consisted of a photodiode array detector with a deuterium lamp and a fiber optic dip probe.

The titrator module consisted of a temperature controller (by Peltier device with in-situ thermocouple), pH electrode, an overhead stirrer, and motorized dispensers for the automatic delivery of assay titrants and reagents via capillaries. The instrumentation was operated using SiriusT3Control software (V2.0). Data processing and generation of the reported pKa and logP values was carried out using SiriusT3Refine software (V2.0). The titrants used were 0.5 M hydrochloric acid and 0.5 M potassium hydroxide, standardized using potassium hydrogen phthalate. ACS or HPLC grade methanol cosolvent was used for pKa determination. Spectrophotometric experiments were carried out in the presence of a mid-range buffer solution (15 mM di-potassium hydrogen orthophosphate) or Neutral Linear Buffer™ to prevent uncontrolled pH-drift at mid-range pH. For logP assays, ACS or HPLC grade 1-octanol was used as the partition solvent.

All experiments were carried out at a controlled temperature of 25.0±0.2° C. The pH range of titration assays is set between pH 2.0 to pH 12.0 unless otherwise stated. Prior to use, 0.5 M KOH base titrant is standardized by the titration of approximately 15 mg of potassium hydrogen phthalate, in triplicate. 0.5 M HCl titrant is subsequently standardized against the base titrant. The assay media for pKa determination is kept at a constant ionic strength of 0.15 M KCl and under argon atmosphere.

Spectrometric (UV-metric) pKa

Approximately 20 μL of a 10 mM DMSO stock solution was pipetted, in triplicate, into 3×5 mL glass assay vials containing 25 μL of phosphate buffer. An accompanying UV-metric calibration assay was prepared by pipetting 20 μL of DMSO into a 5 mL glass assay vial containing 25 μL of phosphate buffer. The sample was titrated in three UV-metric single titrations from pH 1.5 to pH 12.5 at concentrations of 110-86 M, under methanol-water co-solvent conditions (the methanol mixing ratio varied from 45.6 to 29.0% w/w). The UV-metric pKa experiment was conducted at 25.0±0.2° C. and a potentiometric pKa assay was performed to confirm the pKa. No precipitation of the sample from solution was observed and one pKa, with an aqueous value of 7.74±0.04 (base) was determined from the spectroscopic data collected by Yasuda-Shedlovsky extrapolation of the individual results obtained.

Potentiometric (pH-metric) pKa

An additional potentiometric assay was carried out to confirm the pKa. 0.81 mg of sample was weighed into a 5 mL glass assay vial and a pH-metric titration was carried out from pH 2.0-pH 12.0 under methanol-water co-solvent conditions. The aqueous pKa was extrapolated from the apparent pKa measured in the presence of co-solvents, using the Yasuda-Shedlovsky extrapolation equation. The pH-metric pKa experiment was conducted at 25.0 f 0.2° C. The potentiometric assay confirmed the spectrometric pKa and showed that there were no further pKas associated with the sample within the measurable pH range (2.0-12.0).

Potentiometric (pH-metric) LogP 0.79 mg of sample was weighed into a 5 mL glass assay vial and titrated in a pH-metric triple titration in the presence of octanol from pH 2.0-12.0 at concentrations of 1.5-0.5 mM. The partition ratios of octanol/water were 0.012:1, 0.038:1 and 0.517:1. LogP was determined by comparing the pKa in water with the apparent pKa in the presence of octanol. The pH-metric logP experiment was conducted at 25.0±0.2° C. A lipophilicity profile (logD vs. pH) of the compound was calculated from the experimentally determined pKa and logP. The logD values are detailed in Table 12.

TABLE 12

| The crystalline Form I logD values | | |
|---|---|---|
| pH | LogD | Comment |
| 1.000 | 0.60 | |
| 1.200 | 0.60 | Stomach pH |
| 3.000 | 0.61 | |
| 4.000 | 0.71 | |
| 5.000 | 1.20 | |
| 6.000 | 2.08 | |
| 6.500 | 2.55 | |
| 7.000 | 3.00 | |
| 7.400 | 3.31 | Blood pH |
| 8.000 | 3.62 | |
| 9.000 | 3.79 | |
| 10.000 | 3.81 | |
| 11.000 | 3.81 | |
| 12.000 | 3.81 | |

While the embodiments have been depicted and described by reference to exemplary embodiments, such a reference does not imply a limitation on the scope, and no such limitation is to be inferred. The embodiments are capable of considerable modification, alteration, and equivalents in form and function, as will occur to those ordinarily skilled in the pertinent arts having the benefit of this disclosure.

The depicted and described embodiments are exemplary only, and are not exhaustive of the scope.

All references cited herein are hereby incorporated by reference in their entirety.

What is claimed is:

1. A crystalline Form I of (−)-6-{[(trans, trans)-4-[3-(2-methoxyethoxy)phenyl]-2-methyl-1-[2-(1H-pyrrol-1-yl)ethyl]piperidin-3-yl]methoxy}-2,3-dihydro-1H-isoindol-1-one having a formula of Formula I

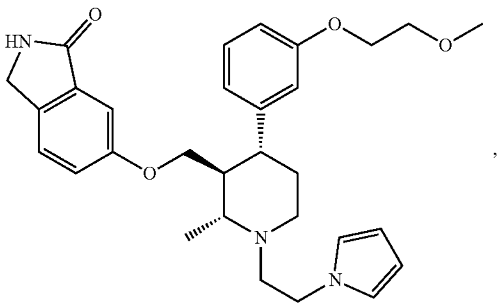

, wherein the crystalline Form I is characterized by an X-ray powder diffraction pattern comprising one or more peaks at about 18.3, at about 17.1, at about 17.3, at about 21.2, and at about 14.0±0.5 degrees 2θ.

2. A crystalline Form I of (−)-6-{[(trans, trans)-4-[3-(2-methoxyethoxy)phenyl]-2-methyl-1-[2-(1H-pyrrol-1-yl)ethyl]piperidin-3-yl]methoxy}-2,3-dihydro-1H-isoindol-1-one having a formula of Formula I

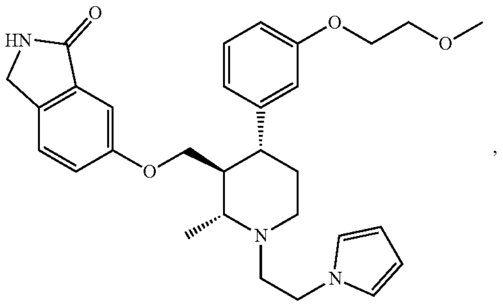

, wherein the crystalline Form I is characterized by an X-ray powder diffraction pattern comprising one or more peaks as shown in FIG. 16.

3. The crystalline Form I of claim 1 characterized by an X-ray powder diffraction pattern comprising one or more d-spacing values at about 6.3, at about 5.1, at about 5.2, at about 4.9, and at about 4.2±0.5 degrees angstroms.

4. A pharmaceutical composition comprising the crystalline Form I of claim 2 and a pharmaceutically acceptable excipient.

5. A pharmaceutical composition comprising the crystalline Form I of claim 1 and a pharmaceutically acceptable excipient.

6. The pharmaceutical composition of claim 5, further comprising an additional drug for the treatment of pain, migraine, headache, depression, Parkinson's disease, anxiety, overactive bladder, medication overuse headache, hyperalgesia, decreasing nociceptive sensitization, pain in an opioid exposed subject, PTSD other disorders and conditions described herein or any combination thereof.

7. A process for preparing a crystalline form of the compound of Formula I, comprising crystallizing the crystalline form of the compound of Formula I and optionally isolating the crystalline form of the compound of Formula I.

8. A method of alleviating the symptoms of or diminishing the extent of a condition, disorder, or disease selected from the group consisting of pain, neuropathic pain, migraine, headache, depression, Parkinson's disease, anxiety, overactive bladder, medication overuse headache, hyperalgesia, decreasing nociceptive sensitization, pain in an opioid exposed subject, and PTSD, or any combination thereof, the method comprising administering to a patient in need thereof, the crystalline Form I of claim 1, or a pharmaceutical composition comprising the crystalline Form I of claim 1 and a pharmaceutically acceptable excipient.

9. A method of treating hyperalgesia in a subject comprising administering to the subject comprising administering to a patient in need thereof, the crystalline Form I of claim 1, or a pharmaceutical composition thereof and a pharmaceutically acceptable excipient.

10. A method of decreasing nociceptive sensitization in a subject comprising administering to a patient in need thereof, the crystalline Form I of claim 1, or a pharmaceutical composition thereof and a pharmaceutically acceptable excipient.

11. A method of alleviating the symptoms of or diminishing the extent of pain in a subject comprising administering an opioid agonist to the subject until the opioid increases nociceptive sensitization in the subject and administering to a patient in need thereof, the crystalline Form I of claim 1, or a pharmaceutical composition thereof and a pharmaceutically acceptable excipient.

12. A method of alleviating the symptoms of or diminishing the extent of pain in an opioid exposed subject comprising:

a) administering an opioid agonist to the subject;

b) administering to the subject of step a), in the absence of the opioid administered in step a), the crystalline Form I of claim 1 or a pharmaceutical composition thereof and a pharmaceutically acceptable excipient.

13. The method of claim 12, wherein the opioid is morphine, oxycodone, hydrocodone, hydromorphone, fentanyl, meperidine, alfentanil, remifentanil, sufentanil, etorphine, buprenorphine, methadone, and/or heroin, or a pharmaceutically acceptable salt thereof.

14. A method of alleviating the symptoms of or diminishing the extent of medication overuse headache in a subject comprising administering to a patient in need thereof, the crystalline Form I of claim 1, or a pharmaceutical composition thereof and a pharmaceutically acceptable excipient.

15. The method of claim 14, wherein the medication overuse headache is caused by acetaminophen, aspirin, a mu-opioid agonist, a non-steroidal anti-inflammatory drug (NSAID), or a triptan.

16. A method of alleviating the symptoms of or diminishing the extent of migraine in a subject, the method comprising:

a) administering a triptan to a subject; and b) administering to a patient in need thereof, the crystalline Form I of claim 1, or a pharmaceutical composition comprising thereof and a pharmaceutically acceptable excipient.

17. The method of claim 16, wherein the crystalline Form I or the pharmaceutical composition thereof and a pharmaceutically acceptable excipient is administered in the absence of the triptan.

18. The method of claim 17, wherein the triptan is sumatriptan, rizatriptan, naratriptan, zolmitriptan, eletriptan, almotriptan, frovatriptan, avitriptan, or donitriptan, or a pharmaceutically acceptable salt thereof.

19. A method of treating neuropathic pain, the method comprising administering to a patient in need thereof, the crystalline Form I of claim 1, or a pharmaceutical composition thereof and a pharmaceutically acceptable excipient.

* * * * *